(12) United States Patent
Ramsing et al.

(10) Patent No.: US 11,111,535 B2
(45) Date of Patent: Sep. 7, 2021

(54) PROBES, LIBRARIES AND KITS FOR ANALYSIS OF MIXTURES OF NUCLEIC ACIDS AND METHODS FOR CONSTRUCTING THE SAME

(71) Applicant: QIAGEN GmbH, Hilden (DE)

(72) Inventors: Niels B. Ramsing, Risskov (DK); Peter Mouritzen, Jyllinge (DK); Søren Morgenthaler Echwald, Humlebæk (DK); Niels Tolstrup, Klampenborg (DK)

(73) Assignee: QIAGEN GmbH, Hilden (DE)

( * ) Notice: Subject to any disclaimer, the term of this patent is extended or adjusted under 35 U.S.C. 154(b) by 208 days.

(21) Appl. No.: 15/273,917

(22) Filed: Sep. 23, 2016

(65) Prior Publication Data

US 2017/0081719 A1 Mar. 23, 2017

Related U.S. Application Data

(62) Division of application No. 10/871,471, filed on Jun. 18, 2004, now abandoned.

(60) Provisional application No. 60/549,346, filed on Mar. 2, 2004.

(30) Foreign Application Priority Data

| Jun. 20, 2003 | (DK) | PA200300933 |
| Jul. 12, 2003 | (DK) | PA200301066 |
| Feb. 17, 2004 | (DK) | PA200400242 |
| Mar. 1, 2004 | (DK) | PA200400353 |

(51) Int. Cl.
| C12Q 1/68 | (2018.01) |
| C12P 19/34 | (2006.01) |
| C12Q 1/6876 | (2018.01) |
| C12Q 1/6816 | (2018.01) |
| G16B 25/00 | (2019.01) |
| C12N 15/10 | (2006.01) |

(52) U.S. Cl.
CPC ....... *C12Q 1/6876* (2013.01); *C12N 15/1065* (2013.01); *C12Q 1/6816* (2013.01); *G16B 25/00* (2019.02); *C12Q 2600/158* (2013.01)

(58) Field of Classification Search
CPC ............ C12Q 1/6816; C12Q 2525/113; C12Q 2531/113; C12Q 2525/204; C12Q 2537/143; C12Q 1/6876; C12Q 2561/113; C12Q 1/6837
See application file for complete search history.

(56) References Cited

U.S. PATENT DOCUMENTS

| 3,687,808 A | 8/1972 | Merigan et al. |
| 4,889,818 A | 12/1989 | Gelfand et al. |
| 5,432,272 A | 7/1995 | Benner |
| 6,043,060 A | 3/2000 | Imanishi |
| 6,154,707 A | 11/2000 | Livak et al. |
| 6,268,490 B1 | 7/2001 | Imanishi et al. |
| 6,322,976 B1 | 11/2001 | Aitman et al. |
| 6,579,680 B2 | 6/2003 | Frutos et al. |
| 9,464,106 B2 | 10/2016 | Kauppinen et al. |
| 2001/0053519 A1* | 12/2001 | Fodor ............. B01J 19/0046 435/6.11 |
| 2002/0068708 A1 | 6/2002 | Wengel et al. |
| 2002/0197630 A1 | 12/2002 | Knapp et al. |
| 2003/0064382 A1 | 4/2003 | Preparata et al. |
| 2003/0082807 A1 | 5/2003 | Wengel |
| 2003/0087230 A1 | 5/2003 | Wengel |
| 2003/0092905 A1 | 5/2003 | Kochkine et al. |
| 2003/0134808 A1 | 7/2003 | Wengel |
| 2003/0144231 A1 | 7/2003 | Wengel et al. |
| 2003/0224377 A1 | 12/2003 | Wengel et al. |
| 2004/0014959 A1 | 1/2004 | Sorensen et al. |
| 2004/0110308 A1 | 6/2004 | Laikhter et al. |
| 2005/0287566 A1 | 12/2005 | Wengel et al. |

FOREIGN PATENT DOCUMENTS

| CN | 1066519 A | 11/1992 |
| EP | 1072679 A2 | 1/2001 |
| JP | H10234381 | 9/1998 |
| JP | 2002360247 A | 12/2002 |
| WO | WO-97/12896 A1 | 4/1997 |
| WO | WO-98/39352 A1 | 9/1998 |
| WO | WO-99/14226 A2 | 3/1999 |
| WO | WO-99/65928 | 12/1999 |
| WO | WO-00/47599 A1 | 8/2000 |
| WO | WO-00/56746 A2 | 9/2000 |
| WO | WO-00/56748 A1 | 9/2000 |
| WO | WO-00/66604 A2 | 11/2000 |

(Continued)

OTHER PUBLICATIONS

Singh, S.K. et al. "LNA (locked nucleic acids): synthesis and high-affinity nucleic acid recognition" Chem. Commun., vol. 4, p. 455-456 (Year: 1998).*
Output from the ftp address: ftp://ftp.ensembl.org/pub/current_human/data/ printed on Sep. 21, 2020. 1 page (Year: 2020).*
Adams et al., "Hindered Dialkylamino Nucleoside Phosphite Reagents in the Synthesis of Two DNA 51-Mers," J Am Chem Soc. 105:661-663 (1983).
Beaucage et al., "Deoxyneucleoside Phosphoramidites—A New Class of Key Intermediates for Deoxypolynucleotide Synthesis," Tetrahedron Lett 22: 1859-1862 (1981).
Butler. "Ensembl Gets A Wellcome Boost," Nature. 406(6794):333 (2000).
Caruthers et al., "Chemical Synthesis and Biological Studies on Mutated Gene-Control Regions," Cold Spring Harbor Symp Quant Biol. 47:411-418 (1983).

(Continued)

*Primary Examiner* — Stephen T Kapushoc
(74) *Attorney, Agent, or Firm* — Clark & Elbing LLP

(57) ABSTRACT

The invention relates to nucleic acid probes, nucleic acid probe libraries, and kits for detecting, classifying, or quantitating components in a complex mixture of nucleic acids, such as a transcriptome, and methods of using the same. The invention also relates to methods of identifying nucleic acid probes useful in the probe libraries and to methods of identifying a means for detection of a given nucleic acid.

17 Claims, 33 Drawing Sheets

Specification includes a Sequence Listing.

(56) References Cited

FOREIGN PATENT DOCUMENTS

| | | |
|---|---|---|
| WO | WO-01/00641 A1 | 1/2001 |
| WO | WO-01/07455 A1 | 2/2001 |
| WO | WO-02/10449 A2 | 2/2002 |
| WO | WO-03/20739 A2 | 3/2003 |
| WO | WO-03/039523 A2 | 5/2003 |

OTHER PUBLICATIONS

Causton, et al. "Remodeling of Yeast Genome Expression in Response to Environmental Changes," Mol Biol Cell. 12:323-337 (2001).
Communication from European Patent Application No. 04738926.7-2402, dated Apr. 21, 2010.
Communication from European Patent Application No. 04738926.7-2402, dated Jan. 15, 2010.
Communication from European Patent Application No. 04738926.7-2402, dated Jul. 6, 2009.
Communication from European Patent Application No. 04738926.7-2402, dated Mar. 21, 2006.
Communication from European Patent Application No. 04738926.7-2402, dated Nov. 2, 2007.
Communication from European Patent Application No. 04738926.7-2402, dated Sep. 11, 2009.
Cook, "Medical Chemistry of Antisense Oligonucleotides—Future Opportunities." Anti-Cancer Drug Design. 6:585-607 (1991).
Cummings et al., "Genomic BLAST: custom-defined virtual databases for complete and unfinished genomes," *FEMS Microbiology Letters* 216: 133-138 (2002).
De Mesmaeker et al., "Backbone Modifications in Oligonucleotides and Peptide Nucleic Acid Systems," Current Opinion in Structural Biology. 5:343-355 (1995).
Englisch et al., "Chemically Modified Oligonucleotides as Probes and Inhibitors," Angewandte Chemi, International Edition 30:613-629 (1991).
Fahlgren, "When small is better," Medicon Valley. 10-11 (2004).
First Office Action from Chinese Patent Application No. 200480022775.3, dated Dec. 21, 2007.
Freier et al., "The Ups and Downs of Nucleic Acid Suplex Stability: Structure-Stability Studies on Chemically-Modified SNA: RNA Duplexes," Nucleic Acid Research. 25:4429-4443 (1997).
Gall et al., "Formation and Detection of RNA-DNA Hybrid Molecules in Cytological Preparations," Proc Natl Acad Sci, USA. 63:378-383 (1969).
Hakansson et al,. "Convenient Synthesis of 7-Hydroxy-1-(hydroxymethyl)-3-(thymin-1-yl)-2, 5-dioxabicyclo[2.2.1]heptanes:alpha-L-Ribo-and-alpha-L-Xylo-Configured LNA Nucleosides," J Org Chem. 65(17):5161-5166 (2000).
Hakansson et al., "The Adenine Derivative of alpha-L-LNA (alpha-L-ribo Configured Locked Nucleic Acid): Synthesis and High-Affinity Hybridization Towards DNA, RNA, LNa and alpha-L-LNA Complementary Sequences." Bioorg Med Chem Lett. 11(7):935-938 (2001).
Herwig et al., "Information Theoretical Probe Selection for Hybridisation Experiments," Bioinformatics. 16:890-898 (2000).
Holstege et al., "Dissecting the Regulatory Circuitry of a Eukaryotic Genome." Cell. 95:717-728 (1998).
International Preliminary Report on Patentability for International Application No. PCT/DK2004/000429, dated Jan. 3, 2006.
International Search Report for International Application No. PCT/DK2004/00429, dated Mar. 2, 2005.
John et al., "RNA-DNA Hybrids at the Cytological Level," Nature. 223:582-587 (1996).
Koshkin et al., "A Simplified and Efficient Route to 2'-O. 4'-C-Methylene-Linked Bicyclic Ribonucleosides (Locked Nucleic Acid)." J Org Chem. 66(25):8504-8512 (2001).
Koshkin et al., "LNA (Locked Nucleic Acids): Synthesis of Adenine, Cytosine, Guanine, 5-Methylcytosine, Thymine, and Uracil Bicyclonucleoside Monomers, Olihgmerisation, and Unprecedented Nucleic Acid Recognition," Tetrahedron. 54:3607-30 (1998).

Kroschwitz (Ed.), Definition of Polynucleotides. *Concise Encyclopedia of Polymer Science and Engineering*. John Wiley & Sons, 858-859 (1990).
Kumar et al., "The First Analogues of LNA (Locked Nucleic Acids): Phosphorothioate-LNA and 2'-Thio-LNA," Bioorg Med Chem Lett. 8(16):2219-2222 (1998).
Kutyavin et al., "3'-Minor Groove Binder-DNA Probes Increase Sequence Specificity at PCR Extension Temperatures," Nucleic Acids Research. 28(2):655-661 (2000).
Kværnø et al., "Novel Bicyclic Nucleoside Analogue (1S, 5S, 6S)-6-Hydroxy-5-hydroxymethyl-1(uracil-1-yl)-3, 8-dioxabicuclo[3.2.1]octane: Synthesis and Incorporation into Oligofroxynucelotides," J Org Chem. 66(16):5498-5503 (2001).
Kværnø et al., "Synthesis of Abasic Locked Nucleic Acid and Two seco-LNA Derivatives and Evaluation of Their Hybridization Properties Compared with Their More Flexible DNA Counterparts." J Org Chem. 65(17): 5167-5176 (2000).
Latorra et al., "Design considerations and effects of LNA in PCR primers," *Mol Cell Probes*. 17: 253-259 (2003).
Letertre et al., "Evaluation of the Performance of LNA and MGB Probes in 5'-nuclease PCR assays," Molecular and Cellular Probes. 17:307-311 (2003).
Lodish et al., Chapter 7: Recombinant DNA Technology. *Molecular Cell Biology, Third Edition*. Scientific American Books, Inc., pp. 238-239 (1995).
Morita et al., "2'-O. 4'-C-Ethylene-Bridged Nucleic Acids (ENA): Highly Nuclease-Resistant and Thermodynamically Stable Oligonucleotides for Antisense Drug." Bioorg Med Chem Lett. 12(1): 73-76 (2002).
Office Action from Japanese Patent Application No. 2006-515724, dated Jun. 23, 2009.
Pfundheller et al., "Evaluation of Oligonucleotides Containing Two Novel 2'O-Methyl Modified Nucleotides Monomers: A 3'-C-Allyl and a 2'O, 3-C-Linked Bicyclic Derivative," Nucleosides & Nucleotides. 18(9):2017-2030 (1999).
Print out from the Registry database of compound having RN 433204-35-4 (2 pages).
RealTime ready Universal ProbeLibrary, "Redefining and revolutionizing real-time qPCR assays," Roche Applied Science. 2009. (1-32).
Response to Communication from European Patent Application No. 04738926.7-2402, dated Aug. 25, 2009.
Response to Communication from European Patent Application No. 04738926.7-2402, dated Feb. 6, 2008.
Response to Communication from European Patent Application No. 04738926.7-2402, dated Jan. 16, 2007.
Response to Communication from European Patent Application No. 04738926.7-2402, dated Mar. 25, 2010.
Response to Communication from European Patent Application No. 04738926.7-2402, dated Nov. 11, 2009.
Saiki et al., "Primer Directed Enzymatic Amplification of DNA with a Thermostable DNA Polymerase," Science. 239:487-491 (1988).
Sanghvi, Heterocyclic Base Modifications in Nucleic Acids and Their Applications in Antisense Oligonucleotides. *Antisense Research and Applications*. S.T. Crooke and B. Lebleu, Chapter 15 (1993).
Second Office Action from Chinese Patent Application No. 200480022775.3, dated Oct. 9, 2009.
Simeonov et al., "Single Nucleotide Polymorphism Genotyping Using Short, Fluorescently Labled Locked Nucleic Acid (LNA) Probes and Fluorescence Polarization Detection," Nucleic Acids Research. 30(17): e19 (2002).
Sinha et al., "β-Cyanoethyl N, N-Dialkylamino/N-Morpholinomonochloro Phosphoamidites, New Phosphitylating Agents Facilitating Ease of Deprotection and Work-Up of Synthesized Oligonucleotides." Tetrahedron Lett. 24:5843-5846 (1983).
STN Sequence Search Results, 1-18.
TaqMan Gene Expression Assay Products, "TaqMan gene expression assays," Product Guide. Applied Biosystems. Sep. 2005. (1-13).
Tyagi et al., "Molecular Beacons: Probes that Flouresce Upon Hybridization," Nat Biotechnol. 14:303-308 (1996).
Wahlestedt et al., "Potent and Nontoxic Antisense Oligonucleotides Containing Locked Nucleic Acids," Proc Natl Acad Sci USA. 97:5633-5638 (2000).

(56) References Cited

OTHER PUBLICATIONS

Written Opinion of the International Searching Authority for International Application No. PCT/DK2004/000429, dated Mar. 2, 2005.

* cited by examiner

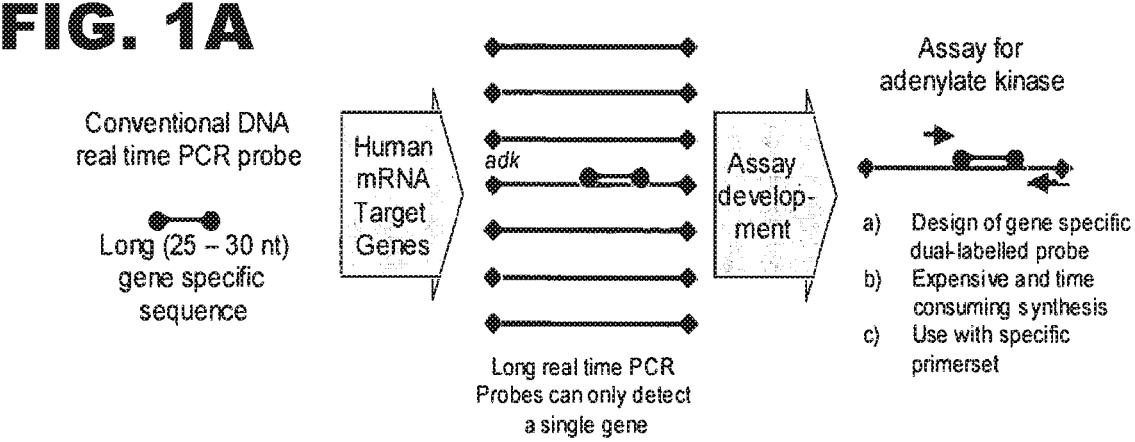
FIG. 1A
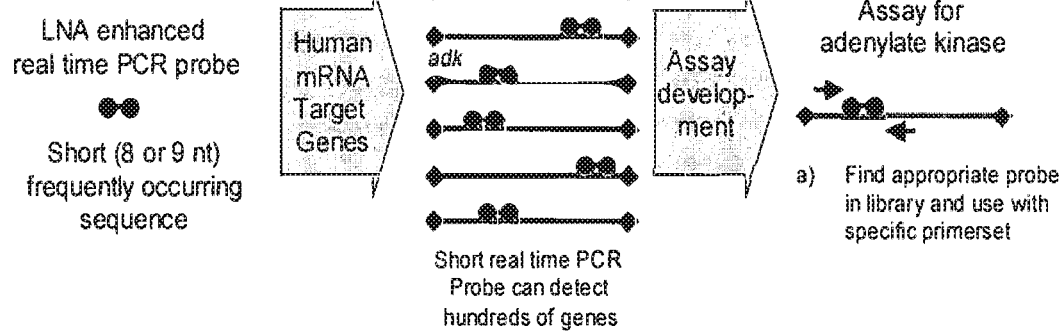
FIG. 1B
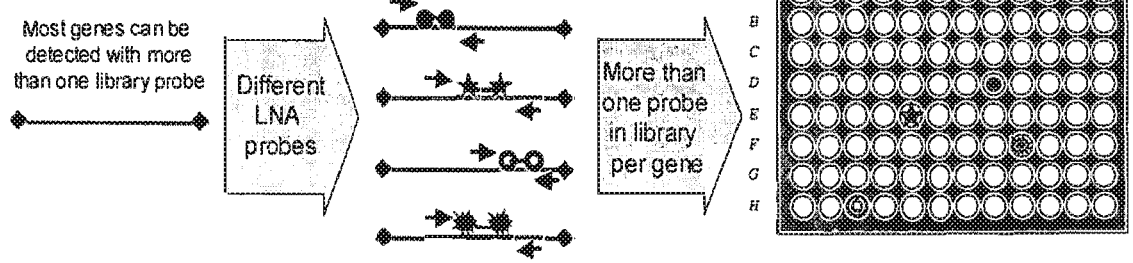

| # | Seq | Name | # | Seq | Name |
|---|---|---|---|---|---|
| 1 | ctcctcct | Lib_hum_A_005 | 42 | cttctccc | Lib_hum_B_127 |
| 2 | ctggagga | Lib_hum_A_007 | 43 | cctcagcc | Lib_hum_C_202 |
| 3 | aggagctg | Lib_hum_B_101 | 44 | ctccttcc | Lib_hum_C_246 |
| 4 | cagcctgg | Lib_hum_A_008 | 45 | cagcaggc | Lib_hum_C_203 |
| 5 | cagcagcc | Lib_hum_A_009 | 46 | ctgcctct | Lib_hum_C_204 |
| 6 | tgctggag | Lib_hum_A_010B | 47 | ctccacct | Lib_hum_C_205 |
| 7 | agctggag | Lib_hum_A_019 | 48 | ctcctccc | Lib_hum_C_206 |
| 8 | ctgctgcc | Lib_hum_A_020 | 49 | cttcccca | Lib_hum_C_207 |
| 9 | aggagcag | Lib_hum_A_011B | 50 | cttcagcc | Lib_hum_C_208 |
| 10 | ccaggagg | Lib_hum_A_016 | 51 | ctctgcca | Lib_hum_C_209 |
| 11 | tcctgctg | Lib_hum_B_102 | 52 | ctgggaga | Lib_hum_C_247 |
| 12 | cttcctcc | Lib_hum_A_015 | 53 | cttctgcc | Lib_hum_C_210 |
| 13 | ccgccgcc | Lib_hum_A_004 | 54 | cagcaggt | Lib_hum_C_211 |
| 14 | cctggagc | Lib_hum_B_103 | 55 | tctggagc | Lib_hum_C_214 |
| 15 | cagcctcc | Lib_hum_A_017 | 56 | tcctgctc | Lib_hum_C_248 |
| 16 | tggctgtg | Lib_hum_A_021 | 57 | ctggggcc | Lib_hum_C_220 |
| 17 | cctggaga | Lib_hum_A_022 | 58 | ctcctgcc | Lib_hum_C_219 |
| 18 | ccagccag | Lib_hum_B_105 | 59 | ctgggcaa | Lib_hum_C_223 |
| 19 | ccagggcc | Lib_hum_A_023 | 60 | ctggggct | Lib_hum_C_226 |
| 20 | cccagcag | Lib_hum_B_106 | 61 | tggtggcc | Lib_hum_C_225 |
| 21 | ccaccacc | Lib_hum_A_025 | 62 | ccagggca | Lib_hum_C_240 |
| 22 | ctcctcca | Lib_hum_B_104 | 63 | ctgctccc | Lib_hum_C_227 |
| 23 | ttctcctg | Lib_hum_B_109 | 64 | tgggcagc | Lib_hum_C_239 |
| 24 | cagcccag | Lib_hum_B_110 | 65 | ctccatcc | Lib_hum_C_222 |
| 25 | ctggctgc | Lib_Hum_A_001 | 66 | ctgcccca | Lib_hum_C_215 |
| 26 | ctccacca | Lib_hum_B_112 | 67 | ttcctggc | Lib_hum_C_244 |
| 27 | cttcctgc | Lib_hum_B_111 | 68 | atggctgc | Lib_hum_C_217 |
| 28 | cttccagc | Lib_hum_B_114 | 69 | tggtggaa | Lib_hum_C_231 |
| 29 | ccacctcc | Lib_hum_B_121 | 70 | tgctgtcc | Lib_hum_C_228 |
| 30 | ttcctctg | Lib_hum_B_122 | 71 | ccagccgc | Lib_hum_C_224 |
| 31 | cccagccc | Lib_hum_B_116 | 72 | catccagc | Lib_hum_C_216 |
| 32 | tggtgatg | Lib_hum_B_124 | 73 | tcctctcc | Lib_hum_C_229 |
| 33 | tggctctg | Lib_hum_B_123 | 74 | agctggga | Lib_hum_C_233 |
| 34 | ctgccttc | Lib_hum_B_118 | 75 | ctggtctc | Lib_hum_C_234 |
| 35 | ctccagcc | Lib_hum_B_119 | 76 | ttcccagt | Lib_hum_C_235 |
| 36 | tgtggctg | Lib_hum_B_125 | 77 | caggcagc | Lib_hum_C_250 |
| 37 | cagaggag | Lib_hum_A_048B | 78 | cctcagc | Lib_hum_C_245 |
| 38 | cagctccc | Lib_hum_B_129 | 79 | ctggctcc | Lib_hum_C_241 |
| 39 | ctgcctcc | Lib_hum_B_128 | 80 | tcctcttct | Lib_hum_C_236 |
| 40 | tctgctgc | Lib_hum_C_242 | 81 | tccagtgt | Lib_hum_C_237 |
| 41 | ctgcttcc | Lib_hum_C_201 | 82 | acagcctca | GAPDH_AQQ1 |
| | | | 83 | cagccacc | Lib_hum_C_243 |

Fig. 13

| | | |
|---|---|---|
| 84 | cttctggc | Lib_hum_D_301 |
| 85 | tccactgc | Lib_hum_D_302 |
| 86 | ctctgcgt | Lib_hum_D_303 |
| 87 | ctggaggc | Lib_hum_D_304 |
| 88 | ctggaagc | Lib_hum_D_305 |
| 89 | ctgccacc | Lib_hum_D_306 |
| 90 | tccaggtc | Lib_hum_D_307 |
| 91 | cagcatcc | Lib_hum_D_308 |
| 92 | cagaggct | Lib_hum_D_309 |
| 93 | ctgaagcc | Lib_hum_D_310 |
| 94 | tgcagggc | Lib_hum_D_311 |
| 95 | atggcagc | Lib_hum_D_312 |
| 96 | catcctcc | Lib_hum_D_313 |
| 97 | ctctgcct | Lib_hum_D_314 |
| 98 | ccagtgcc | Lib_hum_D_315 |
| 99 | cagtggca | Lib_hum_D_316 |
| 100 | actgctgc | Lib_hum_D_317 |
| 101 | cagcaccc | Lib_hum_D_318 |
| 102 | atgatggc | Lib_hum_D_319 |
| 103 | ccaggagc | Lib_hum_D_320 |

Fig. 14

| | Name | Sequence |
|---|---|---|
| 14590 | Lib_hum_A_con1_target | cacccgttcggcatatccatatttcccacagccaccaccagaggaagcagcaggagcagcctcct<br>cagagaagcagcctgagagcttcctccagctccaggcccgcctgttgagcagcagcaccagaagag<br>ggggagttacggttggttgtacga |
| 14778 | Long mere 001-015-sense (Hum Lib A 001-014) | tggcgacgcacacccgcttacccctgctgaggaagctgaggaggagcagcctgagcagcagccag<br>ctccgccgccaggaagccgactcacggccacgcatta |
| 14779 | Long mere 016-026-antisense (Hum Lib A 016-026, 011, 048) | gggtgcaccgtgagtcaatggctcccaggaggctgtcttctggtgctgctcctctgctcctccagctt<br>ctctgccctgttggtgctggtaatgctgtgccgtagtc |
| 15315 | Long mere B1a-sense | attgactcacggtcgccacccaacctgctgggctgccctgaagcttccaggagaacttcagccagctcct<br>ccaccacaaggaagaataaccgtgaacgcgtcat |
| 15316 | Long mere B1b-antisense | ataccacatccaaggcgtcctaaggaggcaggaaggagagctgccttccccagcccttctcccagcaca<br>gcagacagagcaccctccaccaaaatgaccgcgttccacggtta |
| 15317 | Long mere B2a-sense | attgactcacggtcgcacgcagcacatctcccagaggcagaggaactgcctcctccaccatcaccactgctgggct<br>gggaagcttccaggcgtccctaacttctcccagagaaaatgacggcgttccacggtcat |
| 15318 | Long mere B2b-antisense | ataccacatccaaggcgtcctgagcagccacctcccagagcccagccagccaccagccacaccagagcaggaa<br>ggagctgcctcacggtcgcacaggcagctccttcctgctgaaaataccgttccacggtta |
| 15319 | Long mere B3a-sense | attgactcacggtcgcacgacaggcagctccaggagcgtcctaacttccaggcagctccctgccgagagccagcccc<br>gaaggaggagcagctccaggagcgtccctaacttccaggcagctcccttccagcccagctc |
| 15320 | Long mere B3b-antisense | ataccacatccaaggcacagcagccaccagcagccaaattgccaccaatgtcctctgagctcccagct<br>ctcccacccaggcagctccacggcgtccggtca |
| 15430 | Long mere E1 – sense | ttaggagcgcttgatgtgtatggtgggtgaggcggtcgcgtcctgcatcctccttctgcctctgtccccagc<br>tgagccatgcctgcccgcttccaccaattgccgacccaccggata |
| 15431 | Long mere F1 – antisense | Attcgctacggcccaacacttactccagtgggcagcatccagcaggccaccatatcccggtggtcggcagt<br>gtctggagctgcctcccagtgggcagcatccagcaggccaccatatcccggtggtcggcaat |
| 15432 | Long mere G1 – sense | taggtgttggccgtagcgaatcgctctgccact–<br>gggcctggtctccatcctctcccctggcaacctgctgtccttggcagt-<br>gggaacctgtgccaattgtcctccgccgcgtgactcat |
| 15433 | Long mere E2 – sense | ttaggagcgcttgatggtatctctgccactggctccagatcctcttctgccccact–<br>gccatggcagctgggcagctctcctcccccaattgcccgaccccaggata |
| 15434 | Long mere F2-antisense | attcgctacgaccaacaccttacctcagccccagctccttccaccaccgccgcccaag–<br>gactggctcctgcctgccctggcaactgggaatgctgcctcttcacgccgctcttccaccaatccccgcgtgggtcggccatc- |
| 15435 | Long mere G2 – sense | taagtgttgccaggagaggacagtggcacaggtggcacacaggccaccaattgtcctccgcgccgactcat<br>cagtgtgcaggagaggacagtggcacaggtggcacacaggccaccaattgtcctccgccgccgactcat |

Fig. 15 qPCR for human genes made easy.

The design of an efficient and reliable qPCR assay for a human gene is a complex task. We here present the ProbeFinder (see www.probelibrary.com) a new web tool for fast and easy selection of ProbeLibrary™ probes and the design of primers for qPCR of human genes.

The ProbeFinder web server designs optimal qPCR probes and primers fast and reliably for any given human gene. Alternative solutions for genes with special requirements are presented on easy to use web pages.

ProbeFinder designs the optimal qPCR in three steps.

Determine intron positions

Noise from chromosomal DNA* is eliminated by selecting intron-spanning qPCR's. Introns are determined by a blast search against the human genome. Regions found on the DNA, but not in the transcript are considered to be introns.

* The intron prediction can be deselected for qPCR's that are free from chromosomal DNA.

Match ProbeLibrary™ to gene

Virtually all human transcripts* are covered by at least one of the 90 ProbeLibrary™ probes. The high coverage is made possible using the LNA™ technology of Exiqon. The matching probe is identified by ProbeFinder™ within seconds.

* A human transcript from RefSeq is on average covered by 17 ProbeLibrary™ probes and each probe is on average found in more than 7000 of the 38556 transcripts.

Design primers and select optimal qPCR assay

Primers are designed with Primer3. Finally the assays are ranked according to carefully selected rules ensuring the best possible qPCR assay. The rules favour intron spanning amplicons to remove false signals from DNA contamination, small amplicon size for reproducible and comparable assays and a GC content optimised for PCR.

Fig. 16

*Listing of program modules*

*Program main.aap*

```
CC = gcc -DLIB -O2
SOURCE =
    getcover.c
    dyp.c
    getopt.c
    getopt1.c
    getopt_init.c
LIBS = -lm TARGET = getcover$EXESUF
```

Fig. 17A

```
Program dyp.h
/*AUTHOR
        Copyright Niels Tolstrup 2003
        Exiqon
*/ typedef struct sequences_t {
        int     nseq;
        int     maxnseq;
        char    **seqs;
} sequences_type;

typedef struct score_rec_t {
        int     alph_len;
        int     gap_start;
        int     gap_cont;
        int     mismatch_cont;
        int     loop_score;
        int     match_cont_factor;
        int     match_threshold;
        int     min_strong_ident_score;
        int     min_ident_score;
        int     min_sim_score;
        char    *alph;
        int     *mat;
} score_rec_type;

typedef struct param_t {
        char    *alph;
        int     *mathyp;
        int     depth;
        int     global;
        int     min_score;
        int     max_res;
        sequences_type *seqs;
        sequences_type *seqs2;
        score_rec_type *score_rec;
} param_type;

typedef struct dynamic_str_t {
        int     len;
        int     maxlen;
        char    *s;
} dynamic_str_type;

param_type *init();

char *empty_str( int len );

char *make_nmer( long number, int n_mer, char *alph );

dynamic_str_type *new_dynamic_str_type();

dynamic_str_type *addchar( dynamic_str_type *seq, int c );

long n_mer( int n_mer, char *alph );

long reverse_dna( long n, int oligolen );

long comp_dna( long n, int oligolen );

long rev_comp_dna( long n, int oligolen ).
```

Fig. 17B

*Program getcover.c*

```
        /*
        *$Id: $
  5     SYNOPSIS
                  getcover -l 9 -p -f < h_sap.fasta > h_sap_19.ncat
                  getcover -l 9 -i 1 -d 10 -t 60 -c -n -m -s < h_sap_19.stat >
        h_sap_19.cover 10     DESCRIPTION
                  Find a cover of n mers for human transcriptoms
                  Input: A fasta file
                  Options: getcover --help
 15     INSTALATION
                  The program works udner solaris and linux.

20     AUTHOR
                  Copyright Niels Tolstrup 2003
                  Exiqon
        */
 25
        #include <stdio.h>      /* fprintf, rand..*/
        #include <stdlib.h>     /* calloc..       */
        #include <stdarg.h>     /* va_list..      */
        #include <string.h>     /* strlen..       */
 30     #include <limits.h>     /* USHRT_MAX..    */
        #include <math.h>       /* pow            */
        #include <ctype.h>      /* tolower        */
        #include <time.h>       /* clock          */
        #include "dyp.h"        /* make_nmer..    */
 35     #include "getopt.h"     /* getopt_long    */

/*********** GLOBAL VARIABLES ****************/

40     #ifdef NODYP
        int             verbose = 0;
        char*           program_name;
        #else
        extern int verbose;
 45     extern char* program_name;
        #endif int             t_start;
 50     int             t_lap1;
        int             t_lap2;
        int             t_run;
        int             t_debug;
        int             t_last_debug;
 55     int             t_debug_interval = 5;

/*** these should not be global ***/

60     #define TIME_INIT  0
        #define LAP_TIME   1
        #define TOTAL_TIME 2
        #define DEBUG_TIME 4

65
        /********* STRUCTURES ******************/ typedef struct alph_t {
 70             char            *name;
                char            *alph;
                int             len;
        } alph_type;

75     typedef struct lna_t {
                long            lna_id;
                char            self_score;
                char            target_score;
 80             char            tm;
        } lna_type;

typedef struct nmer_t {
 85             int             nmer_id;
                short           selected;
                char            ok;      /* ==0:undefined,<0:discard,>0:ok
        */
                lna_type        *lna;
 90             int             n_total_gene;
                int             n_gene;
                int             max_n_gene;
                int             *gene;
        } nmer_type;
 95
        typedef struct stat_t {
                int             n_nmer;
                int             oligolen;
100             alph_type       *alph;
                int             max_n_nmer;
                char            compact;
                nmer_type       **nmer;
                int             n_gene;
105             int             max_n_gene;
                int             *gene;
        } stat_type;

110     typedef struct conf_t {
                int             fasta_in;
                int             stat_in;
                int             oligolen;
                float           max_gene_hit_frac;
115             int             max_gene_hit;
                int             target_minus_self;
                int             target_min_temp;
                int             complement_flag;
                int             max_select;
```

```
120             int             no_5end_spike;
                int             max_product;
        } conf_type;

125     #ifdef NODYP
        void die( char *fmt, ...){
                va_list ap;
                fprintf( stderr, "Uhoh: ");
                va_start( ap, fmt);
130             vfprintf( stderr, fmt, ap);
                va_end( ap);
                fprintf( stderr, "\n");
                exit( 1);
        }
135     #endif void print_debug( char *fmt, ...){
                va_list ap;
140             if( verbose >= 3) {
                    va_start( ap, fmt);
                    vfprintf( stderr, fmt, ap);
                    va_end( ap);
                    fprintf( stderr, "\n");
145                 fflush( stderr);
                }
        }

150     void print_debug_interval( char *fmt, ...){
                va_list ap;
                if( (verbose >= 3) && run_time( DEBUG_TIME)) {
                    fprintf( stderr, "%8d ", t_run);
                    va_start( ap, fmt);
155                 vfprintf( stderr, fmt, ap);
                    va_end( ap);
                    fprintf( stderr, "\n");
                    fflush( stderr);
                }
160     } void usage( char *fmt, ...){
                va_list ap;
165             va_start( ap, fmt);
                vfprintf( stderr, fmt, ap);
                va_end( ap);
                fprintf( stderr,
                "\nUsage: getcover -h,--help\n"
170             "       -v,--verbose\n"
                "       -vv,--verbose --verbose\n"
                "       -l,--oligo_len len\n"
                "       -i,--max_gene_hit_frac fraction\n"
                "       -d,--target_minus_self delta\n"
175             "       -t,--target_min_temp temp\n"
                "       -c,--complement\n"
                "       -m,--max_product\n"
                "       -n,--no_5end_spike\n"
                "       -f,--fasta_in\n"
180             "       -s,--stat_in\n"
                "       -p,--dump_stat\n"
                "\n"
                "DESCRIPTION\n"
                "       ");
185             fprintf( stderr, "\n");
                exit( 1);
        }

190     int run_time( int type){
                if( type == DEBUG_TIME) {
                    t_debug = clock()/CLOCKS_PER_SEC;
                    if( t_debug - t_last_debug >= t_debug_interval ) {
                        t_run = t_debug - t_start;
195                     t_last_debug = t_debug;
                    }
                    else
                        t_run = 0;
                }
200             else if( type == TIME_INIT) {
                    t_start     = clock()/CLOCKS_PER_SEC;
                    t_lap1      = t_start;
                    t_last_debug = t_start;
                    t_run       = 0;
205             }
                else if( type == LAP_TIME) {
                    t_lap2   = clock()/CLOCKS_PER_SEC;
                    t_run    = t_lap2 - t_lap1;
                    t_lap1   = t_lap2;
210             }
                else if( type == TOTAL_TIME) {
                    t_lap1   = clock()/CLOCKS_PER_SEC;
                    t_run    = t_lap1 - t_start;
                }
215             return t_run;
        } ifdef NODYP
220     void *xalloc( int nobj, int size){
                void *mem;
                /*mem =        calloc( nobj, size);*/
                mem = malloc( nobj * size);
                /*printf( "calloc: allocating %d objects of size %d bytes\n", nobj,
225             size);*/
                if( mem == NULL){
                    die( "Could not allocate %d x %d bytes\n", nobj, size);
                }
                return mem;
230     }
        #endif void free_nmer_type( nmer_type *nmer) {
235             if( nmer != NULL ) {
                    free( nmer->gene);
                    free( nmer->lna);
                }
                free( nmer);
```

```
        usage( "please select a method: u, a or y");

2640    for( i=0; i<param->seqs->nseq; i++) {
            fprintf( outfile, ">sequence_%03d\n", i+1);
            if(    algo & SECONDARY_STRUCTURE )
                nussinov( outfile, param, param->seqs->seqs[i]);
            if( algo & SELF_ANEALING ) {
2645            rev_seq       = calloc( strlen( param->seqs->seqs[i])
        + 1, sizeof( char));
                strcpy(       rev_seq, param->seqs->seqs[i]);
                reverse( rev_seq);
                if( param->min_score < 2 ) {
2650                param->min_score = 2;
                }
                align( outfile, param, param->seqs->seqs[i], rev_seq);
                free( rev_seq);
            }
2655        if( algo & TM ) {
                rev_seq       = calloc( strlen( param->seqs->seqs[i])
        + 1, sizeof( char));
                strcpy(       rev_seq, param->seqs->seqs[i]);
                lower( rev_seq);
2660            comp( rev_seq);
                if( param->min_score < 2 ) {
                    param->min_score = 2;
                }
                align( outfile, param, param->seqs->seqs[i], rev_seq);
2665            free( rev_seq);
            }
            if( algo & HYBRIDIZATION ) {
                if( param->seqs2->seqs[i] == NULL)
                    die( "Sequence 2 is missing");
2670            rev_seq       = calloc( strlen( param->seqs2->seqs[i])
        + 1, sizeof( char));
                strcpy(       rev_seq, param->seqs2->seqs[i]);
                reverse( rev_seq);
                align( outfile, param, param->seqs->seqs[i], rev_seq);
2675            free( rev_seq);
            }
        }
        }
        fclose( outfile);
2680
        free_param_type( param);

return 0;
        }
2685    #endif
```

Fig. 17T

PROBES, LIBRARIES AND KITS FOR ANALYSIS OF MIXTURES OF NUCLEIC ACIDS AND METHODS FOR CONSTRUCTING THE SAME

SEQUENCE LISTING

The instant application contains a Sequence Listing which has been submitted electronically in ASCII format and is hereby incorporated by reference in its entirety. Said ASCII copy, created Mar. 22, 2021, is named 50287-012003 Sequence Listing 3 22 21 ST25.txt and is 104,806,341 bytes in size.

FIELD OF THE INVENTION

The invention relates to nucleic acid probes, nucleic acid probe libraries, and kits for detecting, classifying, or quantitating components in a complex mixture of nucleic acids, such as a transcriptome, and methods of using the same.

BACKGROUND OF THE INVENTION

With the advent of microarrays for profiling the expression of thousands of genes, such as GeneChip™ arrays (Affymetrix, Inc., Santa Clara, Calif.), correlations between expressed genes and cellular phenotypes may be identified at a fraction at the cost and labor necessary for traditional methods, such as Northern- or dot-blot analysis. Microarrays permit the development of multiple parallel assays for identifying and validating biomarkers of disease and drug targets which can be used in diagnosis and treatment. Gene expression profiles can also be used to estimate and predict metabolic and toxicological consequences of exposure to an agent (e.g., such as a drug, a potential toxin or carcinogen, etc.) or a condition (e.g., temperature, pH, etc).

Microarray experiments often yield redundant data, only a fraction of which has value for the experimenter. Additionally, because of the highly parallel format of microarray-based assays, conditions may not be optimal for individual capture probes. For these reasons, microarray experiments are most often followed up by, or sequentially replaced by, confirmatory studies using single-gene homogeneous assays. These are most often quantitative PCR-based methods such as the 5' nuclease assay or other types of dual labelled probe quantitative assays. However, these assays are still time-consuming, single-reaction assays that are hampered by high costs and time-consuming probe design procedures. Further, 5' nuclease assay probes are relatively large (e.g., 15-30 nucleotides). Thus, the limitations in homogeneous assay systems currently known create a bottleneck in the validation of microarray findings, and in focused target validation procedures.

An approach to avoid this bottleneck is to omit the expensive dual-labelled indicator probes used in 5' nuclease assay procedures and molecular beacons and instead use non-sequence-specific DNA intercalating dyes such as SYBR Green that fluoresce upon binding to double-stranded but not single-stranded DNA. Using such dyes, it is possible to universally detect any amplified sequence in real-time. However, this technology is hampered by several problems. For example, nonspecific priming during the PCR amplification process can generate unintentional non-target amplicons that will contribute in the quantification process. Further, interactions between PCR primers in the reaction to form "primer-dimers" are common. Due to the high concentration of primers typically used in a PCR reaction, this can lead to significant amounts of short double-stranded non-target amplicons that also bind intercalating dyes. Therefore, the preferred method of quantitating mRNA by real-time PCR uses sequence-specific detection probes.

One approach for avoiding the problem of random amplification and the formation of primer-dimers is to use generic detection probes that may be used to detect a large number of different types of nucleic acid molecules, while retaining some sequence specificity has been described by Simeonov, et al. (*Nucleic Acid Research* 30(17): 91, 2002; U.S. Patent Publication 20020197630) and involves the use of a library of probes comprising more than 10% of all possible sequences of a given length (or lengths). The library can include various non-natural nucleobases and other modifications to stabilize binding of probes/primers in the library to a target sequence. Even so, a minimal length of at least 8 bases is required for most sequences to attain a degree of stability that is compatible with most assay conditions relevant for applications such as real time PCR. Because a universal library of all possible 8-mers contains 65,536 different sequences, even the smallest library previously considered by Simeonov, et al. contains more than 10% of all possibilities, i.e. at least 6554 sequences which is impractical to handle and vastly expensive to construct.

From a practical point of view, several factors limit the ease of use and accessibility of contemporary homogeneous assays applications. The problems encountered by users of conventional assay technologies include:

prohibitively high costs when attempting to detect many different genes in a few samples, because the price to purchase a probe for each transcript is high.

the synthesis of labelled probes is time-consuming and often the time from order to receipt from manufacturer is more than 1 week.

User-designed kits may not work the first time and validated kits are expensive per assay.

it is difficult to quickly test for a new target or iteratively improve probe design.

the exact probe sequence of commercial validated probes may be unknown for the customer resulting in problems with evaluation of results and suitability for scientific publication.

When assay conditions or components are obscure it may be impossible to order reagents from alternative source.

The described invention address these practical problems and aim to ensure rapid and inexpensive assay development of accurate and specific assays for quantification of gene transcripts.

SUMMARY OF THE INVENTION

It is desirable to be able to quantify the expression of most genes (e.g., >98%) in e.g. the human transcriptome using a limited number of oligonucleotide detection probes in a homogeneous assay system. The present invention solves the problems faced by contemporary approaches to homogeneous assays outlined above by providing a method for construction of generic multi-probes with sufficient sequence specificity—so that they are unlikely to detect a randomly amplified sequence fragment or primer-dimers—but are still capable of detecting many different target sequences each. Such probes are usable in different assays and may be combined in small probe libraries (50 to 500 probes) that can be used to detect and/or quantify individual components in complex mixtures composed of thousands of different nucleic acids (e.g. detecting individual transcripts in the human transcriptome composed of >30,000 different nucleic acids.) when combined with a target specific primer set.

Each multi-probe comprises two elements: 1) a detection element or detection moiety consisting of one or more labels to detect the binding of the probe to the target; and 2) a recognition element or recognition sequence tag ensuring the binding to the specific target(s) of interest. The detection element can be any of a variety of detection principles used in homogeneous assays. The detection of binding is either direct by a measurable change in the properties of one or more of the labels following binding to the target (e.g. a molecular beacon type assay with or without stem structure) or indirect by a subsequent reaction following binding (e.g. cleavage by the 5' nuclease activity of the DNA polymerase in 5' nuclease assays).

The recognition element is a novel component of the present invention. It comprises a short oligonucleotide moiety whose sequence has been selected to enable detection of a large sub-set of target nucleotides in a given complex sample mixture. The novel probes designed to detect many different target molecules each are referred to as multi-probes. The concept of designing a probe for multiple targets and exploit the recurrence of a short recognition sequence by selecting the most frequently encountered sequences is novel and contrary to conventional probes that are designed to be as specific as possible for a single target sequence. The surrounding primers and the choice of probe sequence in combination subsequently ensures the specificity of the multi-probes. The novel design principles arising from attempts to address the largest number of targets with the smallest number of probes are likewise part of the invention. This is enabled by the discovery that very short 8-9 mer LNA mix-mer probes are compatible with PCR based assays. In one aspect of the present invention modified or analogue nucleobases, nucleosidic bases or nucleotides are incorporated in the recognition element, possibly together with minor groove binders and other modifications, that all aim to stabilize the duplex formed between the probe and the target molecule so that the shortest possible probe sequence with the widest range of targets can be used. In a preferred aspect of the invention the modifications are incorporation of LNA residues to reduce the length of the recognition element to 8 or 9 nucleotides while maintaining sufficient stability of the formed duplex to be detectable under ordinary assay conditions.

Preferably, the multi-probes are modified in order to increase the binding affinity of the probe for a target sequence by at least two-fold compared to a probe of the same sequence without the modification, under the same conditions for detection, e.g., such as PCR conditions, or stringent hybridization conditions. The preferred modifications include, but are not limited to, inclusion of nucleobases, nucleosidic bases or nucleotides that has been modified by a chemical moiety or replaced by an analogue (e.g. including a ribose or deoxyribose analogue) or by using internucleotide linkages other than phosphodiester linkages (such as non-phosphate internucleotide linkages), all to increase the binding affinity. The preferred modifications may also include attachment of duplex stabilizing agents e.g., such as minor-groove-binders (MGB) or intercalating nucleic acids (INA). Additionally the preferred modifications may also include addition of non-discriminatory bases e.g., such as 5-nitroindole, which are capable of stabilizing duplex formation regardless the nucleobase at the opposing position on the target strand. Finally, multi-probes composed of a non-sugar-phosphate backbone, e.g. such as PNA, that are capable of binding sequence specifically to a target sequence are also considered as modification. All the different binding affinity increased modifications mentioned above will in the following be referred to as "the stabilizing modification(s)", and the ensuing multi-probe will in the following also be referred to as "modified oligonucleotide". More preferably the binding affinity of the modified oligonucleotide is at least about 3-fold, 4-fold, 5-fold, or 20-fold higher than the binding of a probe of the same sequence but without the stabilizing modification(s).

Most preferably, the stabilizing modification(s) is inclusion of one or more LNA nucleotide analogs. Probes of from 6 to 12 nucleotides according to the invention may comprise from 1 to 8 stabilizing nucleotides, such as LNA nucleotides. When at least two LNA nucleotides are included, these may be consecutive or separated by one or more non-LNA nucleotides. In one aspect, LNA nucleotides are alpha and/or xylo LNA nucleotides.

The invention also provides oligomer multi-probe library useful under conditions used in NASBA based assays.

NASBA is a specific, isothermal method of nucleic acid amplification suited for the amplification of RNA. Nucleic acid isolation is achieved via lysis with guanidine thiocyanate plus Triton X-100 and ending with purified nucleic acid being eluted from silicon dioxide particles. Amplification by NASBA involves the coordinated activities of three enzymes, AMV Reverse Transcriptase, RNase H, and T7 RNA Polymerase. Quantitative detection is achieved by way of internal calibrators, added at isolation, which are co-amplified and subsequently identified along with the wild type of RNA using electro chemiluminescence.

The invention also provides an oligomer multi-probe library comprising multi-probes comprising at least one with stabilizing modifications as defined above. Preferably, the probes are less than about 20 nucleotides in length and more preferably less than 12 nucleotides, and most preferably about 8 or 9 nucleotides. Also, preferably, the library comprises less than about 3000 probes and more preferably the library comprises less than 500 probes and most preferably about 100 probes. The libraries containing labelled multi-probes may be used in a variety of applications depending on the type of detection element attached to the recognition element. These applications include, but are not limited to, dual or single labelled assays such as 5' nuclease assay, molecular beacon applications (see, e.g., Tyagi and Kramer Nat. Biotechnol. 14: 303-308, 1996) and other FRET-based assays.

In one aspect of the invention the multi-probes described above, are designed together to complement each other as a predefined subset of all possible sequences of the given lengths selected to be able to detect/characterize/quantify the largest number of nucleic acids in a complex mixture using the smallest number of multi-probe sequences. These pre-designed small subsets of all possible sequences constitute a multi-probe library. The multi-probe libraries described by the present invention attains this functionality at a greatly reduced complexity by deliberately selecting the most commonly occurring oligomers of a given length or lengths while attempting to diversify the selection to get the best possible coverage of the complex nucleic acid target population. In one preferred aspect, probes of the library hybridize with more than about 60% of a target population of nucleic acids, such as a population of human mRNAs. More preferably, the probes hybridize with greater than 70%, greater than 80%, greater than 90%, greater than 95% and even greater than 98% of all target nucleic acid molecules in a population of target molecules (see, e.g., FIG. 1).

In a most preferred aspect of the invention, a probe library (i.e. such as about 100 multi-probes) comprising about 0.1% of all possible sequences of the selected probe length(s), is capable of detecting, classifying, and/or quantifying more than 98% of mRNA transcripts in the transcriptome of any specific species, particulary mammals and more particular humans (i.e., >35,000 different mRNA sequences). In fact, it is preferred that at least 85% of all target nucleic acids in a target population are covered by a multi-probe library of the invention.

The problems with existing homogeneous assays mentioned above are addressed by the use of a multi-probe library according to the invention consisting of a minimal set of short detection probes selected so as to recognize or detect a majority of all expressed genes in a given cell type from a given organism. In one aspect, the library comprises probes that detect each transcript in a transcriptome of greater than about 10,000 genes, greater than about 15,000 genes, greater than about 20,000 genes, greater than about 25,000 genes, greater than about 30,000 genes or greater than about 35,000 genes or equivalent numbers of different mRNA transcripts. In one preferred aspect, the library comprises probes that detect mammalian transcripts sequences, e.g., such as mouse, rat, rabbit, monkey, or human sequences.

By providing a cost efficient multi-probe set useful for rapid development of quantitative real-time and end-point PCR assays, the present invention overcomes the limitations discussed above for contemporary homogeneous assays. The detection element of the multi-probes according to the invention may be single or doubly labelled (e.g. by comprising a label at each end of the probe, or an internal position). Thus, probes according to the invention can be adapted for use in 5' nuclease assays, molecular beacon assays, FRET assays, and other similar assays. In one aspect, the detection multi-probe comprises two labels capable of interacting with each other to produce a signal or to modify a signal, such that a signal or a change in a signal may be detected when the probe hybridizes to a target sequence. A particular aspect is when the two labels comprise a quencher and a reporter molecule.

In another aspect, the probe comprises a target-specific recognition segment capable of specifically hybridizing to a plurality of different nucleic acid molecules comprising the complementary recognition sequence. A particular detection aspect of the invention referred to as a "molecular beacon with a stem region" is when the recognition segment is flanked by first and second complementary hairpin-forming sequences which may anneal to form a hairpin. A reporter label is attached to the end of one complementary sequence and a quenching moiety is attached to the end of the other complementary sequence. The stem formed when the first and second complementary sequences are hybridized (i.e., when the probe recognition segment is not hybridized to its target) keeps these two labels in close proximity to each other, causing a signal produced by the reporter to be quenched by fluorescence resonance energy transfer (FRET). The proximity of the two labels is reduced when the probe is hybridized to a target sequence and the change in proximity produces a change in the interaction between the labels. Hybridization of the probe thus results in a signal (e.g. fluorescence) being produced by the reporter molecule, which can be detected and/or quantified.

In another aspect, the multi-probe comprises a reporter and a quencher molecule at opposing ends of the short recognition sequence, so that these moieties are in sufficient proximity to each other, that the quencher substantially reduces the signal produced by the reporter molecule. This is the case both when the probe is free in solution as well as when it is bound to the target nucleic acid. A particular detection aspect of the invention referred to as a "5' nuclease assay" is when the multi-probe may be susceptible to cleavage by the 5' nuclease activity of the DNA polymerase. This reaction may possibly result in separation of the quencher molecule from the reporter molecule and the production of a detectable signal. Thus, such probes can be used in amplification-based assays to detect and/or quantify the amplification process for a target nucleic acid.

In a first aspect, the present invention relates to libraries of multi-probes as discussed above. In such a library of oligonucleotide probes, each probe comprises a detection element and a recognition segment having a length of about x nucleotides, where some or all of the nucleo-bases in said oligonucleotides are substituted by non-natural bases having the effect of increasing binding affinity compared to natural nucleobases, and/or some or all of the nucleotide units of the oligonucleotide probe are modified with a chemical moiety to increase binding affinity, and/or where said oligonucleotides are modified with a chemical moiety to increase binding affinity, such that the probe has sufficient stability for binding to the target sequence under conditions suitable for detection, and wherein the number of different recognition segments comprises less than 10% of all possible segments of the given length, and wherein more than 90% of the probes can detect more than one complementary target in a target population of nucleic acids such that the library of oligonucleotide probes can detect a substantial fraction of all target sequences in a target population of nucleic acids.

The invention therefore relates to a library of oligonucleotide probes wherein each probe in the library consists of a recognition sequence tag and a detection moiety wherein at least one monomer in each oligonucleotide probe is a modified monomer analogue, increasing the binding affinity for the complementary target sequence relative to the corresponding unmodified oligodeoxyribonucleotide, such that the library probes have sufficient stability for sequence-specific binding and detection of a substantial fraction of a target nucleic acid in any given target population and wherein the number of different recognition sequences comprises less than 10% of all possible sequence tags of a given length(s).

The invention further relates to a library of oligonucleotide probes wherein the recognition sequence tag segment of the probes in the library have been modified in at least one of the following ways:

i) substitution with at least one non-naturally occurring nucleotide; and ii) substitution with at least one chemical moiety to increase the stability of the probe.

Further, the invention relates to a library of oligonucleotide probes wherein the recognition sequence tag has a length of 6 to 12 nucleotides (i.e. 6, 7, 8, 9, 10, 11 or 12), and wherein the preferred length is 8 or 9 nucleotides.

Further, the invention relates to recognition sequence tags that are substituted with LNA nucleotides.

Moreover, the invention relates to libraries of the invention where more than 90% of the oligonucleotide probes can bind and detect at least two target sequences in a nucleic acid population, preferably because the bound target sequences that are complementary to the recognition sequence of the probes.

Also preferably, the probe is capable of detecting more than one target in a target population of nucleic acids, e.g., the probe is capable of hybridizing to a plurality of different nucleic acid molecules contained within the target population of nucleic acids.

The invention also provides a method, system and computer program embedded in a computer readable medium ("a computer program product") for designing multi-probes comprising at least one stabilizing nucleobase. The method comprises querying a database of target sequences (e.g., such as a database of expressed sequences) and designing a small set of probes (e.g. such as 50 or 100 or 200 or 300 or 500) which: i) has sufficient binding stability to bind their respective target sequence under PCR conditions, ii) have limited propensity to form duplex structures with itself, and iii) are capable of binding to and detecting/quantifying at least about 60%, at least about 70%, at least about 80%, at least about 90% or at least about 95% of all the sequences in the given database of sequences, such as a database of expressed sequences.

Probes are designed in silico, which comprise all possible combinations of nucleotides of a given length forming a database of virtual candidate probes. These virtual probes are queried against the database of target sequences to identify probes that comprise the maximal ability to detect the most different target sequences in the database ("optimal probes"). Optimal probes so identified are removed from the virtual probe database. Additionally, target nucleic acids, which were identified by the previous set of optimal probes, are subtracted from the target nucleic acid database. The remaining probes are then queried against the remaining target sequences to identify a second set of optimal probes. The process is repeated until a set of probes is identified which can provide the desired coverage of the target sequence database. The set may be stored in a database as a source of sequences for transcriptome analysis. Multi-probes may be synthesized having recognition sequences, which correspond to those in the database to generate a library of multi-probes.

In one preferred aspect, the target sequence database comprises nucleic acid sequences corresponding to human mRNA (e.g., mRNA molecules, cDNAs, and the like).

In another aspect, the method further comprises calculating stability based on the assumption that the recognition sequence comprises at least one stabilizing nucleotide, such as an LNA molecule. In one preferred aspect the calculated stability is used to eliminate probe recognition sequences with inadequate stability from the database of virtual candidate probes prior to the initial query against the database of target sequence to initiate the identification of optimal probe recognition sequences.

In another aspect, the method further comprises calculating the propensity for a given probe recognition sequence to form a duplex structure with itself based on the assumption that the recognition sequence comprises at least one stabilizing nucleotide, such as an LNA molecule. In one preferred aspect the calculated propensity is used to eliminate probe recognition sequences that are likely to form probe duplexes from the database of virtual candidate probes prior to the initial query against the database of target sequence to initiate the determination of optimal probe recognition sequences.

In another aspect, the method further comprises evaluating the general applicability of a given candidate probe recognition sequence for inclusion in the growing set of optimal probe candidates by both a query against the remaining target sequences as well as a query against the original set of target sequences. In one preferred aspect only probe recognition sequences that are frequently found in both the remaining target sequences and in the original target sequences are added to in the growing set of optimal probe recognition sequences. In a most preferred aspect this is accomplished by calculating the product of the scores from these queries and selecting the probes recognition sequence with the highest product that still is among the probe recognition sequences with 20% best score in the query against the current targets.

The invention also provides a computer program embedded in a computer readable medium comprising instructions for searching a database comprising a plurality of different target sequences and for identifying a set of probe recognition sequences capable of identifying to at least about 60%, about 70%, about 80%, about 90% and about 95% of the sequences within the database. In one aspect, the program provides instructions for executing the method described above. In another aspect, the program provides instructions for implementing an algorithm as shown in FIG. 2. The invention further provides a system wherein the system comprises a memory for storing a database comprising sequence information for a plurality of different target sequences and also comprises an application program for executing the program instructions for searching the database for a set of probe recognition sequences which is capable of hybridizing to at least about 60%, about 70%, about 80%, about 90% and about 95% of the sequences within the database.

Another aspect of the invention relates to an oligonucleotide probe comprising a detection element and a recognition segment each independently having a length of about 1 to 8 nucleotides, wherein some or all of the nucleotides in the oligonucleotides are substituted by non-natural bases or base analogues having the effect of increasing binding affinity compared to natural nucleobases and/or some or all of the nucleotide units of the oligonucleotide probe are modified with a chemical moiety or replaced by an analogue to increase binding affinity, and/or where said oligonucleotides are modified with a chemical moiety or is an oligonucleotide analogue to increase binding affinity, such that the probe has sufficient stability for binding to the target sequence under conditions suitable for detection, and wherein the probe is capable of detecting more than one complementary target in a target population of nucleic acids.

A preferred embodiment of the invention is a kit for the characterization or detection or quantification of target nucleic acids comprising samples of a library of multi-probes. In one aspect, the kit comprises in silico protocols for their use. In another aspect, the kit comprises information relating to suggestions for obtaining inexpensive DNA primers. The probes contained within these kits may have any or all of the characteristics described above. In one preferred aspect, a plurality of probes comprises at least one stabilizing nucleotide, such as an LNA nucleotide. In another aspect, the plurality of probes comprises a nucleotide coupled to or stably associated with at least one chemical moiety for increasing the stability of binding of the probe. In a further preferred aspect, the kit comprises about 100 different probes. The kits according to the invention allow a user to quickly and efficiently develop an assay for thousands of different nucleic acid targets.

The invention further provides a multi-probe comprising one or more LNA nucleotide, which has a reduced length of about 8, or 9 nucleotides. By selecting commonly occurring 8 and 9-mers as targets it is possible to detect many different genes with the same probe. Each 8 or 9-mer probe can be used to detect more than 7000 different human mRNA sequences. The necessary specificity is then ensured by the combined effect of inexpensive DNA primers for the target gene and by the 8 or 9-mer probe sequence targeting the amplified DNA (FIG. 1).

In a preferred embodiment the present invention relates to an oligonucleotide multi-probe library comprising LNA-substituted octamers and nonamers of less than about 1000 sequences, preferably less than about 500 sequences, or more preferably less than about 200 sequences, such as consisting of about 100 different sequences selected so that the library is able to recognize more than about 90%, more preferably more than about 95% and more preferably more than about 98% of mRNA sequences of a target organism or target organ.

Positive Control Samples:

A recurring problem in designing real-time PCR detection assays for multiple genes is that the success-rate of these de-novo designs is less than 100%. Troubleshooting a non-functional assay can be cumbersome since ideally, a target specific template is needed for each probe, to test the functionality of the detection probe. Furthermore, a target specific template can be useful as a positive control if it is unknown whether the target is available in the test sample. When operating with a limited number of detection probes in a probelibrary kit as described in the present invention (e.g. 90), it is feasible to also provide positive control targets in the form of PCR-amplifiable templates containing all possible targets for the limited number of probes (e.g. 90). This feature allows users to evaluate the function of each probe, and is not feasible for non-recurring probe-based assays, and thus constitutes a further beneficial feature of the invention. For the suggested preferred probe recognition sequences listed in FIG. 13, we have designed concatamers of control sequences for all probes, containing a PCR-amplifiable target for every probe in the 40 first probes.

Probe Sequence Selection

An important aspect of the present invention is the selection of optimal probe target sequences in order to target as many targets with as few probes as possible, given a target selection criteria. This may be achieved by deliberately selecting target sequences that occur more frequently than what would have been expected from a random distribution.

The invention therefore relates in one aspect to a method of selecting oligonucleotide sequences useful in a multi-probe library of the invention, the method comprising a) providing a first list of all possible oligonucleotides of a predefined number of nucleotides, N (typically an integer selected from 6, 7, 8, 9, 10, 11, and 12, preferably 8 or 9), said oligonucleotides having a melting temperature, Tm, of at least 50° C. (preferably at least 60° C.), b) providing a second list of target nucleic acid sequences (such as a list of a target nucleic acid population discussed herein), c) identifying and storing for each member of said first list, the number of members from said second list, which include a sequence complementary to said each member, d) selecting a member of said first list, which in the identification in step c matches the maximum number, identified in step c, of members from said second list, e) adding the member selected in step d to a third list consisting of the selected oligonucleotides useful in the library according to any one of the preceding claims, f) subtracting the member selected in step d from said first list to provide a revised first list, m) repeating steps d through f until said third list consists of members which together will be contemplary to at least 30% of the members on the list of target nucleic acid sequences from step b (normally the percentage will be higher, such as at least 40%, at least 50%, at least 60%, at least 70%, at least 75%, at least 80%, at least 85%, at least 90%, at least 95%, or even higher such as at least 97%, at least 98% and even as high as at least 99%).

It is preferred that the first list only includes oligonucleotides incapable of self-hybridization in order to render a subsequent use of the probes less prone to false positives.

The selection method may include a number of steps after step f, but before step m g) subtraction of all members from said second list which include a sequence complementary to the member selected in step d to obtain a revised second list, h) identification and storing of, for each member of said revised first list, the number of members from said revised second list, which include a sequence complementary to said each member, i) selecting a member of said first list, which in the identification in step h matches the maximum number, identified in step h, of members from said second list, or selecting a member of said first list provides the maximum number obtained by multiplying the number identified in step h with the number identified in step c, j) addition of the member selected in step i to said third list, k) subtraction of the member selected in step i from said revised first list, and l) subtraction of all members from said revised second list which include a sequence or complementary to the member selected in step i.

The selection in step d after step c is conveniently preceded by identification of those members of said first list which hybridizes to more than a selected percentage (60% or higher such as the preferred 80%) of the maximum number of members from said second list so that only those members so identified are subjected to the selection in step d.

In the practical implementation of the selection method, said first, second and third lists are stored in the memory of a computer system, preferably in a database. The memory (also termed "computer readable medium") can be both volatile and non-volatile, i.e. any memory device conventionally used in computer systems: a random access memory (RAM), a read-only memory (ROM), a data storage device such as a hard disk, a CD-ROM, DVD-ROM, and any other known memory device.

The invention also provides a computer program product providing instructions for implementing the selection method, embedded in a computer-readable medium (defined as above). That is, the computer program may be compiled and loaded in an active computer memory, or it may be loaded on a non-volatile storage device (optionally in a compressed format) from where it can be executed. Consequently, the invention also includes a system comprising a database of target sequences and an application program for executing the computer program. A source code for such a computer program is set forth in FIGS. 17A-17T.

In a randomly distributed nucleic acid population, the occurrence of selected sequences of a given length will follow a statistical distribution defined by:

$N1$=the complete length of the given nucleic acid population (e.g. 76.002.917 base pairs as in the 1 Jun. 30, 2003 release of RefSeq).

$N2$=the number of fragments comprising the nucleic acid population (e.g. 38.556 genes in the 1 Jun. 30, 2003 release of RefSeq).

$N3$=the length of the recognition sequence (e.g. 9 base pairs)

$N4$=the occurrence frequency $N4 = (N1 - ((N3-1) \times 2 \times N2))/(4^{N3})$ Eg.

$$\frac{76{,}002{,}917 - 8 \times 2 \times 38{,}556}{4^9} = \text{approximately 287 occurrences of}$$

9-mer sequences or or $$\frac{76{,}002{,}917 - 7 \times 2 \times 38{,}556}{4^8} = \text{approximately 1{,}151 occurrences}$$

of 8-mer sequences

Hence, as described in the example given above, a random 8-mer and 9-mer sequence would on average occur 1,151 and 287 times, respectively, in a random population of the described 38,556 mRNA sequences.

In the example above, the 76.002.917 base pairs originating from 38.556 genes would correspond to an average transcript length of 1971 bp, containing each 1971-16 or 1955 9-mer target sequences each. Thus as a statistical minimum, 38.556/1955/287 or 5671 9-mer probes would be needed for one probe to target each gene.

However, the occurrence of 9-mer sequences is not randomly distributed. In fact, a small subset of sequences occur at surprisingly high prevalence, up to over 30 times the prevalence anticipated from a random distribution. In a specific target population selected according to preferred criteria, preferably the most common sequences should be selected to increase the coverage of a selected library of probe target sequences. As described previously, selection should be step-wise, such that the selection of the most common target sequences is evaluated as well in the starting target population as well as in the population remaining after each selection step.

In a preferred embodiment of the invention the targets for the probelibrary are the entire expressed transcriptome.

Because the success rate of the reverse transcriptase reaction diminishes with the distance from the RT-primer used, and since using a poly-T primer targeting the poly-A tract in mRNAs is common, the above-mentioned target can further be restricted to only include the 1000 most proximal bases in each mRNA. This may result in the selection of another set of optimal probe target sequences for optimal coverage.

Likewise the above-mentioned target may be restricted to include only the 50 bp of coding region sequence flanking the introns of a gene to ensure assays that preferably only monitor mRNA and not genomic DNA or to only include regions not containing di-, tri- or tetra repeat sequences, to avoid repetitive binding or probes or primers or regions not containing know allelic variation, to avoid primer or probe mis-annealing due to sequence variations in target sequences or regions of extremely high GC-content to avoid inhibition of PCR amplification.

Depending on each target selection the optimal set of probes may vary, depending in the prevalence of target sequences in each target selection.

Selection of Detection Means and Identification of Single Nucleic Acids

Another part of the invention relates to identification of a means for detection of a target nucleic acid, the method comprising A) inputting, into a computer system, data that uniquely identifies the nucleic acid sequence of said target nucleic acid, wherein said computer system comprises a database holding information of the composition of at least one library of nucleic acid probes of the invention, and wherein the computer system further comprises a database of target nucleic acid sequences for each probe of said at least one library and/or further comprises means for acquiring and comparing nucleic acid sequence data, B) identifying, in the computer system, a probe from the at least one library, wherein the sequence of the probe exists in the target nucleic acid sequence or a sequence complementary to the target nucleic acid sequence, C) identifying, in the computer system, primer that will amplify the target nucleic acid sequence, and D) providing, as identification of the specific means for detection, an output that points out the probe identified in step B and the sequences of the primers identified in step C.

The above-outlined method has several advantages in the event it is desired to rapidly and specifically identify a particular nucleic acid. If the researcher already has acquired a suitable multi-probe library of the invention, the method makes it possible within seconds to acquire information relating to which of the probes in the library one should use for a subsequent assay, and of the primers one should synthesize. The time factor is important, since synthesis of a primer pair can be accomplished overnight, whereas synthesis of the probe would normally be quite time-consuming and cumbersome.

To facilitate use of the method, the probe library can be identified (e.g. by means of a product code which essentially tells the computer system how the probe library is composed). Step A then comprises inputting, into the computer system, data that identifies the at least one library of nucleic acids from which it is desired to select a member for use in the specific means for detection.

The preferred inputting interface is an internet-based web-interface, because the method is conveniently stored on a web server to allow access from users who have acquired a probe library of the present invention. However, the method also would be useful as part of a installable computer application, which could be installed on a single computer or on a local area network.

In preferred embodiments of this method, the primers identified in step C are chosen so as to minimize the chance of amplifying genomic nucleic acids in a PCR reaction. This is of course only relevant where the sample is likely to contain genomic material. One simple way to minimize the chance of amplification of genomic nucleic acids is to include, in at least one of the primers, a nucleotide sequence which in genomic DNA is interrupted by an intron. In this way, the primer will only prime amplification of transcripts where the intron has been spliced out.

A further optimization of the method is to choose the primers in step C so as to minimize the length of amplicons obtained from PCR performed on the target nucleic acid sequence and it is further also preferred to select the primers so as to optimize the GC content for performing a subsequent PCR.

As for the probe selection method, the selection method for detection means can be provided to the end-user as a computer program product providing instructions for implementing the method, embedded in a computer-readable medium. Consequently, the invention also provides for a system comprising a database of nucleic acid probes of the invention and an application program for executing this computer program.

The method and the computer programs and system allows for quantitative or qualitative determination of the presence of a target nucleic acid in a sample, comprising i) identifying, by means of the detection means selection method of the invention, a specific means for detection of the target nucleic acid, where the specific means for detection comprises an oligonucleotide probe and a set of primers, ii) obtaining the primers and the oligonucleotide probe identified in step i), iii) subjecting the sample to a molecular amplification procedure in the presence of the primers and the oligonucleotide probe from step ii), and iv) determining the presence of the target nucleic acid based on the outcome of step iii).

Conveniently, primers obtained in step ii) are obtained by synthesis and it is preferred that the oligonucleotide probe is obtained from a library of the present invention.

The molecular amplification method is typically a PCR or a NASBA procedure, but any in vitro method for specific amplification (and, possibly, detection) of a nucleic acid is useful. The preferred PCR procedure is a qPCR (also known as real-time reverse transcription PCR or kinetic RT-PCR).

Other aspects of the invention are discussed infra.

BRIEF DESCRIPTION OF THE DRAWINGS

FIG. 1A illustrates the use of conventional long probes. FIG. 1A shows a method according to the prior art.

FIG. 1B illustrates the properties and use of short multi-probes from a library constructed according to the invention. The short multi-probes comprise a recognition segment chosen so that each probe sequence may be used to detect and/or quantify several different target sequences comprising the complementary recognition sequence. FIG. 1B shows a method according to one aspect of the invention.

FIG. 7A: Molecular beacon probe with a 10-mer recognition site de-tecting the 469 SSA4 amplicon. Signal was only obtained in the sample where SSA4 cDNA was added ($2 \times 10^7$ copies). A $C_t$ value of 24.0 was obtained. A similar experiment with a molecular beacon having a 9-mer recognition site detecting the 570 SSA4 amplicon is shown in FIG. 7B. Signal was only obtained when SSA4 cDNA was added ($2 \times 10^7$ copies).

Figure 10:
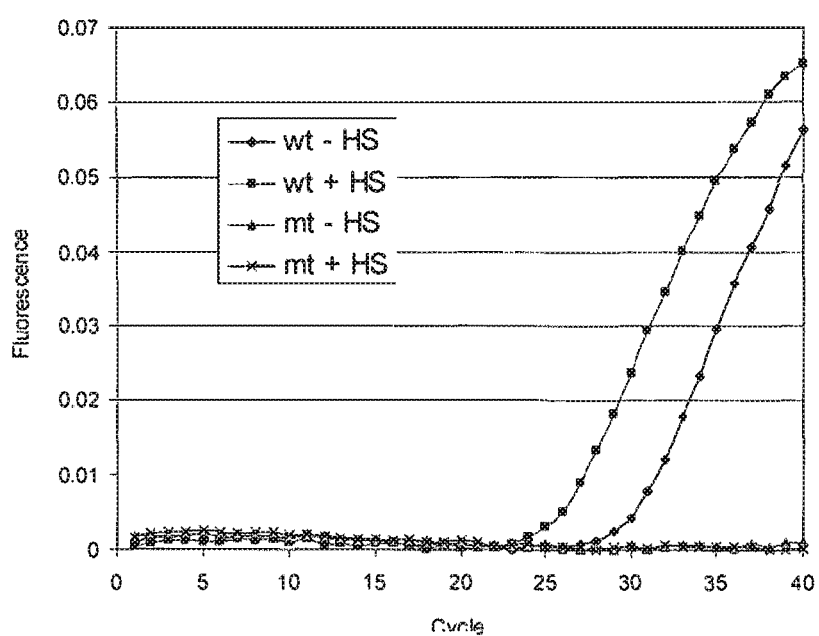
FIG. 10 shows the use of 9-mer dual labelled multi-probes to quantify a heat shock protein before and after-exposure to heat shock in a wild type yeast strain as well as a mutant strain where the corresponding gene has been deleted. Real time detection of SSA4 transcript levels in wild type (wt) yeast and in the SSA4 knockout mutant with the Dual-labelled-570 probe is shown. The different strains were either cultured at 30° C. till harvest (−HS) or they were exposed to 40° C. for 30 minutes prior to harvest. The Dual-labelled-570 probe was used in this example. The transcript was only detected in the wt type strain, where it was most abundant in the +HS culture. $C_t$ values were 26, 1 and 30.3 for the +HS and the −HS culture, respectively.

In FIG. 11A Dual-labelled-469 detects both the SSA4 (469 amplicon) and the POL5 transcript with $C_t$ values of 29.7 and 30.1, respectively. No signal was detected from the APG9 and HSP82 transcripts. In FIG. 11B Dual-labelled-570 detects both the SSA4 (570 amplicon) and the APG9 transcript with $C_t$ values of 31.3 and 29.2 respectively. No signal is detected from the POL5 and HSP82 transcripts. In FIG. 11C probe Dual-labelled-671 detected both the SSA4 (671 amplicon) and the HSP82 transcript with $C_t$ values of 29.8 and 25.6 respectively. No signal was detected from the POL5 and APG9 transcripts. The amplicon produced in the different PCRs is indicated in the legend. The same amount of cDNA was used as in the experiments depicted in FIG. 10. Only cDNA from non-heat shocked wild type yeast was used.

Figure 11A:
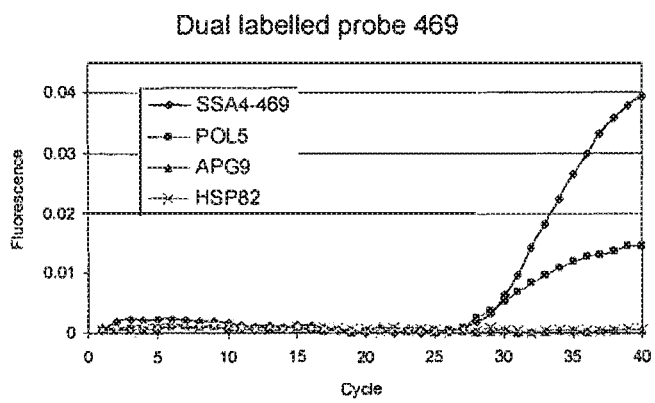
FIG. 11A, FIG. 11B, and FIG. 11C show an example of how more than one gene can be detected by the same 9-mer probe while nucleic acid molecules without the probe target sequence (i.e. complementary to the recognition sequence) will not be detected.
Figure 11B:
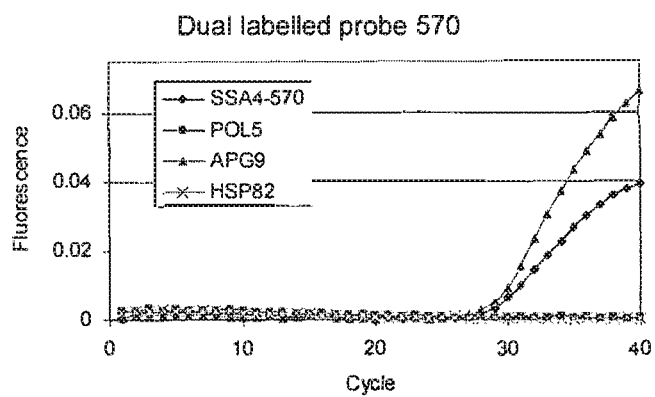
Figure 11C:
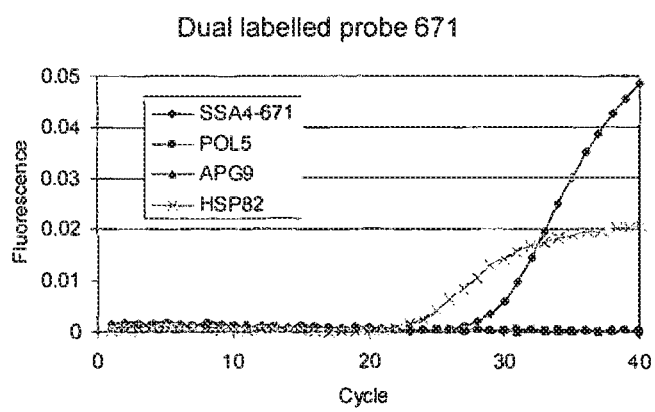
Figure 12:
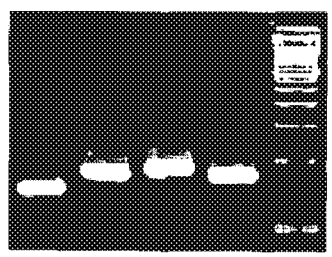

FIG. 12 shows agarose gel electrophoresis of a fraction of the arnplicons generated in the PCR reactions shown in the example of FIG. 11A, FIG. 11B, and FIG. 11C, demonstrating that the probes are specific for target sequences comprising the recognition sequence but do not hybridize to nucleic acid molecules which do not comprise the target sequence. In lane 1 contain the SSA4-469 amplicon (81 bp), lane 2 contains the POL5 amplicon (94 bp), lane 3 contains the APG9 amplicon (97 bp) and lane 4 contains the HSP82 amplicon (88 bp). Lane M contains a 50 bp ladder as size indicator. It is clear that a product was formed in all four cases; however, only amplificates containing the correct multi-probe target sequence (i.e. SSA4-467 and POL5) were detected by the dual labelled probe 467. That two different amplificates were indeed produced and detected is evident from the size difference in the detected fragments from lane 1 and 2.

FIG. 13: Preferred target sequences.

FIG. 14: Further Preferred target sequences.

FIG. 15: Longmers (positive controls). The sequences are set forth in SEQ ID NOs. 32-46.

FIG. 16: Procedure for the selection of probes and the designing of primers for qPCR.

Figure 17D:
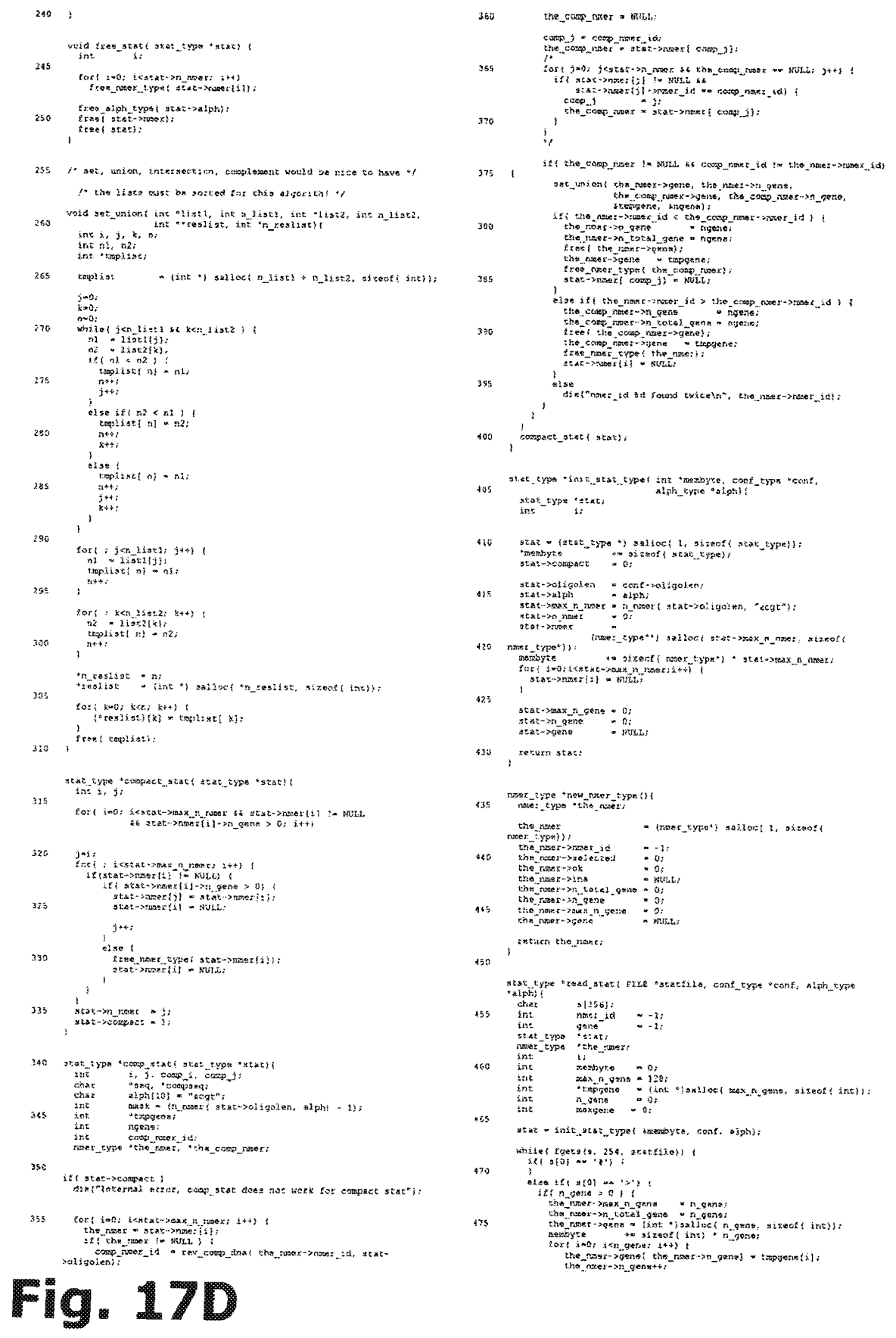
Figure 17E:
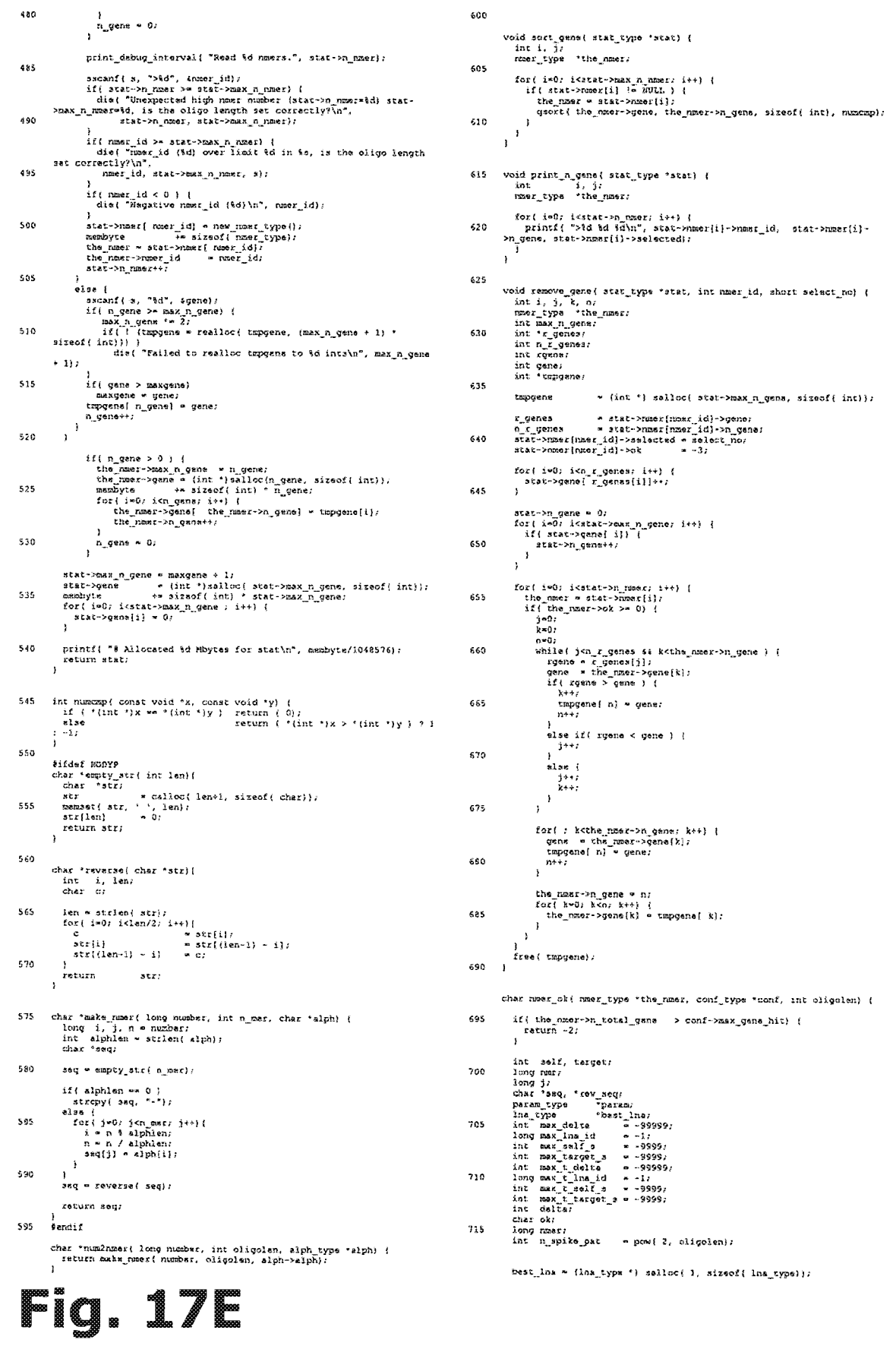
Figure 17G:
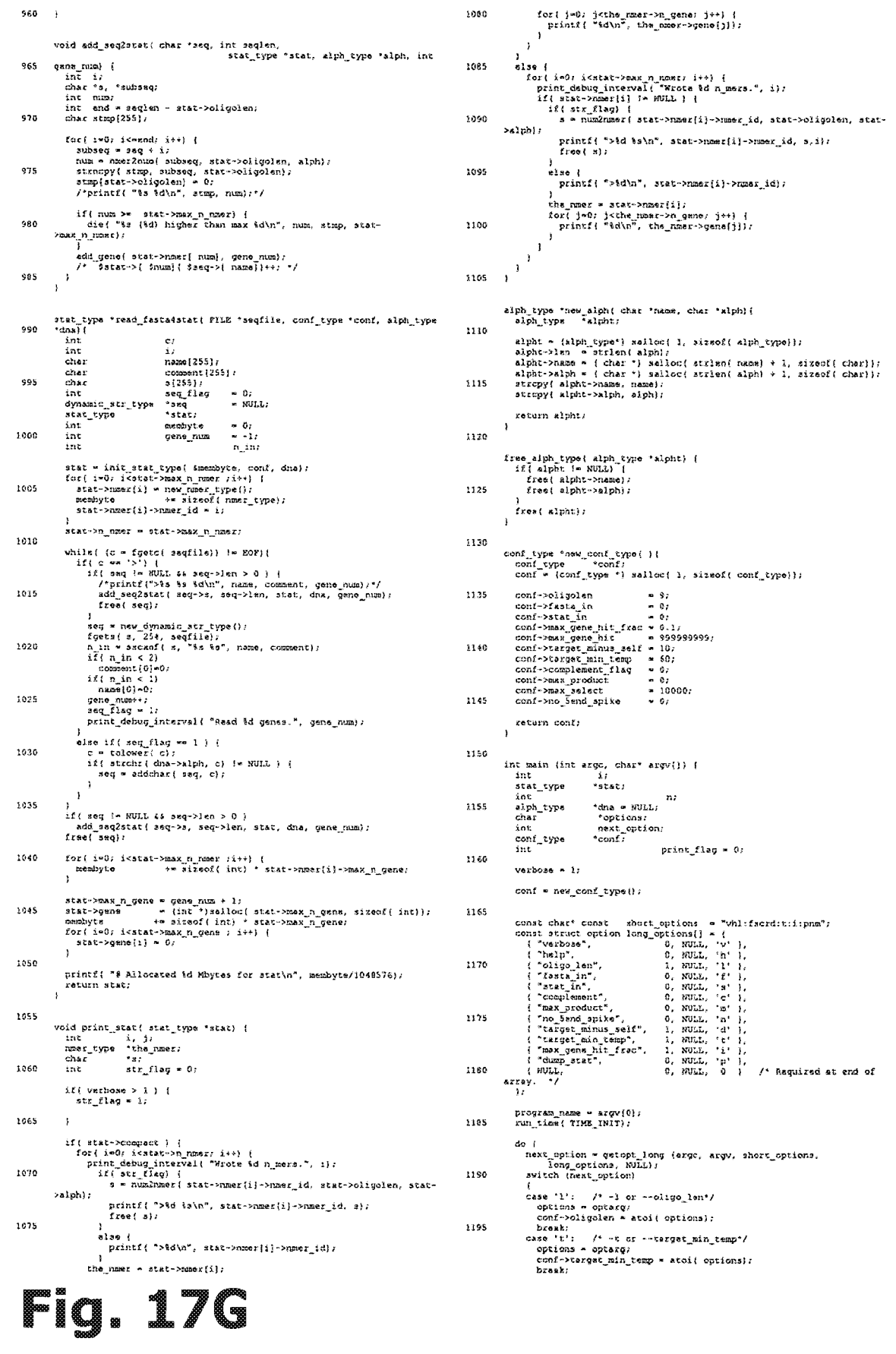
Figure 17H:
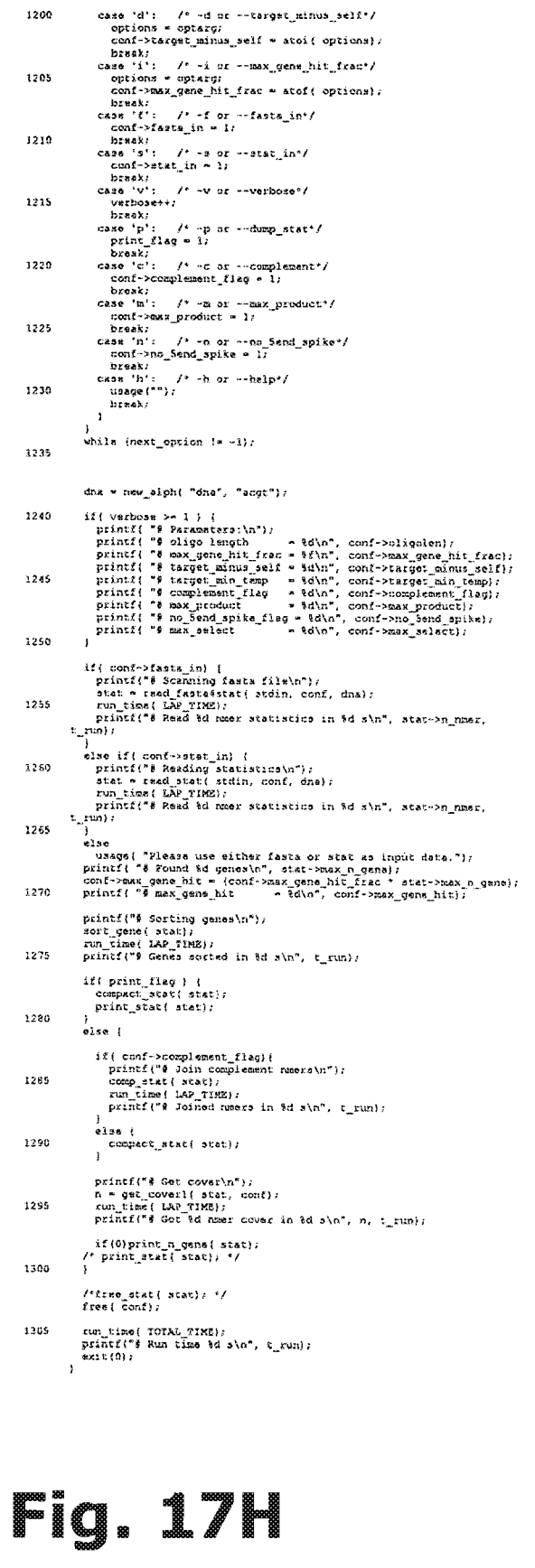
Figure 17I:
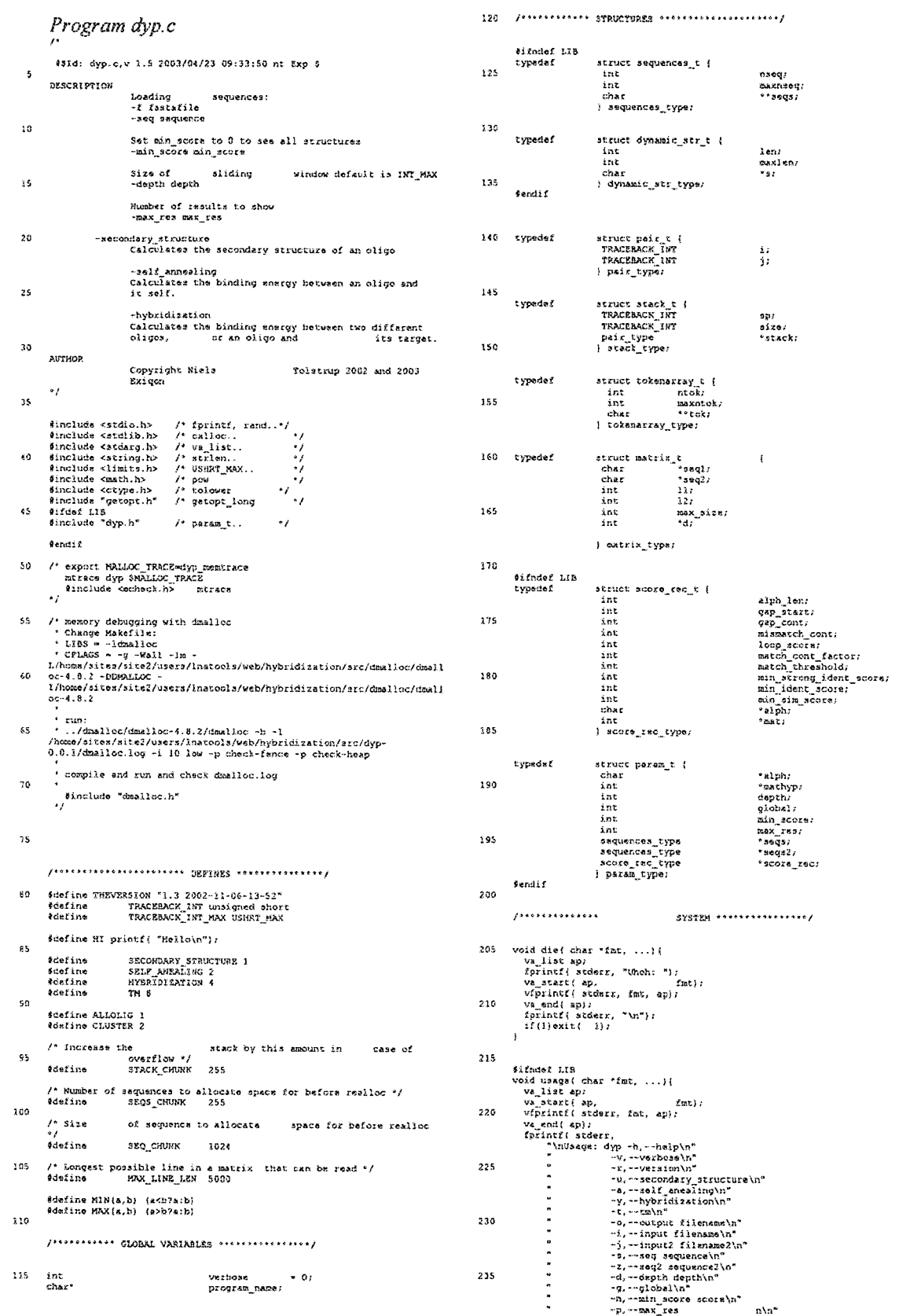
Figure 17J:
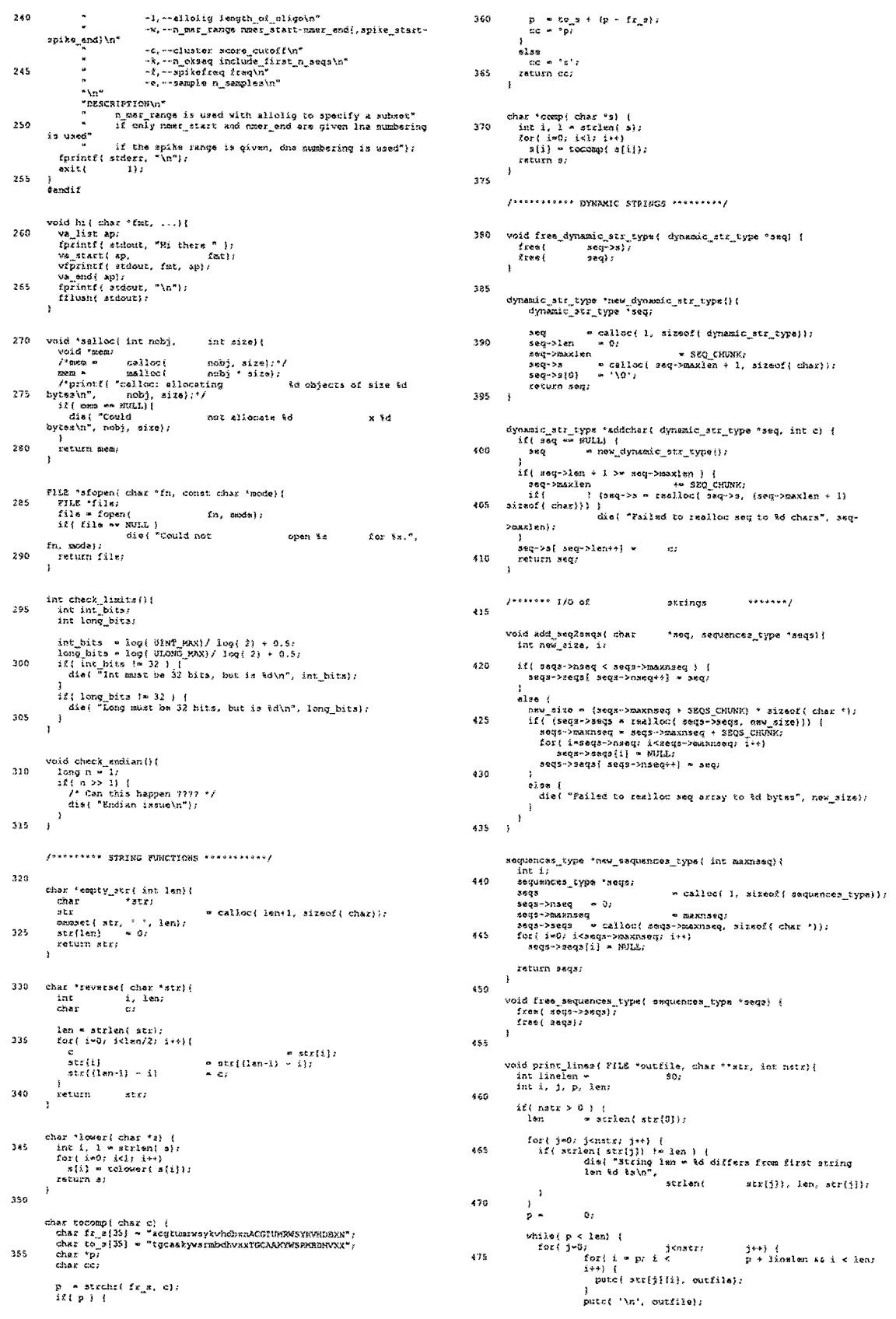
Figure 17K:
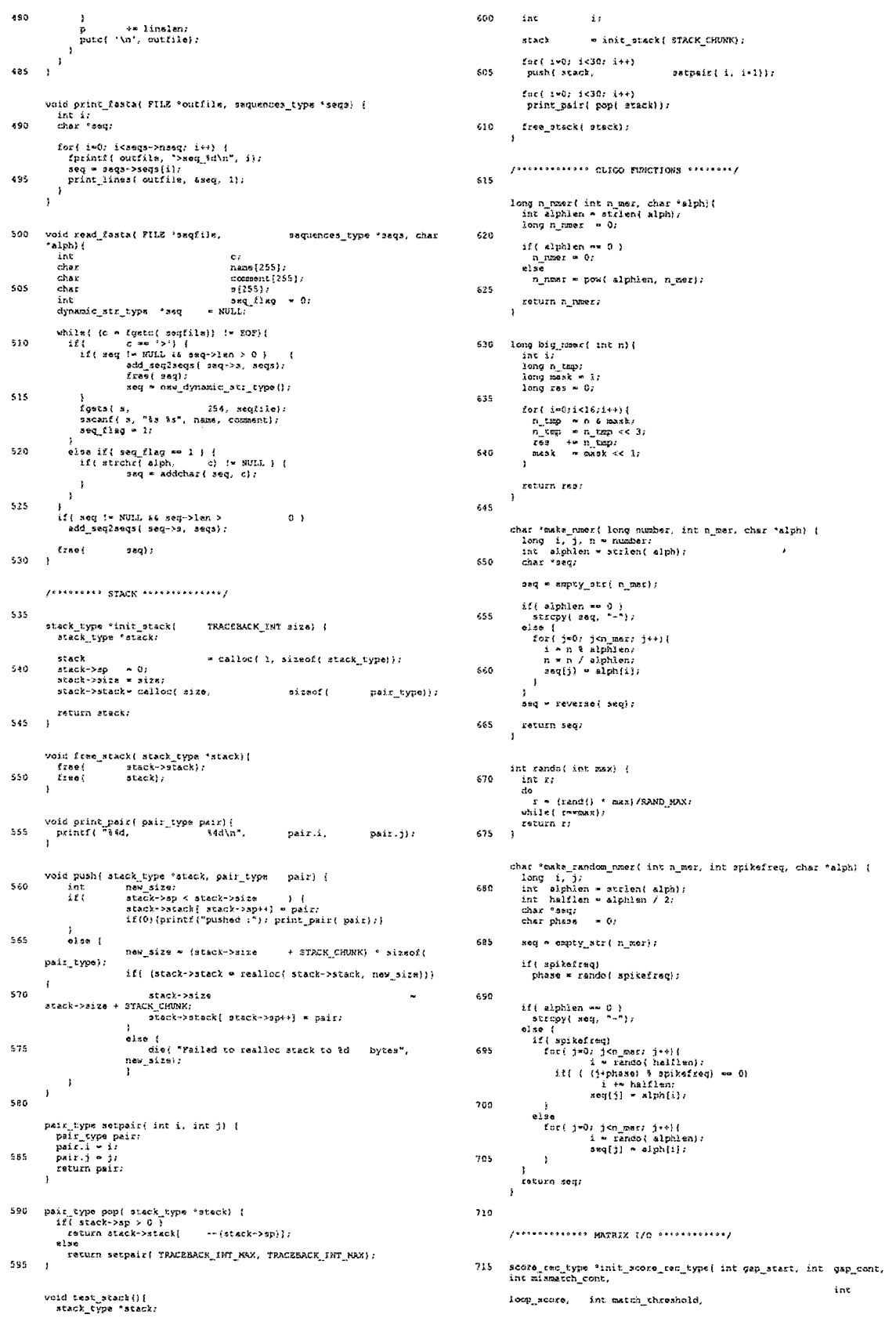
Figure 17M:
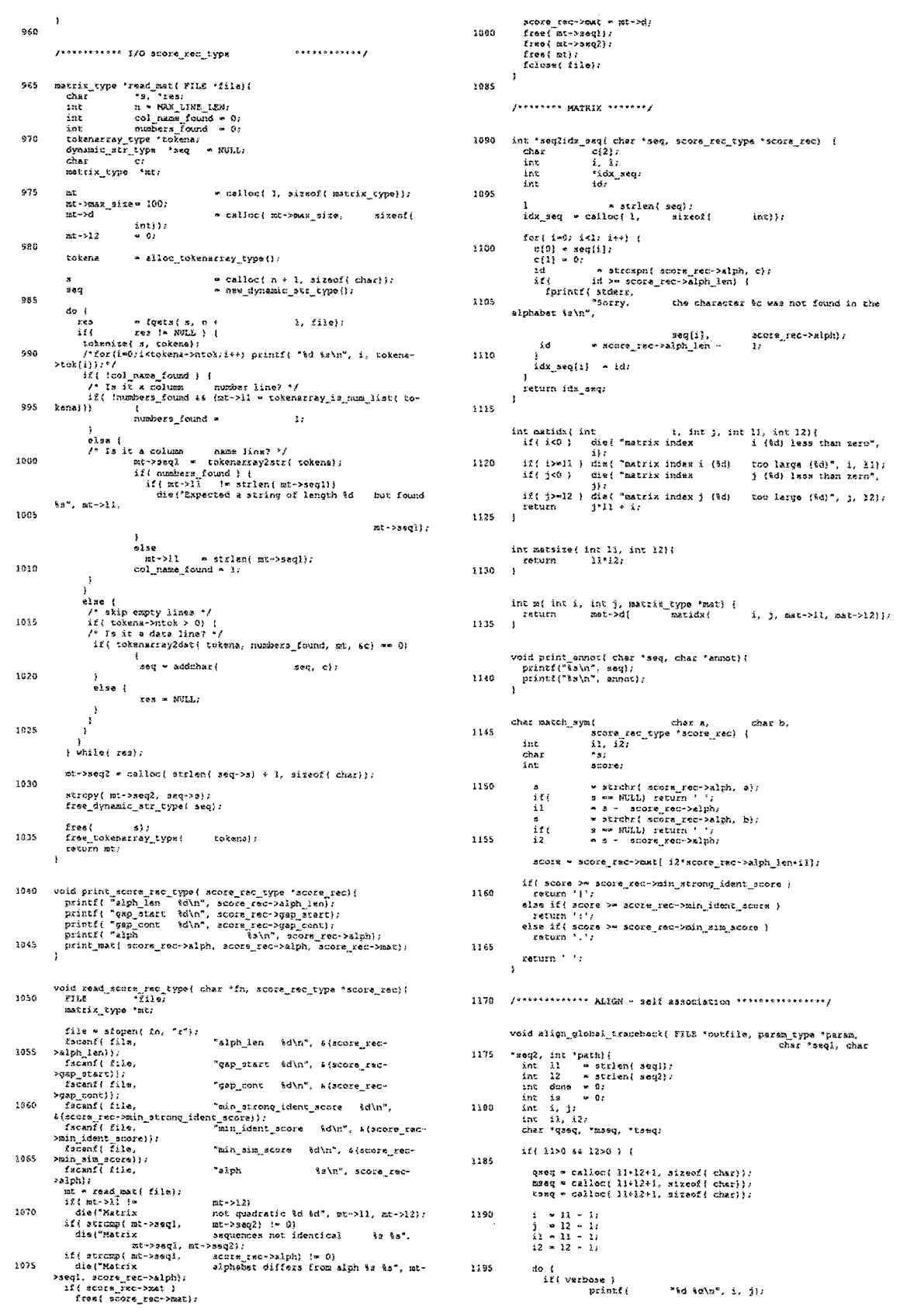
Figure 17N:
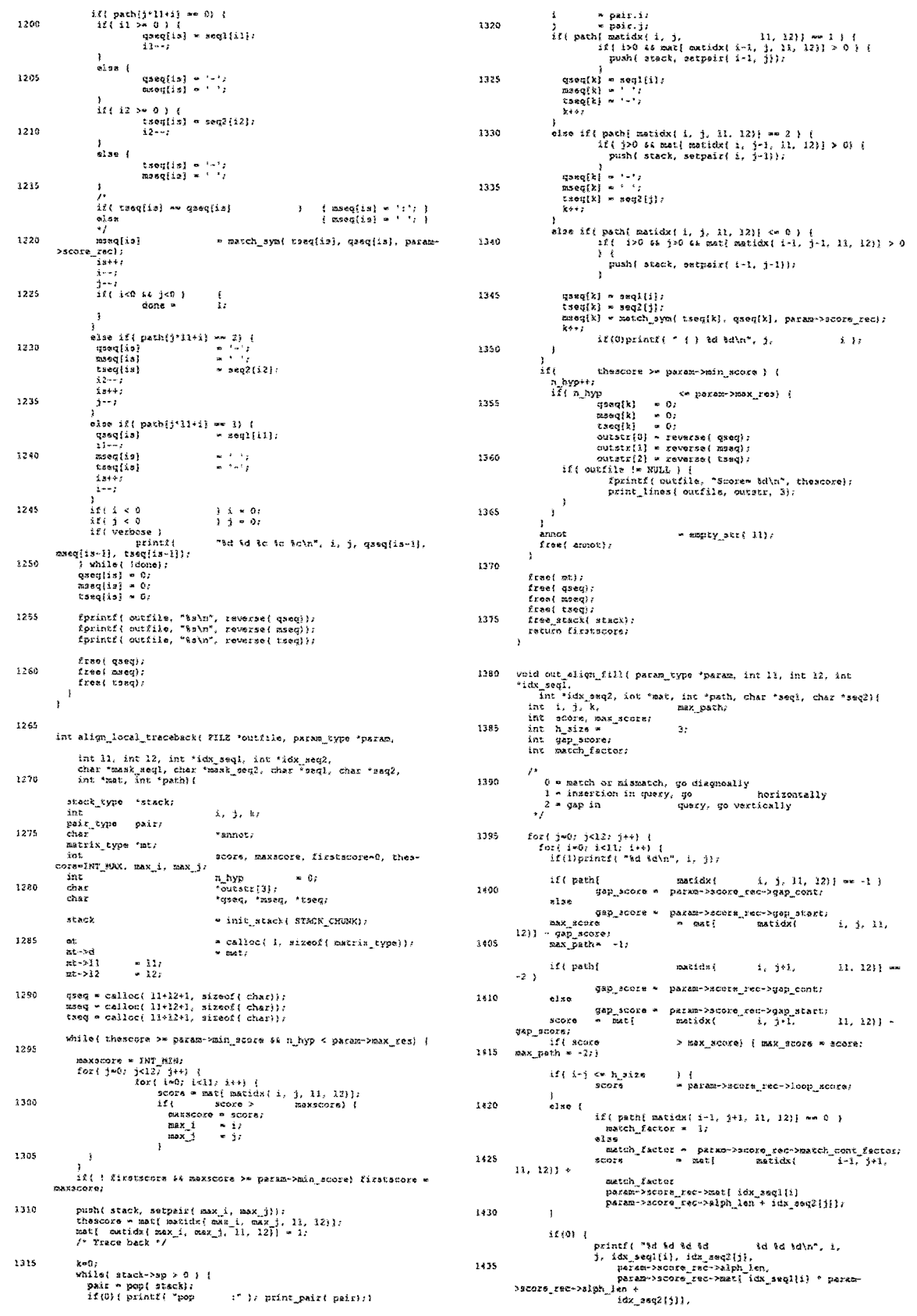
Figure 17P:
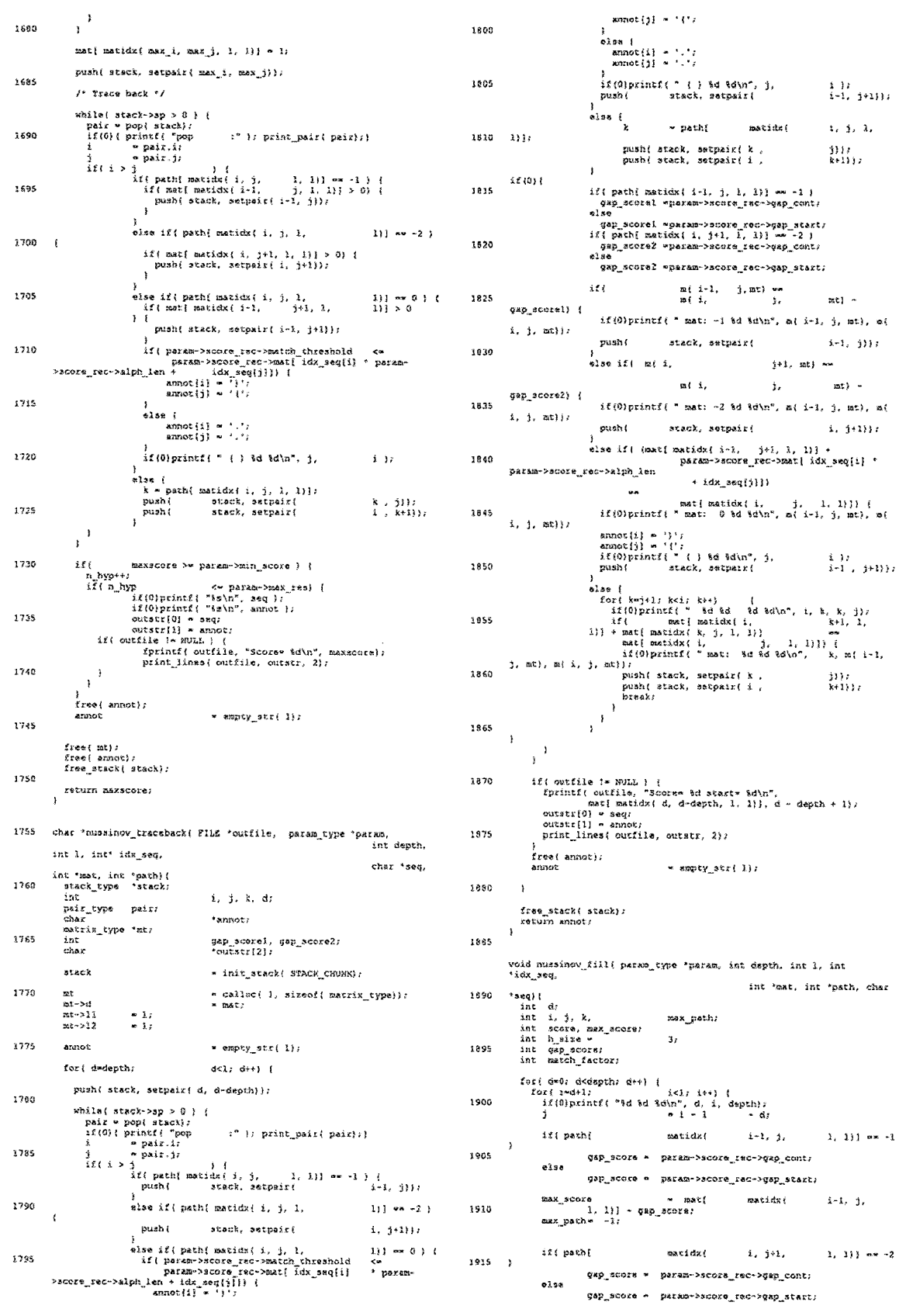
Figure 17Q:
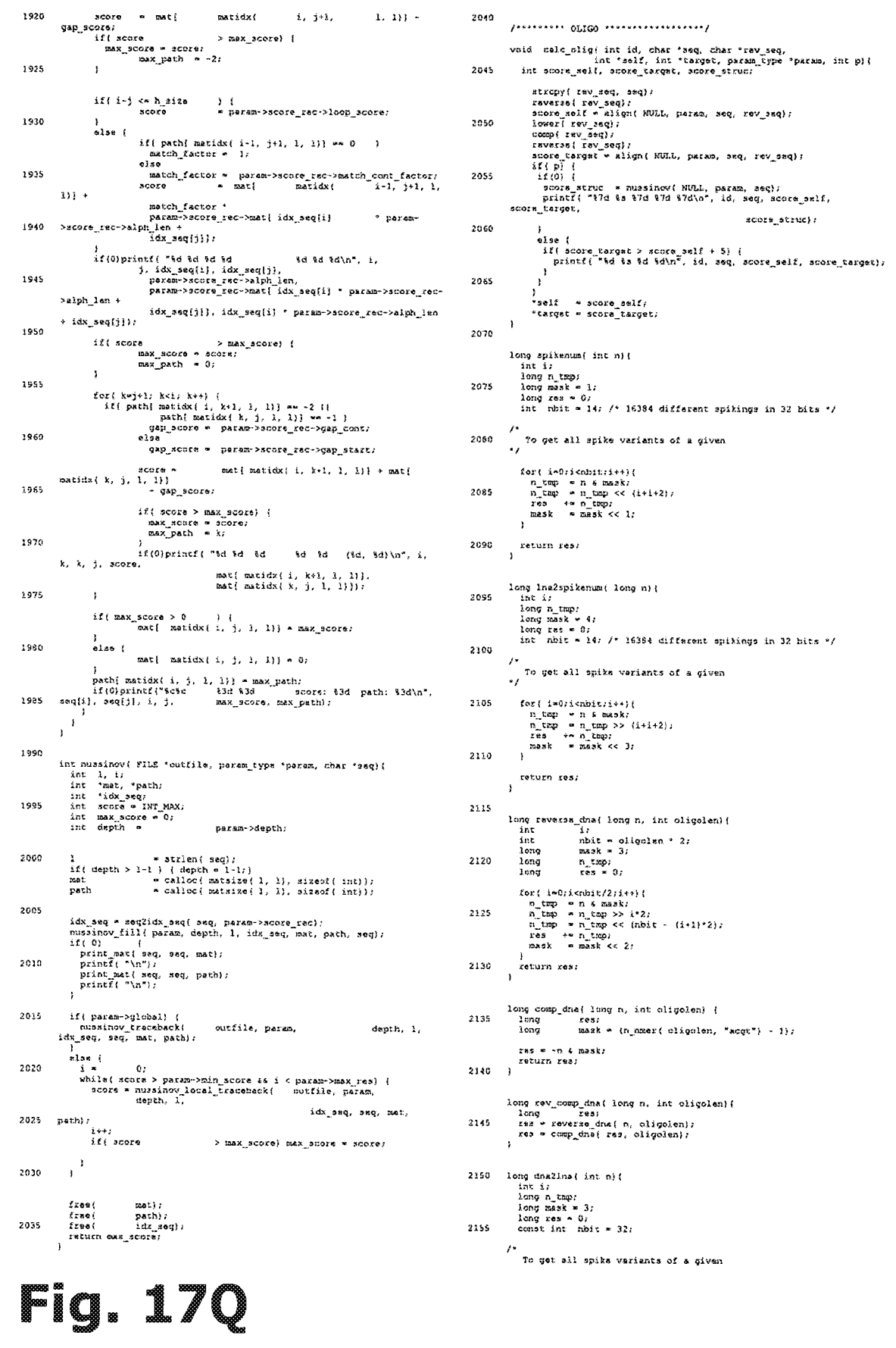
Figure 17R:
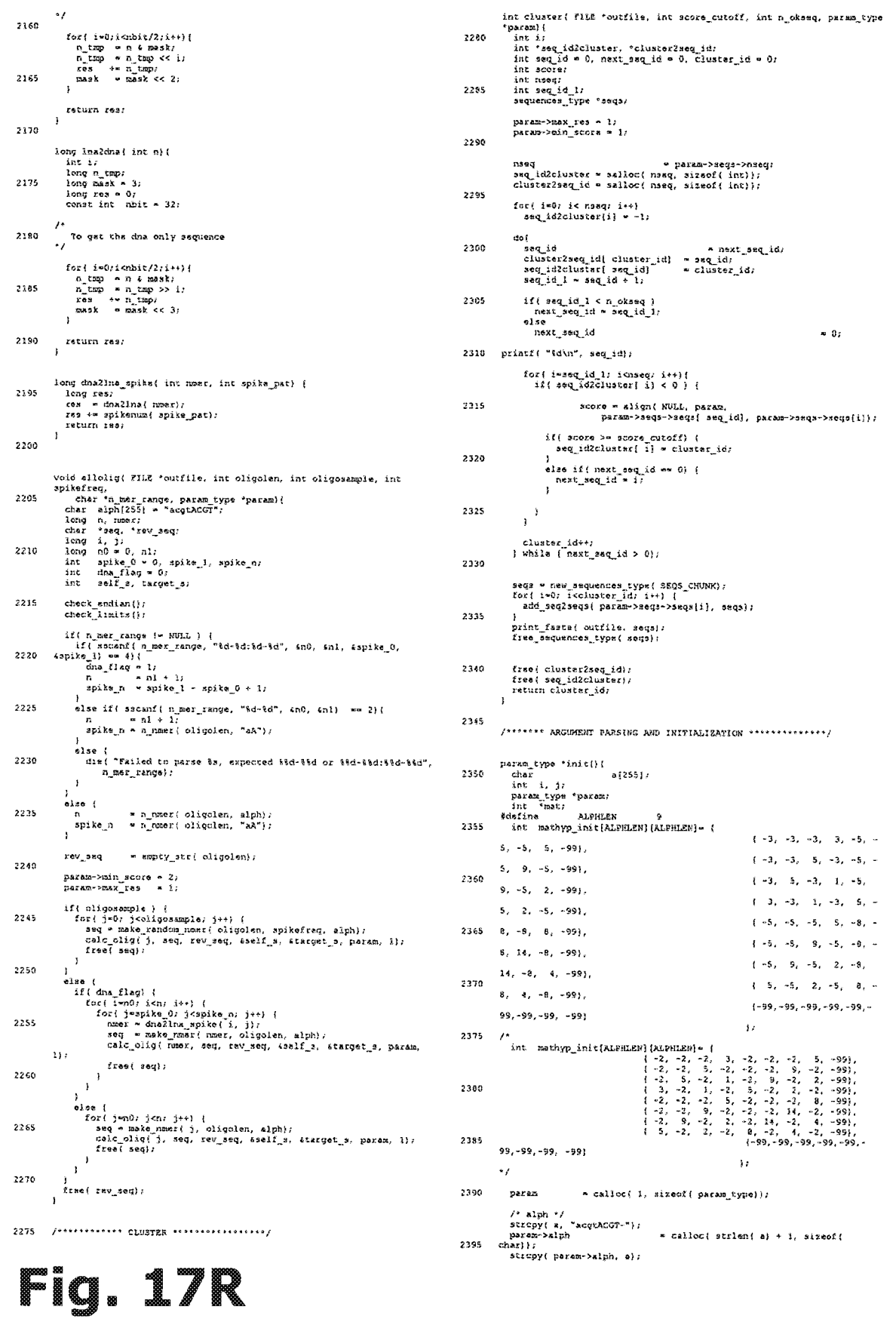
Figure 17S:
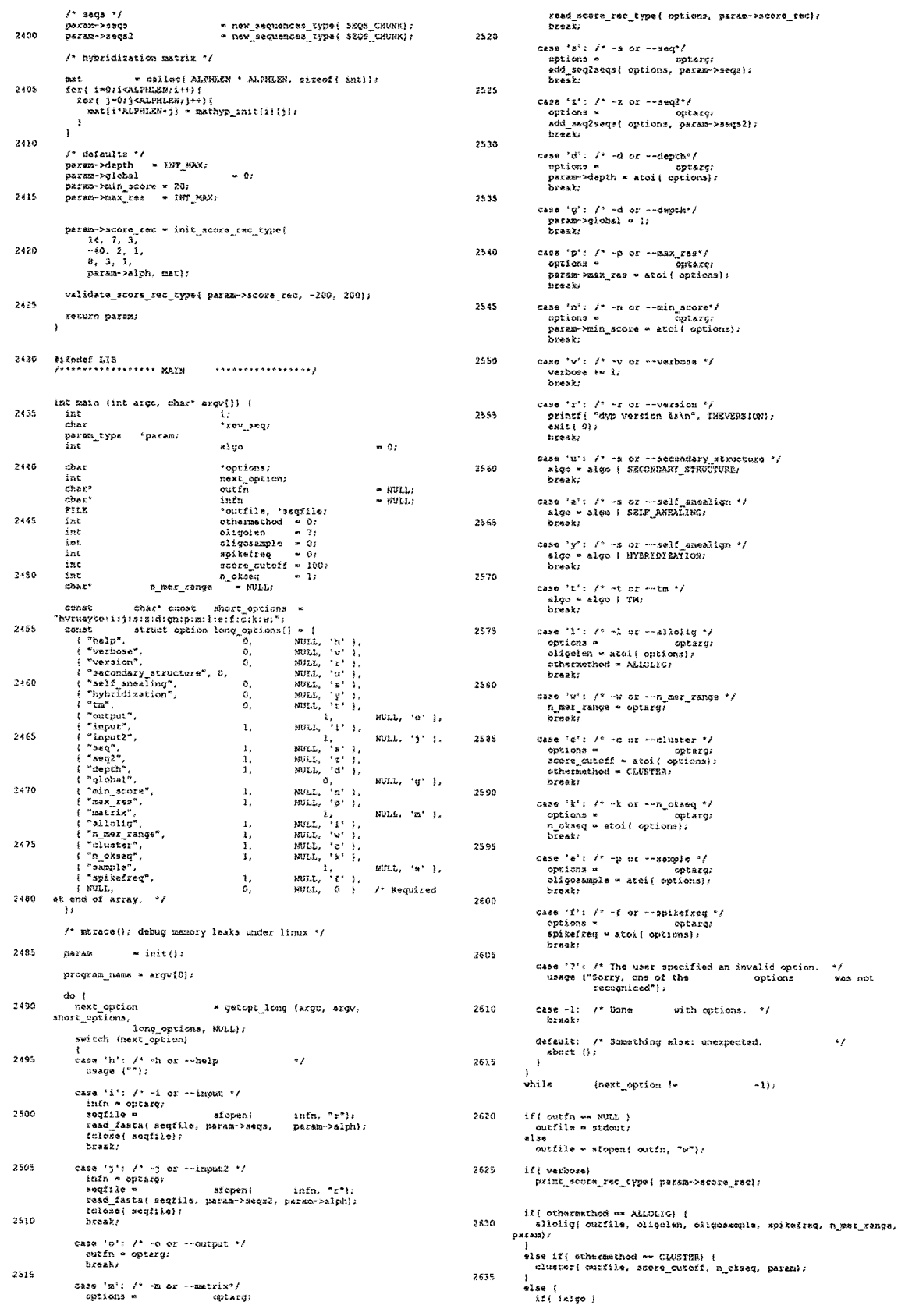

FIG. 17A, FIG. 17B, FIG. 17C, FIG. 17D, FIG. 17E, FIG. 17F, FIG. 17G, FIG. 17H, FIG. 17I, FIG. 17J, FIG. 17K, FIG. 17L, FIG. 17M, FIG. 17N, FIG. 17O, FIG. 17P, FIG. 17Q, FIG. 17R, FIG. 17S, and FIG. 17T: Source code for the program used in the calculation of a multi-probe dataset.

DETAILED DESCRIPTION

The present invention relates to short oligonucleotide probes or multi-probes, chosen and designed to detect, classify or characterize, and/or quantify many different target nucleic acid molecules. These multi-probes comprise at least one non-natural modification (e.g. such as LNA nucleotide) for increasing the binding affinity of the probes for a recognition sequence, which is a subsequence of the target nucleic acid molecules. The target nucleic acid molecules are otherwise different outside of the recognition sequence.

In one aspect, the multi-probes comprise at least one nucleotide modified with a chemical moiety for increasing binding affinity of the probes for a recognition sequence, which is a subsequence of the target nucleic acid sequence. In another aspect, the probes comprise both at least one non-natural nucleotide and at least one nucleotide modified with a chemical moiety. In a further aspect, the at least one non-natural nucleotide is modified by the chemical moiety. The invention also provides kits, libraries and other compositions comprising the probes.

The invention further provides methods for choosing and designing suitable oligonucleotide probes for a given mixture of target sequences, ii) individual probes with these abilities, and iii) libraries of such probes chosen and designed to be able to detect, classify, and/or quantify the largest number of target nucleotides with the smallest number of probe sequences. Each probe according to the invention is thus able to bind many different targets, but may be used to create a specific assay when combined with a set of specific primers in PCR assays.

Preferred oligonucleotides of the invention are comprised of about 8 to 9 nucleotide units, a substantial portion of which comprises stabilizing nucleotides, such as LNA nucleotides. A preferred library contains approximately 100 of these probes chosen and designed to characterize a specific pool of nucleic acids, such as mRNA, cDNA or genomic DNA. Such a library may be used in a wide variety of applications, e.g., gene expression analyses, SNP detection, and the like. (See, e.g., FIG. 1).

Definitions

The following definitions are provided for specific terms, which are used in the disclosure of the present invention:

As used herein, the singular form "a", an and the include plural references unless the context clearly dictates otherwise. For example, the term "a cell" includes a plurality of cells, including mixtures thereof. The term "a nucleic acid molecule" includes a plurality of nucleic acid molecules.

As used herein, the term "transcriptome" refers to the complete collection of transcribed elements of the genome of any species.

In addition to mRNAs, it also represents non-coding RNAs which are used for structural and regulatory purposes.

As used herein, the term "amplicon" refers to small, replicating DNA fragments.

As used herein, a "sample" refers to a sample of tissue or fluid isolated from an organism or organisms, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

As used herein, an "organism" refers to a living entity, including but not limited to, for example, human, mouse, rat, *Drosophila, C. elegans*, yeast, *Arabidopsis*, zebra fish, primates, domestic animals, etc.

By the term "SBC nucleobases" is meant "Selective Binding Complementary" nucleobases, i.e. modified nucleobases that can make stable hydrogen bonds to their complementary nucleobases, but are unable to make stable hydrogen bonds to other SBC nucleobases. As an example, the SBC nucleobase A', can make a stable hydrogen bonded pair with its complementary unmodified nucleobase, T. Likewise, the SBC nucleobase T' can make a stable hydrogen bonded pair with its complementary unmodified nucleobase, A. However, the SBC nucleobases A' and T' will form an unstable hydrogen bonded pair as compared to the basepairs A'-T and A-T'. Likewise, a SBC nucleobase of C is designated C' and can make a stable hydrogen bonded pair with its complementary unmodified nucleobase G, and a SBC nucleo-base of G is designated G' and can make a stable hydrogen bonded pair with its complementary unmodified nucleobase C, yet C' and G' will form an unstable hydrogen bonded pair as compared to the basepairs C'-G and C-G'. A stable hydrogen bonded pair is obtained when 2 or more hydrogen bonds are formed e.g. the pair between A' and T, A and T', C and G', and C' and G. An unstable hydrogen bonded pair is obtained when 1 or no hydrogen bonds is formed e.g. the pair between A' and T', and C' and G'.

Figure 4:
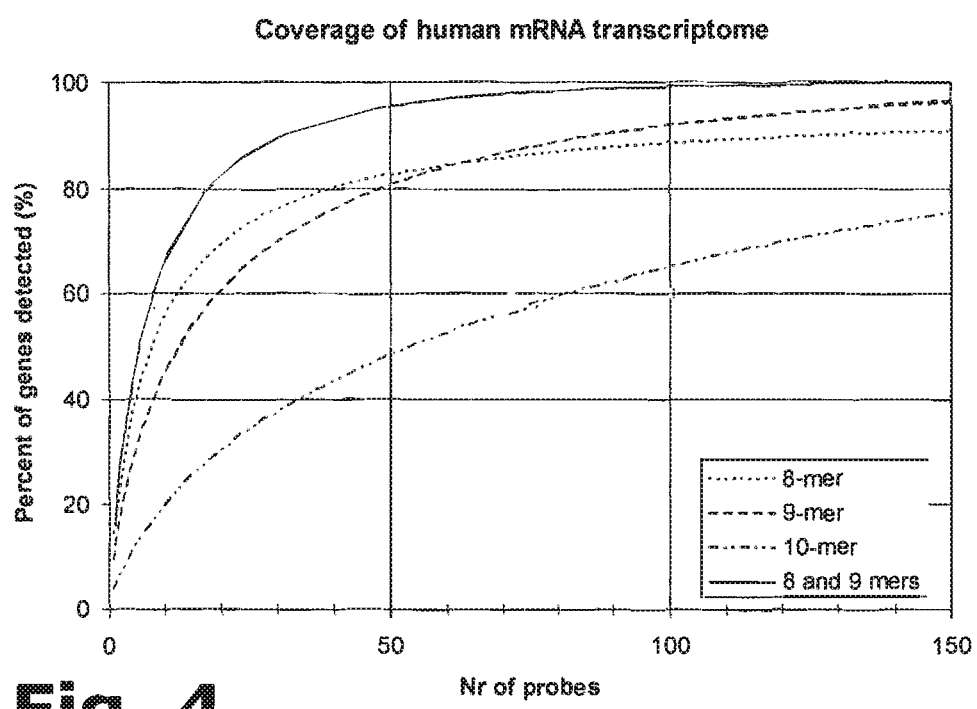
FIG. 4 shows the theoretical coverage of the human transcriptome by a selection of hyper-abundant oligonucleotides of a given length. The graphs show the percentage of approximately 38.000 human mRNA sequences that can be detected by an increasing number of well-chosen short multi-probes of different length. The graph illustrates the theoretical coverage of the human transcriptome by optimally chosen (i.e. hyper-abundant, non-self complementary and thermally stable) short multi-probes of different lengths. The Homo sapiens transcriptome sequence was obtained from European Bioinformatics Institute (EMBL-EBI). A region of 1000 nt proximal to the 3' end of each mRNA sequence was used for the analysis (from 50 nt to 1050 nt upstream from the 3' end). As the amplification of each sequence is by PCR both strands of the amplified duplex was considered a valid target for multi-probes in the probe library. Probe sequences that even with LNA substitutions have inadequate Tm, as well as self-complementary probe sequences are excluded.
Figure 9:
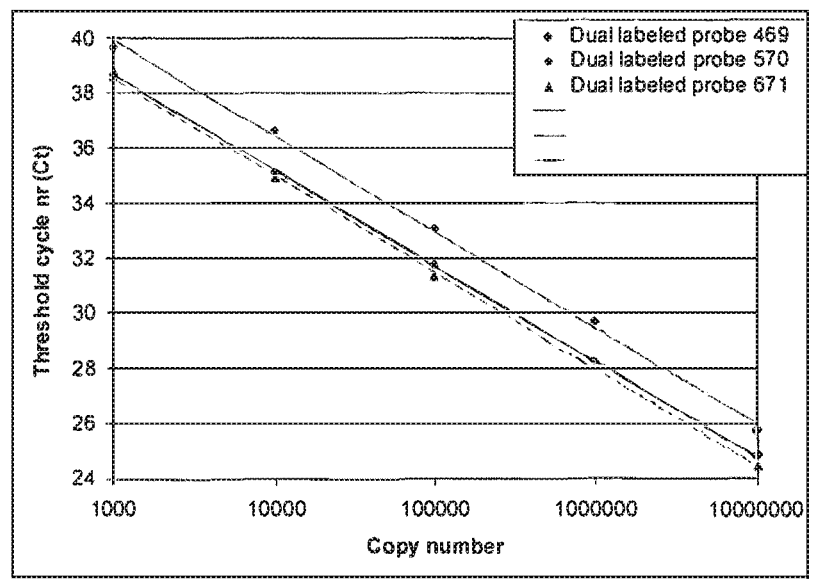
FIG. 9 shows a calibration curve for three different 9-mer multi-probes using a dual labelled probe assay principle. Detection of different copy number levels of the SSA4 cDNA by the three dual labelled probes. The threshold cycle nr defines the cycle number at which signal was first detected for the respective PCR. Slope (a) and correlation coefficients ($R^2$) of the three linear regression lines are: a=-3.456 & $R^2$=0.9999 (Dual-labelled-469), a=-3.468 & $R^2$=0.9981 (Dual-labelled-570), and a=-3.499 & $R^2$=0.9993 (Dual-labelled-671).

Especially interesting SBC nucleobases are 2,6-diaminopurine (A', also called D) together with 2-thio-uracil (U', also called $^{25}$U)(2-thio-4-oxo-pyrimidine) and 2-thio-thymine (T', also called $^{25}$T)(2-thio-4-oxo-5-methyl-pyrimidine). FIG. 4 illustrates that the pairs A-$^{25}$T and D-T have 2 or more than 2 hydrogen bonds whereas the D-$^{25}$T pair forms a single (unstable) hydrogen bond. Likewise the SBC nucleobases pyrrolo-[2,3-d]pyrimidine-2(3H)-one (C', also called PyrroloPyr) and hypoxanthine (G', also called I)(6-oxo-purine) are shown in FIG. 9 where the pairs Pyrrolo-Pyr-G and C—I have 2 hydrogen bonds each whereas the PyrroloPyr-I pair forms a single hydrogen bond.

By "SBC LNA oligorner" is meant a "LNA oligomer" containing at least one "LNA unit" where the nucleobase is a "SBC nucleobase", By "LNA unit with an SBC nucleobase" is meant a "SBC LNA monomer", Generally speaking SBC LNA oligomers include oligomers that besides the SBC LNA monomer(s) contain other modified or naturally-occurring nucleotides or nucleo-sides. By "SBC monomer" is meant a non-LNA monomer with a SBC nucleobase. By "isose-quential oligonucleotide" is meant an oligonucleotide with the same sequence in a Watson-Crick sense as the corresponding modified oligonucleotide e.g., the sequences agTtcATg is equal to agTscD$^{25}$Ug where s is equal to the SBC DNA monomer 2-thio-t or 2-thio-u, D is equal to the SBC LNA monomer LNA-D and $^{25}$U is equal to the SBC LNA monomer LNA 25U.

As used herein, the terms "nucleic acid", "polynucleotide" and "oligonucleotide" refer to primers, probes, oligomer fragments to be detected, oligomer controls and unlabelled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 3 nucleotides, preferably at least about 6 nucleotides, and more preferably at least about 8- 30 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5', phosphate of one mononucleotide pentose ring is attached to the 3' oxygen of its neighbour in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have a 5' and 3' ends.

When two different, non-overlapping oligonucleotides anneal to different regions of the same linear complementary nucleic acid sequence, the 3' end of one oligonucleotide points toward the 5' and of the other; the former may be called the "upstream" oligonucleotide and the latter the "downstream" oligonucleotide.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein, the terms "PCR reaction", "PCR amplification", "PCR" and "real-time PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification (NASBA™, Cangene, Mississauga, Ontario) and Q Beta Replicase systems. The products formed by said amplification reaction may or may not be monitored in real time or only after the reaction as an end point measurement.

The complement of a nucleic acid sequence as used herein refers to an oligonucleotide which, when aligned with the nucleic acid sequence such that the 5' end of one sequence is paired with the 3' end of the other, is in "antiparallel association," Bases not commonly found in natural nucleic acids may be included in the nucleic acids of the present invention include, for example, inosine and 7-deazaguanine. Complementarity may not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

As used herein, the term "probe" refers to a labelled oligonucleotide, which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. Generally the 3' terminus of the probe will be "blocked" to prohibit incorporation of the probe into a primer extension product. "Blocking" may be achieved by using non-complementary bases or by adding a chemical moiety such as biotin or even a phosphate group to the 3' hydroxyl of the last nucleotide, which may, depending upon the selected moiety, may serve a dual purpose by also acting as a label.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetric, X-ray diffraction or absorption, magnetism, enzymatic activity, and the like.

As defined herein, "5'→3' nuclease activity" or "5' to 3' nuclease activity" refers to that activity of a template-specific nucleic acid polymerase including either a 5'→3' exonuclease activity traditionally associated with some DNA polymerases whereby nucleotides are removed from the 5' end of an oligonucleotide in a sequential manner, (i.e., E. coli DNA polymerase I has this activity whereas the Klenow fragment does not), or a 5'→3' endonuclease activity wherein cleavage occurs more than one nucleotide from the 5' end, or both.

As used herein, the term "thermo stable nucleic acid polymerase" refers to an enzyme which is relatively stable to heat when compared, for example, to nucleotide polymerases from E. coli and which catalyzes the polymerization of nucleosides. Generally, the enzyme will initiate synthesis at the 3'-end of the primer annealed to the target sequence, and will proceed in the 5'-direction along the template, and if possessing a 5' to 3' nuclease activity, hydrolyzing or displacing intervening, annealed probe to release both labelled and unlabelled probe fragments or intact probe, until synthesis terminates. A representative thermo stable enzyme isolated from *Thermus aquaticus* (Taq) is described in U.S. Pat. No. 4,889,818 and a method for using it in conventional PCR is described in Saiki et al., (1988), Science 239:487.

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyl-adenine, 7-deazaxanthine, 7-deazaguanine, $N^4,N^4$-ethano-cytosin, $N^6,N^6$-ethano-2,6-diaminopurine, 5-methylcytosine, 5-($C^3$-$C^6$)-alkynyl-cytosine, 5-fluorouracil, 5-bromouracil, pseudoisocytosine, 2-hydroxy-5-methyl-4-triazolopy-ridin, isocytosine, isoguanine, inosine and the "non-naturally occurring" nucleobases described in Benner et al., U.S. Pat. No. 5,432,272 and Susan M. Freier and Karl-Heinz Altmann, *Nucleic Add Research*,25: 4429-4443, 1997. The term "nucleobase" thus includes not only the known purine and pyrimidine heterocycles, but also heterocyclic analogues and tautomers thereof. Further naturally and non naturally occurring nucleobases include those disclosed in U.S. Pat. No. 3,687,808; in chapter 15 by Sanghvi, in *Antisense Research and Application*, Ed. S. T. Crooke and B. Lebleu, CRC Press, 1993; in Englisch, et al., *Angewandte Chemie, International Edition*, 30: 613-722, 1991 (see, especially pages 622 and 623, and in the Concise Encyclopedia of Polymer Science and Engineering, I I. Kroschwitz Ed., John Wiley & Sons, pages 858-859, 1990, Cook, *Anti-Cancer DrugDesign* 6: 585-607, 1991, each of which are hereby incorporated by reference in their entirety).

The term "nucleosidic base" or "nucleobase analogue" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole a 5-nitroindole. Other preferred compounds include pyrene and pyridyloxazole derivatives, pyrenyl, pyrenylmethylglycerol derivatives and the like. Other preferred universal bases include, pyrrole, diazole or triazole derivatives, including those universal bases known in the art.

By "universal base" is meant a naturally-occurring or desirably a non-naturally occurring compound or moiety that can pair with a natural base (e.g., adenine, guanine, cytosine, uracil, and/or thymine), and that has a $T_m$ differential of 15, 12, 10, 8, 6, 4, or 2° C. or less as described herein.

By "oligonucleotide," "oligomer," or "oligo" is meant a successive chain of monomers (e.g., glycosides of heterocyclic bases) connected via internucleoside linkages. The linkage between two successive monomers in the oligo consist of 2 to 4, desirably 3, groups/atoms selected from —$CH_2$—, —O—, —S—, —$NR^H$—, >C=O, >C=$NR^H$, >C=S, —Si(R")$_2$—, —SO—, —(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=(including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, -$NR^H$—CO—O—, —$NR^H$—, —$NR^H$—CS—$NR^H$—, —$NR^H$—C(=$NR^H$)—$NR^H$—, —$NR^H$—CO—$CH_2$—$NR^H$—, —O—CH—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$NR^H$—, —CH=N—O—, —$CH_2$—$NR^H$—O—, —$CH_2$—O—N=(including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=(including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(S)$_2$—S—, P(S)$_2$—O—, —S—P(O)$_2$—O—, —S—P(O,S)—O—, —S—P(S)$_2$—O—, —O—P(O)$_2$—S—, —O—P(O)$_2$—O—, —O—P(O,S)—O—, —O—S—P(O)$_2$—S—, —S—P(O,S)—S—, —S—P(S)$_2$—S—, —O—PO(R")—O—, —O—PO(OCH$_3$)—O—, —O—PO(OCH$_2$CH$_2$S—R)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,$NR^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl, are especially desirable. Further illustrative examples are given in Mesmaeker et. *Current Opinion in Structural Biology* 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring as substituent p* at the 3'-position, whereas the right-hand side is bound to the 5'-position of a preceding monomer.

By "LNA unit" is meant an individual LNA monomer (e.g., an LNA nucleoside or LNA nucleotide) or an oligomer (e.g., an oligonucleotide or nucleic acid) that includes at least one LNA monomer. LNA units as disclosed in WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA units and their method of synthesis also are disclosed in WO 00/47599, U.S. Pat. Nos. 6,043,060, 6,268,490, PCT/JP98/00945, WO 0107455, WO 0100641, WO 9839352, WO 0056746, WO 0056748, WO 0066604, Morita et al., *Bioorg. Med. Chem. Lett.* 12(1):73-76, 2002; Hakansson et al., *Bioorg. Med. Chem, Lett.* 11(7):935-938, 2001; Koshkin et al., *J. Org. Chem.* 66(25):8504-8512, 2001; Kvaerno et al., *J. Org. Chem.* 66(16):5498-5503, 2001; Hakansson et al., *J. Org. Chem.* 65(17):5161-5166, 2000; Kvaerno et al., *J. Org. Chem.* 65(17):5167-5176, 2000; Pfundheller et al., *Nucleosides Nucleotides* 18(9):2017-2030, 1999; and Kumar et al., Bioorg, Med. Chem. Lett. 8(16):2219-2222, 1998.

Preferred LNA monomers, also referred to as "oxy-LNA" are LNA monomers which include bicyclic compounds as disclosed in PCT Publication WO 03/020739 wherein the bridge between $R^{4'}$ and $R^{2'}$ as shown in formula (I) below together designate —$CH_2$—O—(methyloxy LNA) or —$CH_2$—$CH_2$—O—(ethyloxy LNA, also designated ENA).

Further preferred LNA monomers are designated "thio-LNA" or "amino-LNA" including bicyclic structures as disclosed in WO 99/14226, wherein the heteroatom in the bridge between $R^{4'}$ and $R^{2'}$ as shown in formula (I) below together designate —$CH_2$—S—, —$CH_2$—$CH_2$—S—, —$CH_2$—NH— or —$CH_2$—$CH_2$—NH—.

By "LNA modified oligonucleotide" is meant a oligonucleotide comprising at least one LNA monomeric unit of formula (I), described infra, having the below described illustrative examples of modifications:

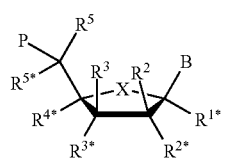

(I)

wherein X is selected from —O—, —S—, —N($R^N$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$).

B is selected from a modified base as discussed above e.g. an optionally substituted carbocyclic aryl such as optionally substituted pyrene or optionally substituted pyrenylmethyl-glycerol, or an optionally substituted heteroalicyclic or optionally substituted heteroaromatic such as optionally substituted pyridyloxazole, optionally substituted pyrrole, optionally substituted diazole or optionally substituted triazole moieties; hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

P designates the radical position for an internucleoside linkage to a succeeding monomer, or a 5'-terminal group, such internucleoside linkage or 5'-terminal group optionally including the substituent $R^5$. One of the substituents $R^2$, $R^{2*}$, $R^3$, and $R^{3*}$ is a group P* which designates an internucleoside linkage to a preceding monomer, or a 2'/3'-terminal group. The substituents of $R^{1*}$, $R^{4*}$, $R^5$, $R^{5*}$, $R^6$, $R^{6*}$, $R^7$, $R^{7*}$, $R^N$, and the ones of $R^2$, $R^{2*}$, $R^3$, and $R^{3*}$ not designating P* each designates a biradical comprising about 1-8 groups/atoms selected from —C($R^aR^b$)—, —C($R^a$)=C($R^a$)—, —C($R^a$)=N—, —C($R^a$)—O—, —O—, —Si($R^a$)$_2$—, —C($R^a$)—S, —S—, —$SO_2$—, —C($R^a$)—N($R^b$)—, —N($R^a$)—, and >C=Q, wherein Q is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, hetero-aryloxycarbonyl, heteroaryloxy, heteroarylcarbonyl, amino, mono- and di($C_{1-6}$-alky)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=$CH_2$), and wherein two non-geminal or geminal substituents selected from $R^a$, $R^b$, and any of the substituents $R^{1*}$, $R^2$, $R^{2*}$, $R^3$, $R^{3*}$, $R^4$, $R^5$, $R^{5*}$, $R^6$ and $R^{6*}$, $R^7$, and $R^{7*}$ which are present and not involved in P, P* or the biradical(s) together may form an associated biradical selected from biradicals of the same kind as defined before; the pair(s) of non-geminal substituents thereby forming a mono- or bicyclic entity together with (i) the atoms to which said non-geminal substituents are bound and (ii) any intervening atoms.

Each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P* or the biradical(s), is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a Spiro biradical consisting of a 1-5 carbon atom(s) alkylene chain which is optionally interrupted and/or terminated by one or more heteroatoms/groups selected from —O—, —S—, and —(N$R^N$)— where $R^N$ is selected from hydrogen and $C_{1-6}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxy-carbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkyl-thio, amidino, amino, carbamoyl, sulfamoyl, alkene, alkyne, protecting groups (e.g., silyl, 4,4'-dimethoxytrityl, monornethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

It is understood that references herein to a nucleic acid unit, nucleic acid residue, LNA unit, or similar term are inclusive of both individual nucleoside units and nucleotide units and nucleoside units and nucleotide units within an oligonucleotide.

A "modified base" or other similar term refers to a composition (e.g., a non-naturally occurring nucleobase or nucleosidic base), which can pair with a natural base (e.g., adenine, guanine, cytosine, uracil, and/or thymine) and/or can pair with a non-naturally occurring nucleobase or nucleosidic base. Desirably, the modified base provides a $T_m$ differential of 15, 12, 10, 8, 6, 4, or 2° C. or less as described herein. Exemplary modified bases are described in EP 1 072 679 and WO 97/12896.

The term "chemical moiety" refers to a part of a molecule. "Modified by a chemical moiety" thus refer to a modification of the standard molecular structure by inclusion of an unusual chemical structure. The attachment of said structure can be covalent or non-covalent.

The term "inclusion of a chemical moiety" in an oligonucleotide probe thus refers to attachment of a molecular structure. Such as chemical moiety include but are not limited to covalently and/or non-covalently bound minor groove binders (MGB) and/or intercalating nucleic acids (INA) selected from a group consisting of asymmetric cyanine dyes, DAPI, SYBR Green I, SYBR Green II, SYBR Gold, PicoGreen, thiazole orange, Hoechst 33342, Ethidium Bromide, 1—O—(1-pyreny)methyl)glycerol and Hoechst 33258. Other chemical moieties include the modified nucleobases, nucleosidic bases or LNA modified oligonucleotides.

The term "Dual labelled probe" refers to an oligonucleotide with two attached labels. In one aspect, one label is attached to the 5' end of the probe molecule, whereas the other label is attached to the 3' end of the molecule. A particular aspect of the invention contain a fluorescent molecule attached to one end and a molecule which is able to quench this fluorophore by Fluorescence Resonance Energy Transfer (FRET) attached to the other end, 5' nuclease assay probes and some Molecular Beacons are examples of Dual labelled probes.

The term "5' nuclease assay probe" refers to a dual labelled probe which may be hydrolyzed by the 5'-3' exonuclease activity of a DNA polymerase, A 5' nuclease assay probes is not necessarily hydrolyzed by the 5'-3' exonuclease activity of a DNA polymerase under the conditions employed in the particular PCR assay. The name "5' nuclease assay" is used regardless of the degree of hydrolysis observed and does not indicate any expectation on behalf of the experimenter. The term "5' nuclease assay probe" and "5' nuclease assay" merely refers to assays where no particular care has been taken to avoid hydrolysis of the involved probe. "5' nuclease assay probes" are often referred to as a "TaqMan assay probes", and the "5' nuclease assay" as "TaqMan assay". These names are used interchangeably in this application.

The term "oligonucleotide analogue" refers to a nucleic acid binding molecule capable of recognizing a particular target nucleotide sequence. A particular oligonucleotide analogue is peptide nucleic acid (PNA) in which the sugar phosphate backbone of an oligonucleotide is replaced by a protein like backbone. In PNA, nucleobases are attached to the uncharged polyamide backbone yielding a chimeric pseudopeptide-nucleic acid structure, which is homomorphous to nucleic acid forms.

The term "Molecular Beacon" refers to a single or dual labelled probe which is not likely to be affected by the 5'-3' exonuclease activity of a DNA polymerase. Special modifications to the probe, polymerase or assay conditions have been made to avoid separation of the labels or constituent nucleotides by the 5'-3' exonuclease activity of a DNA polymerase. The detection principle thus rely on a detectable difference in label elicited signal upon binding of the molecular beacon to its target sequence. In one aspect of the invention the oligonucleotide probe forms an intramolecular hairpin structure at the chosen assay temperature mediated by complementary sequences at the 5'- and the 3'-end of the oligonucleotide. The oligonucleotide may have a fluorescent molecule attached to one end and a molecule attached to the other, which is able to quench the fluorophore when brought into close proximity of each other in the hairpin structure. In another aspect of the invention, a hairpin structure is not formed based on complementary structure at the ends of the probe sequence instead the detected signal change upon binding may result from interaction between one or both of the labels with the formed duplex structure or from a general change of spatial conformation of the probe upon binding— or from a reduced interaction between the labels after binding. A particular aspect of the molecular beacon contain a number of LNA residues to inhibit hydrolysis by the 5'-3' exonuclease activity of a DNA polymerase.

The term "multi-probe" as used herein refers to a probe which comprises a recognition segment which is a probe sequence sufficiently complementary to a recognition sequence in a target nucleic acid molecule to bind to the sequence under moderately stringent conditions and/or under conditions suitable for PCR, 5' nuclease assay and/or Molecular Beacon analysis (or generally any FRET-based method). Such conditions are well known to those of skill in the art. Preferably, the recognition sequence is found in a plurality of sequences being evaluated, e.g., such as a transcriptome. A multi-probe according to the invention may comprise a non-natural nucleotide ("a stabilizing nucleotide") and may have a higher binding affinity for the recognition sequence than a probe comprising an identical sequence but without the stabilizing modification. Preferably, at least one nucleotide of a multi-probe is modified by a chemical moiety (e.g., covalently or otherwise stably associated with during at least hybridization stages of a PCR reaction) for increasing the binding affinity of the recognition segment for the recognition sequence.

As used herein, a multi-probe with an increased "binding affinity" for a recognition sequence than a probe which comprises the same sequence but which does not comprise a stabilizing nucleotide, refers to a probe for which the association constant ($K_a$) of the probe recognition segment is higher than the association constant of the complementary strands of a double-stranded molecule. In another preferred embodiment, the association constant of the probe recognition segment is higher than the dissociation constant ($K_d$) of the complementary strand of the recognition sequence in the target sequence in a double stranded molecule.

A "multi-probe library" or "library of multi-probes" comprises a plurality of multi-probes, such that the sum of the probes in the library are able to recognise a major proportion of a transcriptome, including the most abundant sequences, such that about 60%, about 70%, about 80%, about 85%, more preferably about 90%, and still more preferably 95%, of the target nucleic acids in the transcriptome, are detected by the probes.

Monomers are referred to as being "complementary" if they contain nucleobases that can form hydrogen bonds according to Watson-Crick base-pairing rules (e.g. G with C, A with T or A with U) or other hydrogen bonding motifs such as for example diaminopurine with T, inosine with C, pseudoisocytosine with G, etc.

The term "succeeding monomer" relates to the neighboring monomer in the 5'-terminal direction and the "preceding monomer" relates to the neighboring monomer in the 3'-terminal direction.

As used herein, the term "target population" refers to a plurality of different sequences of nucleic acids, for example the genome or other nucleic acids from a particular species including the transcriptome of the genome, wherein the transcriptome refers to the complete collection of transcribed elements of the genome of any species. Normally, the number of different target sequences in a nucleic acid population is at least 100, but as will be clear the number is often much higher (more than 200, 500, 1000, and 10000— in the case where the target population is a eukaryotic tran As used herein, the term "target nucleic acid" refers to any relevant nucleic acid of a single specific sequence, e. g., a biological nucleic acid, e. g., derived from a patient, an animal (a human or non-human animal), a plant, a bacteria, a fungi, an archae, a cell, a tissue, an organism, etc. For example, where the target nucleic acid is derived from a bacteria, archae, plant, non-human animal, cell, fungi, or non-human organism, the method optionally further comprises selecting the bacteria, archae, plant, non-human animal, cell, fungi, or non-human organism based upon detection of the target nucleic acid. In one embodiment, the target nucleic acid is derived from a patient, e. g., a human patient. In this embodiment, the invention optionally further includes selecting a treatment, diagnosing a disease, or diagnosing a genetic predisposition to a disease, based upon detection of the target nucleic acid.

As used herein, the term "target sequence" refers to a specific nucleic acid sequence within any target nucleic acid.

The term "stringent conditions", as used herein, is the "stringency" which occurs within a range from about $T_m$-5° C. (5° C. below the melting temperature ($T_m$) of the probe) to about 20° C. to 25° C. below $T_m$. As will be understood by those skilled in the art, the stringency of hybridization may be altered in order to identify or detect identical or related polynucleotide sequences. Hybridization techniques are generally described in *Nucleic Acid Hybridization, A Practical Approach*, Ed. Hames, B. D. and Higgins, S. J., IRL Press, 1985; Gall and Pardue, *Proc. Natl. Acad. Sd., USA* 63: 378-383, 1969; and John, et al. *Nature* 223: 582-587, 1969, Multi-Probes Referring now to FIG. 1B, a multi-probe according to the invention is preferably a short sequence probe which binds to a recognition sequence found in a plurality of different target nucleic acids, such that the multi-probe specifically hybridizes to the target nucleic acid but do not hybridize to any detectable level to nucleic acid molecules which do not comprise the recognition sequence, Preferably, a collection of multi-probes, or multi-probe library, is able to recognize a major proportion of a transcriptome, including the most abundant sequences, such as about 60%, about 70%, about 80%, about 85%, more preferably about 90%, and still more preferably 95%, of the target nucleic acids in the transcriptome, are detected by the probes, A multi-probe according to the invention comprises a "stabilizing modification" e.g. such as a non-natural nucleotide ("a stabilizing nucleotide") and has higher binding affinity for the recognition sequence than a probe comprising an identical sequence but without the stabilizing sequence. Preferably, at least one nucleotide of a multi-probe is modified by a chemical moiety (e.g., covalently or otherwise stably associated with the probe during at least hybridization stages of a PCR reaction) for increasing the binding affinity of the recognition segment for the recognition sequence.

In one aspect, a multi-probe of from 6 to 12 nucleotides comprises from 1 to 6 or even up to 12 stabilizing nucleotides, such as LNA nucleotides. An LNA enhanced probe library contains short probes that recognize a short recognition sequence (e.g., 8-9 nucleotides). LNA nucleobases can comprise α-LNA molecules (see, e.g., WO 00/66604) or xylo-LNA molecules (see, e.g., WO 00/56748).

In one aspect, it is preferred that the $T_m$ of the multi-probe when bound to its recognition sequence is between about 55° C. to about 70° C.

In another aspect, the multi-probes comprise one or more modified nucleobases. Modified base units may comprise a cyclic unit (e.g. a carbocyclic unit such as pyrenyl) that is joined to a nucleic unit, such as a 1'-position of furasonyl ring through a linker, such as a straight of branched chain alkylene or alkenylene group, Alkylene groups suitably having from 1 (i.e., —$CH_2$—) to about 12 carbon atoms, more typically 1 to about 8 carbon atoms, still more typically 1 to about 6 carbon atoms. Alkenylene groups suitably have one, two or three carbon-carbon double bounds and from 2 to about 12 carbon atoms, more typically 2 to about 8 carbon atoms, still more typically 2 to about 6 carbon atoms.

Multi-probes according to the invention are ideal for performing such assays as real-time PCR as the probes according to the invention are preferably less than about 25 nucleotides, less than about 15 nucleotides, less than about 10 nucleotides, e.g., 8 or 9 nucleotides. Preferably, a multi-probe can specifically hybridize with a recognition sequence within a target sequence under PCR conditions and preferably the recognition sequence is found in at least about 50, at least about 100, at least about 200, at least about 500 different target nucleic acid molecules. A library of multi-probes according to the invention will comprise multi-probes, which comprise non-identical recognition sequences, such that any two multi-probes hybridize to different sets of target nucleic acid molecules. In one aspect, the sets of target nucleic acid molecules comprise some identical target nucleic acid molecules, i.e., a target nucleic acid molecule comprising a gene sequence of interest may be bound by more than one multi-probe. Such a target nucleic acid molecule will contain at least two different recognition sequences which may overlap by one or more, but less than x nucleotides of a recognition sequence comprising x nucleotides.

In one aspect, a multi-probe library comprises a plurality of different multi-probes, each different probe localized at a discrete location on a solid substrate. As used herein, "localize" refers to being limited or addressed at the location such that hybridization event detected at the location can be traced to a probe of known sequence identity. A localized probe may or may not be stably associated with the substrate. For example, the probe could be in solution in the well of a microtiter plate and thus localized or addressed to the well. Alternatively, or additionally, the probe could be stably associated with the substrate such that it remains at a defined location on the substrate after one or more washes of the substrate with a buffer. For example, the probe may be chemically associated with the substrate, either directly or through a linker molecule, which may be a nucleic acid sequence, a peptide or other type of molecule, which has an affinity for molecules on the substrate.

Alternatively, the target nucleic acid molecules may be localized on a substrate (e.g., as a cell or cell lysate or nucleic acids dotted onto the substrate).

Once the appropriate sequences are determined, multi-LNA probes are preferably chemically synthesized using commercially available methods and equipment as described in the art (*Tetrahedron* 54: 3607-30, 1998), For example, the solid phase phosphoramidite method can be used to produce short LNA probes (Caruthers, et al., *Cold Spring Harbor Symp. Quant. Biol.* 47:411-418, 1982, Adams, et al., *J. Am. Chem. Soc.* 105: 661 (1983).

The determination of the extent of hybridization of multi-probes from a multi-probe library to one or more target sequences (preferably to a plurality of target sequences) may be carried out by any of the methods well known in the art. If there is no detectable hybridization, the extent of hybridization is thus 0. Typically, labelled signal nucleic acids are used to detect hybridization. Complementary nucleic acids or signal nucleic acids may be labelled by any one of several methods typically used to detect the presence of hybridized polynucleotides. The most common method of detection is the use of ligands, which bind to labelled antibodies, fluorophores or chemiluminescent agents. Other labels include antibodies, which can serve as specific binding pair members for a labelled ligand. The choice of label depends on sensitivity required, ease of conjugation with the probe, stability requirements, and available instrumentation.

LNA-containing-probes are typically labelled during synthesis. The flexibility of the phosphoramidite synthesis approach furthermore facilitates the easy production of LNAs carrying all commercially available linkers, fluorophores and labelling-molecules available for this standard chemistry. LNA may also be labelled by enzymatic reactions e.g. by kinasing.

Multi-probes according to the invention can comprise single labels or a plurality of labels. In one aspect, the plurality of labels comprise a pair of labels which interact with each other either to produce a signal or to produce a change in a signal when hybridization of the multi-probe to a target sequence occurs.

In another aspect, the multi-probe comprises a fluorophore moiety and a quencher moiety, positioned in such a way that the hybridized state of the probe can be distinguished from the unhybridized state of the probe by an increase in the fluorescent signal from the nucleotide. In one aspect, the multi-probe comprises, in addition to the recognition element, first and second complementary sequences, which specifically hybridize to each other, when the probe is not hybridized to a recognition sequence in a target molecule, bringing the quencher molecule in sufficient proximity to said reporter molecule to quench fluorescence of the reporter molecule. Hybridization of the target molecule distances the quencher from the reporter molecule and results in a signal, which is proportional to the amount of hybridization.

In another aspect, where polymerization of strands of nucleic acids can be detected using a polymerase with 5' nuclease activity. Fluorophore and quencher molecules are incorporated into the probe in sufficient proximity such that the quencher quenches the signal of the fluorophore molecule when the probe is hybridized to its recognition sequence. Cleavage of the probe by the polymerase with 5' nuclease activity results in separation of the quencher and fluorophore molecule, and the presence in increasing amounts of signal as nucleic acid sequences.

In the present context, the term "label" means a reporter group, which is detectable either by itself or as a part of a detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are DANSYL (5-di-methylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitro-phenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio isotopic labels, chemiluminescence labels (labels that are detectable via the emission of light during a chemical reaction), spin labels (a free radical (e.g. substituted organic nitroxides) or other paramagnetic probes (e.g. $Cu^{2+}$. $Mg^{2+}$) bound to a biological molecule being detectable by the use of electron spin resonance spectroscopy). Especially interesting examples are biotin, fluorescein, Texas Red, rhodamine, dinitrophenyl, digoxigenin, Ruthenium, Europium, Cy5, Cy3, etc.

Suitable samples of target nucleic acid molecule may comprise a wide range of eukaryotic and prokaryotic cells, including protoplasts; or other biological materials, which may harbour target nucleic acids. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney b(opsy, a bladder biopsy, a bone biopsy, a cartilage biopsy, a skin biopsy, a pancreas biopsy, a biopsy of the intestinal tract, a thymus biopsy, a mammae biopsy, a uterus biopsy, a testicular biopsy, an eye biopsy or a brain biopsy, e.g., homogenized in lysis buffer), archival tissue nucleic acids, plant cells or other cells sensitive to osmotic shock and cells of bacteria, yeasts, viruses, mycoplasmas, protozoa, rickettsia, fungi and other small microbial cells and the like.

Target nucleic acids which are recognized by a plurality of multi-probes can be assayed to detect sequences which are present in less than 10% in a population of target nucleic acid molecules, less than about 5%, less than about 1%, less than about 0.1%, and less than about 0.01% (e.g., such as specific gene sequences). The type of assay used to detect such sequences is a non-limiting feature of the invention and may comprise PCR or some other suitable assay as is known in the art or developed to detect recognition sequences which are found in less than 10% of a population of target nucleic acid molecules.

In one aspect, the assay to detect the less abundant recognition sequences comprises hybridizing at least one primer capable of specifically hybridizing to the recognition sequence but substantially incapable or hybridizing to more than about 50, more than about 25, more than about 10, more than about 5, more than about 2 target nucleic acid molecules (e.g., the probe recognizes both copies of a homozygous gene sequence), or more than one target nucleic acid in a population (e.g., such as an allele of a single copy heterozygous gene sequence present in a sample). In one preferred aspect a pair of such primers is provided and flank the recognition sequence identified by the multi-probe, i.e., are within an amplifiable distance of the recognition sequence such that amplicons of about 40-5000 bases can be produced, and preferably, 50-500 or more preferably 60-100 base amplicons are produced. One or more of the primers may be labelled.

Various amplifying reactions are well known to one of ordinary skill in the art and include, but are not limited to PCR, RT-PCR, LCR, in vitro transcription, rolling circle PCR, OLA and the like. Multiple primers can also be used in multiplex PCR for detecting a set of specific target molecules.

Figure 2:
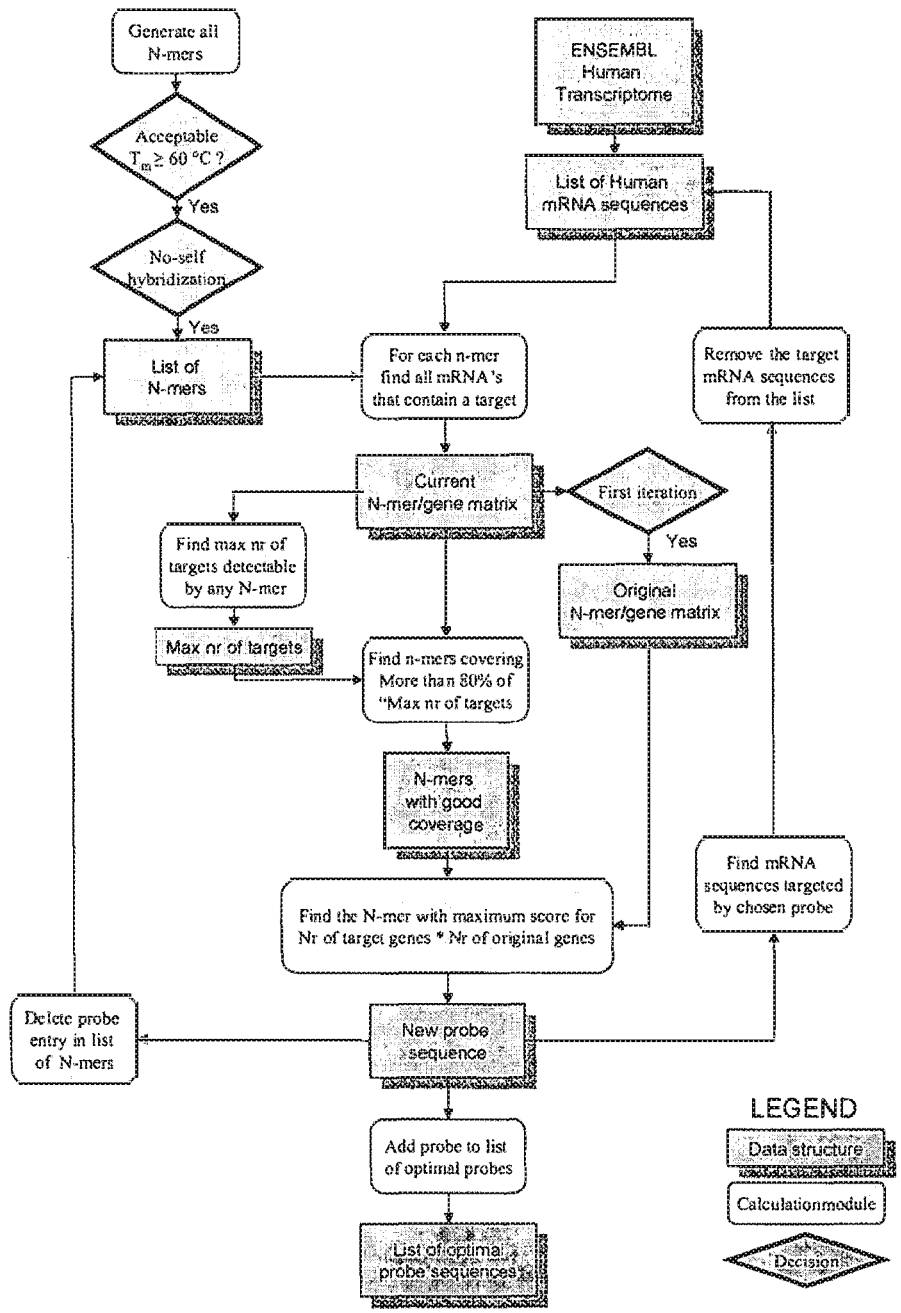
FIG. 2 is a flow chart showing a method for designing multi-probe sequences for a library according to one aspect of the invention. The method can be implemented by executing instructions provided by a computer program embedded in a computer readable medium. In one aspect, the program instructions are executed by a system, which comprises a database of sequences such as expressed sequences.

The invention further provides a method for designing multi-probes sequences for use in methods and kits according to the invention. A flow chart outlining the steps of the method is shown in FIG. 2.

In one aspect, a plurality of n-mers of n nucleotides is generated in silico, containing all possible n-mers. A subset of n-mers are selected which have a Tm≥60° C. In another aspect, a subset of these probes is selected which do not self-hybridize to provide a list or database of candidate n-mers. The sequence of each n-mer is used to query a database comprising a plurality of target sequences. Preferably, the target sequence database comprises expressed sequences, such as human mRNA sequences.

From the list of candidate n-mers used to query the database, n-mers are selected that identify a maximum number of target sequences (e.g., n-mers which comprise recognition segments which are complementary to subsequences of a maximal number of target sequences in the target database) to generate an n-meritarget sequence matrix. Sequences of n-mers, which bind to a maximum number or target sequences, are stored in a database of optimal probe sequences and these are subtracted from the candidate n-mer database. Target sequences that are identified by the first set of optimal probes are removed from the target sequence database. The process is then repeated for the remaining candidate probes until a set of multi-probes is identified comprising n-mers which cover more than about 60%, more than about 80%, more than about 90% and more than about 95% of targets sequences. The optimal sequences identified at each step may be used to generate a database of virtual multi-probes sequences. Multi-probes may then be synthesized which comprise sequences from the multi-probe database.

In another aspect, the method further comprises evaluating the general applicability of a given candidate probe recognition sequence for inclusion in the growing set of optimal probe candidates by both a query against the remaining target sequences as well as a query against the original set of target sequences. In one preferred aspect only probe recognition sequences that are frequently found in both the remaining target sequences and in the original target sequences are added to in the growing set of optimal probe recognition sequences. In a most preferred aspect this is accomplished by calculating the product of the scores from these queries and selecting the probes recognition sequence with the highest product that still is among the probe recognition sequences with 20% best score in the query against the current targets.

The invention also provides computer program products for facilitating the method described above (see, e.g., FIG. 2). In one aspect, the computer program product comprises program instructions, which can be executed by a computer or a user device connectable to a network in communication with a memory.

The invention further provides a system comprising a computer memory comprising a data-base of target sequences and an application system for executing instructions provided by the computer program product.

Kits Comprising Multi-Probes

A preferred embodiment of the invention is a kit for the characterisation or detection or quantification of target nucleic acids comprising samples of a library of multi-probes. In one aspect, the kit comprises in silica protocols for their use. In another aspect, the kit comprises information relating to suggestions for obtaining inexpensive DNA primers. The probes contained within these kits may have any or all of the characteristics described above. In one preferred aspect, a plurality of probes comprises a least one stabilizing nucleobase, such as an LNA nucleobase.

In another aspect, the plurality of probes comprises a nucleotide coupled or stably associated with at least one chemical moiety for increasing the stability of binding of the probe. In a further preferred aspect, the kit comprises a number of different probes for covering at least 60% of a population of different target sequences such as a transcriptome. In one preferred aspect, the transcriptome is a human transcriptome.

In another aspect, the kit comprises at least one probe labelled with one or more labels. In still another aspect, one or more probes comprise labels capable of interacting with each other in a FRET-based assay, i.e., the probes may be designed to perform in 5° nuclease or Molecular Beacon-based assays.

The kits according to the invention allow a user to quickly and efficiently to develop assays for many different nucleic acid targets. The kit may additionally comprise one or more re-agents for performing an amplification reaction, such as PCR.

EXAMPLES

The invention will now be further illustrated with reference to the following examples. It will be appreciated that what follows is by way of example only and that modifications to detail may be made while still falling within the scope of the invention.

In the following Examples probe reference numbers designate the LNA-oligonucleotide sequences shown in the synthesis examples below.

Example 1

Source of Transcriptome Data

The human transcriptome mRNA sequences were obtained from ENSEMBL. ENSEMBL is a joint project between EMBL-EBI and the Sanger Institute to develop a software system which produces and maintains automatic annotation on eukaryotic genomes (see, e.g., Butler, Nature 406 (6794): 333, 2000). ENSEMBL is primarily funded by the Wellcome Trust. It is noted that sequence data can be obtained from any type of database comprising expressed sequences, however, ENSEMBL is particularly attractive because it presents up-to-date sequence data and the best possible annotation for metazoan genomes. The file "Homo_sapiens.cdna.fa" was downloaded from the ENSEMBL ftp site: ftp://ftp.ensembl.org/pub/current_human/data/ on May 14, 2003. The file contains all ENSEMBL transcript predictions (i.e., 37347 different sequences). From each sequence the region starting at 50 nucleotides upstream from the 3' end to 1050 nucleotides upstream of the 3' end was extracted. The chosen set of probe sequences (see best mode below) was further evaluated against the human mRNA sequences in the Reference Sequence (RefSeq) collection from NCBI. RefSeq standards serve as the basis for medical, functional, and diversity studies;

they provide a stable reference for gene identification and characterization, mutation analysis, expression studies, polymorphism discovery, and comparative analyses. The RefSeq collection aims to provide a comprehensive, integrated, non-redundant set of sequences, including genomic DNA, transcript (RNA), and protein products, for major research organisms. Similar coverage was found for both the 37347 sequences from ENSEMBL and the 19567 sequences in the RefSeq collection, i.e., demonstrating that the type of database is a non-limiting feature of the invention.

Example 2

Calculation of a Multi-Probe Dataset (Alfa Library)

Special software running on UNIX computers was designed to calculate the optimal set of probes in a library. The algorithm is illustrated in the flow chart shown in FIG. 2.

The optimal coverage of a transcriptome is found in two steps. In the first step a sparse matrix of n_mers and genes is determined, so that the number of genes that contain a given n_mer can be found easily. This is done by running the getcover program with the –p option and a sequence file in FASTA format as input.

The second step is to determine the optimal cover with an algorithm, based on the matrix determined in the first step. For this purpose a program such as the getcover program is run with the matrix as input. However, programs performing similar functions and for executing similar steps may be readily designed by those of skill in the art.
Obtaining Good Oligonucleotide Cover of the Transcriptome.

1. All $4^n$ n-mers are generated and the expected melting temperature is calculated. n-mers with a melting temperature below 60° C. or with high self-hybridisation energy are removed from the set. This gives a list of n-mers that have acceptable physical properties.

2. A list of gene sequences representing the human transcriptome is extracted from the ENSEMBL database.

3. Start of the main loop: Given the n-mer and gene list a sparse matrix of n-mers versus genes is generated by identifying all n-mers in a given gene and storing the result in a matrix.

4. If this is the first iteration, a copy of the matrix is put aside, and named the "total n-mer/gene matrix".

5. The n-mer that covers most genes is identified and the number of genes it covers is stored as "max_gene". 6. The coverage of the remaining genes in the matrix is determined and genes with coverage of at least 80% of max_gene are stored in the "n-mer list with good coverage".

7. The optimal n-mer is the one where the product of its current coverage and the total coverage is maximal.

8. The optimal n-mer is deleted from the n-mer list (step 1).

9. The genes covered by this n-mer are deleted from the gene list (step 2).

10. The n-mer is added to the optimal n-mer list, the process is continued from step 3 until no more n-mers can be found.

The program code ("getcover" version 1.0 by Niels Tolstrup 2003) for calculation of a multi-probe dataset is listed in FIGS. 17A-17T. It consists of three proprietary modules: getcover. c, dyp. c, dyp. h
The program also incorporate four modules covered by the GNU Lesser General Public Licence:
getopt.c, getopt.h, getopt1.c, getopt_init.c
/* Copyright (C) 1987,88,89,90,91,92,93,94,95,96,98,99, 2000,2001
Free Software Foundation, Inc.
These files are part of the GNU C Library. The GNU C Library is free software; you can redistribute it and/or modify it under the terms of the GNU Lesser General Public License as published by the Free Software Foundation */

The software was compiled with aap. The main.aap file used to make the program is like-wise listed in FIGS. 17A-17T.

To run the compiled program the following command is used:
getcover-I 9-p-f<h_sap_cdna_50_1050.fasta>h_sap_cdna_50_1050_I9.stat getcover-I9-i1-d10-t60-c-n-m-s<h_sap_cdna_50_1050_I19.stat>h_sap_cdna_50_1050_I9.cover The computer program was used with instructions for implementing the algorithm described above to analyze the human transcriptome with the following parameter settings:
L89: probe length=8 or 9 nucleotides
I1: inclusion fraction=100%
d10: delta Tm required for target duplex against self duplex=10° C.
t60: minimum Tm for target duplex=60° C.
c: complementary target sequence used as well
m80: optimal probes selected among the most general probes addressing the remaining targets with the product rule and the 80% rule
n: LNA nucleotides were preferably included in the central part of the recognition segment;
and resulted in the identification of a database of multi-probe target sequences.

Target sequences in this database are exemplary optimal targets for a multi-probe library. These optimal multi-probes are listed in TABLE 1 below and comprise 5' fluorescein fluorophores and 3' Eclipse quenchers (see below).

TABLE 1

| Dual label oligonucleotide probes | | | |
|---|---|---|---|
| cagcctcc | cagagcca | agctgtga | aggaggga |
| aggaggag | ctggaagc | cagagagc | tgtggaga |
| cccaggag | cagccaga | tgaggaga | ctggggaa |
| ctccagcc | cttctggg | acagtgga | ctcctgca |
| ctcctcca | ttctgcca | acagccat | tgaggtgg |
| ctgctgcc | aggagaga | tttctcca | aaggcagc |
| ctccagca | ttcctgca | cagtggtg | ctgtggca |

TABLE 1-continued

Dual label oligonucleotide probes

| | | | |
|---|---|---|---|
| ctgctggg | tttgggga | aaagggga | agaagggc |
| cttcctgg | caggcaga | tgtgggaa | tggatgga |
| acagcagc | ctgtgcca | actgggaa | ttctgca |
| cagctcca | ttccctgg | tcacagga | cagaaggc |
| ccccaccc | aaccccat | ttcctccc | atcccaga |
| tggtggtg | ctgcccag | aggtggaa | caggtgct |
| ttcctcca | ctgaggca | tgtggaca | ctgtctcc |
| ctgctcca | ctgctggt | tggaggcc | tgctgtga |
| tggagaga | cagtgcca | atggtgaa | agctggat |
| aaggcaga | atggggaa | ctggaagg | tggagagc |
| cagccagg | agggagag | caggcagc | cttggtgg |
| cagcagga | ctctgcca | tcaggagc | caccttgg |
| ctgtgctg | ctgctgag | acacacac | cagccacc |
| agaggaga | ccctccca | catcttca | ctgtgacc |
| ctgtggct | aggaggca | cacctgca | aggggaa |
| cagtggct | cactgcca | ccagggcc | tgggacca |
| ttctccca | ctgtgtgg | cagaggca | acagggaa |
| cctggagc | ttcccagt | ctgggact | ctgggcaa |
| cccagcag | tccagtgt | ctgcctgt | ctggagga |
| ttctcctg | ctcctccc | tggaaggc | tccactgc |
| cttcctgc | ctttccca | ctgtgcct | ctgccacc |
| ccacctcc | ctctgcca | ctgtgctc | acagcctca |
| ttcctctg | cagcaggt | ctgtgagc | ctgtggtc |
| tggtgatg | ctccatcc | tcctcctc | cttcaggc |
| tgtggctg | tgctgtcc | ctcagcca | tctgggtc |
| cttctccc | tcctctcc | ctcttccc | cttggagc |
| ctgcctcc | ctctgcct | ctgggcac | ccaggctc |
| ctccttcc | ctggctgc | tgggcatc | tctctggt |
| tcctgctc | ccgccgcc | ctctggct | cttgggct |
| catcctcc | ctcctcct | tgctgggc | ctgccatc |
| aggagctg | cagcctgg | ctgctctc | cactggga |
| tcctgctg | cagcagcc | ctggagtc | tgccctga |
| ctcctcca | tgctggag | cttcagcc | ttggtggt |
| ccagccag | cttcctcc | cttccagc | ttgggact |
| cagcccag | ttcctggc | tccaggtc | ctgctgga |
| ctccacca | tcctcagc | cagcatcc | caggagct |
| ctccagcc | aggagcag | cagaggct | ctcagcct |
| tggctctg | ccaggagg | ctgccttc | ttctggct |
| caggcagc | cagcctcc | ctgggaga | ctgtctgc |
| ctgcctct | agctggag | cccagccc | ctgtccca |
| cttctgcc | ctgctgcc | cagctccc | tctgccca |
| ctgctccc | tggctgtg | ccagccgc | ctggacac |
| tggtggaa | cctggaga | cctcagcc | ttgccatc |
| agctggga | ccagggcc | tcctcttct | cttcccct |
| ctgcttcc | ccaccacc | ctggctcc | cttgggca |
| cagcaggc | tctgctgc | ccagggca | ttctggtc |
| tctggagc | cagccacc | ctccacct | ccgccgcc |
| catccagc | cagaggag | ctgcccca | cttcttctc |
| atggctgc | ctctcctc | tgggcagc | ttccctcc |
| ctcctgcc | caggagcc | ctggtctc | ttcctcaga |
| tggtggcc | tctggtcc | ctggggcc | tccaaggc |
| ctggggct | ctgtctcc | cagtggca | ttggggtc |

These hyper-abundant 9-mer and 8-mer sequences fulfil the selection criteria in FIG. 2., i.e., each probe target occurs in at least 6% of the sequences in the human transcriptome (i.e., more than 2200 target sequences each, more than 800 sequences targeted within 1000 nt proximal to the 3' end of the transcript).

They are not self complementary (i.e. unlikely to form probe duplexes).

Self score is at least 10 below I', estimate for the duplex formed with the target.

the formed duplex with their target sequence has a $T_m$ at or above 60° C.

They cover >98% of the mRNAs in the human transcriptome when combined.

Especially preferred versions of the multi-probes of table 1 are presented in the following table 1a:

TABLE 1a

One hundred LNA substituted oligonucleotides

| | | | |
|---|---|---|---|
| cAgCCTCc | cAGAGCCa | aGCTGTGa | aGGAGGGa |
| aGGAGGAg | cTGGAAGc | cAGAGAGc | tGTGGAGa |
| ccCAGGAg | cAGCCAGa | tGAGGAGa | ctGGGGAa |
| cTCCAgCc | cTTCTGGg | aCAGTGGa | cTCCtGCa |
| cTCCTCCa | tTCTGCCa | aCAGCCAt | tGAGGtGg |
| cTgCTGCc | aGGAGAGa | tTTCTCCa | aAGGCAGc |
| cTCCAGCa | tTCCTGCa | cAGTGGTg | ctGTGGCa |
| cTGCTGgg | tTTGGGGa | aAAGGGGa | aGAAGGGc |
| cTTCCTGg | cAGGCAGa | tGTGGGAa | tGGATGGa |
| aCAGCAGc | ctGTGCCa | aCTGGGAa | tTCTGGCa |
| caGCTCCa | tTCCCTGg | tCACAGGa | cAGAAGGc |
| cCCCACCc | aACCCCAt | tTCCTCCc | aTCCCAGa |
| tGGTGGTg | ctGCCCag | aGGTGGAa | cAGGtGCt |

TABLE 1a-continued

One hundred LNA substituted oligonucleotides

| | | | |
|---|---|---|---|
| tTCCTCCa | cTGAGGCa | tGTGGACa | cTGTCTCc |
| cTGCTCCa | cTGCtGGt | tGGAGgCc | tGCTGTGa |
| tGGAGAGa | cAGtGCCa | atGGTGAA | aGCTGGAt |
| aAGGCAGa | aTGGGGAa | cTGGAAGg | tGGAGAGc |
| cAGCcAGg | aGGGAGAg | cAGGcAGc | cTTGGTGg |
| cAGCAGGa | cTCtGCCa | tCAGGaGc | cACCTTgg |
| cTGTGCTg | cTGCTGAg | aCACACAC | cAgCCACc |
| aGAGGAGa | cCCtCCCa | cATCTTCA | cTGTGACc |
| ctGTGGCt | aGGAGGca | cACCtGCa | aGGGGGAa |
| caGTGGCt | cACtGCCa | cCAGgGcc | tGgGACCa |
| tTCTCCCa | cTGTGTGg | cAGAGGCa | aCAGGGAa | wherein small letters designate a DNA monomer and capital letters designate a LNA nucleotide.

>95.0% of the mRNA sequences are targeted within the 1000 nt near their 3' terminal, (position 50 to 1050 from 3' end) and >95% of the mRNA contain the target sequence for more than one probe in the library. More than 650,000 target sites for these 100 multi-probes were identified in the human transcriptome containing 37,347 nucleic acid sequences. The average number of multi-probes addressing each transcript in the transcriptome is 17.4 and the median value is target sites for 14 different probes.

The sequences noted above are also an excellent choice of probes for other transcriptomes, though they were not selected to be optimized for the particular organisms. We have thus evaluated the coverage of the above listed library for the mouse and rat genome despite the fact that the above probes were designed to detect/characterize/quantify the transcripts in the human transcriptome only. E.g. see table 2.

TABLE 2

| | Transcriptome | | |
|---|---|---|---|
| Human probe library | Human | Mouse | Rat |
| no. of mRNA sequences | 37347 | 32911 | 28904 |
| Coverage of full length mRNAs | 96.7% | 94.6% | 93.5% |
| Coverage 1000 nt near the 3'-end | 91.0% | — | — |
| At least covered by two probes | 89.8% | 80.2% | 77.0% | nt~nucleotides.

Example 3

Expected Coverage of Human Transcriptome by Frequently Occurring 9-mer Oligonucleotides Experimental pilot data (similar to FIGS. 6A-6C) indicated that it is possible to reduce the length of the recognition sequence of a dual-labelled probe for real-time PCR assays to 8 or 9 nucleotides depending on the sequence, if the probe is enhanced with LNA. The unique duplex stabilizing properties of LNA are necessary to ensure an adequate stability for such a short duplex (i.e. $T_m > 60°$ c.). The functional real-time PCR probe will be almost pure LNA with 6 to 10 LNA nucleotides in the recognition sequence. However, the short recognition sequence makes it possible to use the same LNA probe to detect and quantify the abundance of many different genes. By proper selection of the best (i.e. most common) 8 or 9-mer recognition sequences according to the algorithm depicted in FIG. 2 it is possible to get a coverage of the human transcriptome containing about 37347 mRNAs (FIG. 3).

Figure 3:
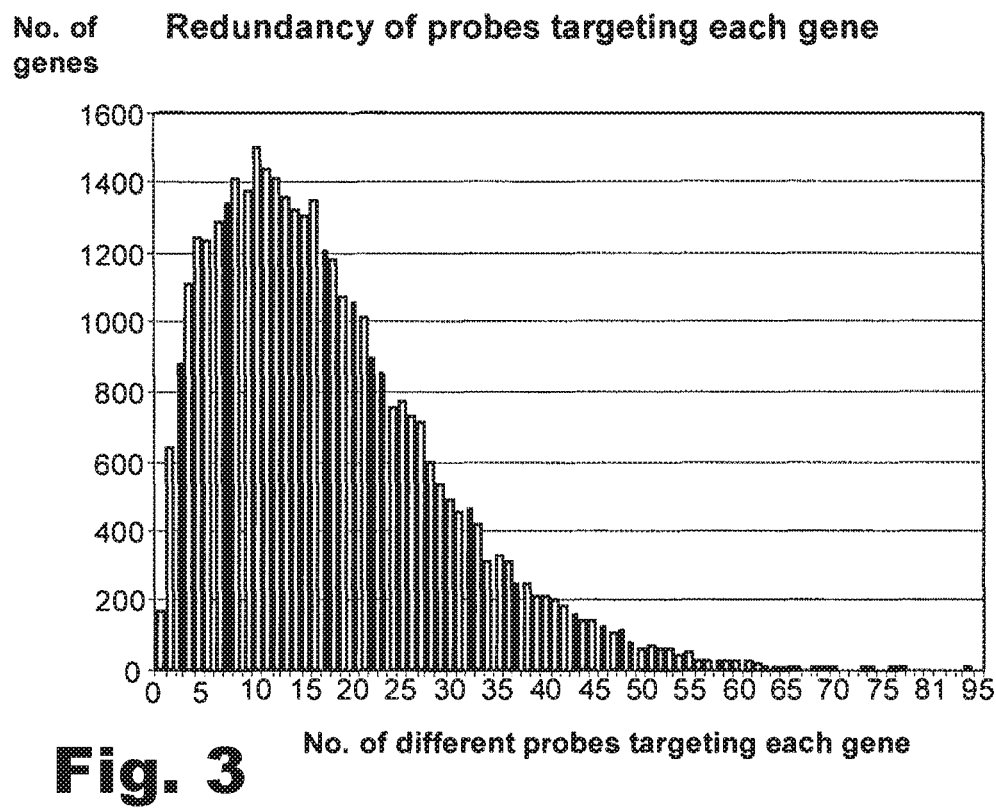
FIG. 3 is a graph illustrating the redundancy of probes targeting each gene within a 100-probe library according to one aspect of the invention. The y-axis shows the number of genes in the human transcriptome that are targeted by different number of probes in the library. It is apparent that a majority of all genes are targeted by several probes. The average number of probes per gene is 17.4.

FIG. 3 shows the expected coverage as percentage of the total number of mRNA sequences in the human transcriptome that are detectable within a 1000 nt long stretch near the 3' end of the respective sequences (i.e. the sequence from 50 nt to 1050 nt from the 3' end) by optimized probes of different lengths. The probes are required to be sufficiently stable (Tm>60 degC) and with a low propensity for forming self duplexes, which eliminate many 9-mers and even more 8-mer probe sequences.

If all probes sequences of a given length could be used as probes we would obviously get the best coverage of the transcriptome by the shortest possible probe sequences. This is indeed the case when only a limited number of probes (<55) are included in the library (FIG. 4). However, because many short probes with a low GC content have an inadequate thermal stability, they were omitted from the library. The limited diversity of acceptable 8-mer probes are less efficient at detecting low GC content genes, and a library composed of 100 different 9-mer probes consequently have a better coverage of the transcriptome than a similar library of 8-mers. However, the best choice is a mixed library composed of sequences of different lengths such as the proposed best mode library listed above. The coverage of this library is not shown in FIG. 4.

The designed probe library containing 100 of the most commonly occurring 9-mer and 8-mers, i.e., the "Human mRNA probe library" can be handled in a convenient box or microtiter plate format.

The initial set of 100 probes for human mRNAs can be modified to generate similar library kits for transcriptomes from other organisms (mouse, rat, Drosophila., C eregans, yeast, Arabidopsis, zebrafish, primates, domestic animals, etc.). Construction of these new probe libraries will require little effort, as most of the human mRNA probes may be re-used in the novel library kits (TABLE 2).

Example 4

Number of Probes in the Library that Target Each Gene

Not only does the limited number of probes in the proposed libraries target a large fraction (>98%) of the human transcriptome, but there is also a large degree of redundancy in that most of the genes (almost 95%) may be detected by more than one probe. More than 650,000 target sites have been identified in the human transcriptome (37347 genes) for the 100 probes in the best mode library shown above. This gives an average number of target sites per probe of 6782 (i.e. 18% of the transcriptome) ranging from 2527 to 12066 sequences per probe. The average number of probes capable of detecting a particular gene is 17.4, and the median value is 14. Within the library of only 100 probes we thus have at least 14 probes for more than 50% of all human mRNA sequences.

The number of genes that are targeted by a given number of probes in the library is depicted in FIG. 4.

Example 5

Design of 9-mer Probes to Demonstrate Feasibility

The SSA4 gene from yeast (*Saccharomyces cerevisiae*) was selected for the expression assays because the gene transcription level can be induced by heat shock and mutants are available where expression is knocked out. Three different 9mer sequences were selected amongst commonly occurring 9mer sequences within the human transcriptome (Table 3). The sequences were present near the 3' terminal end of 1.8 to 6.4% of all mRNA sequences within the human transcriptome. Further selection criteria were a moderate level of selfcomplementarity and a Tm of 60° C. or above. All three sequences were present within the terminal 1000 bases of the SSA4 ORF. Three 5' nuclease assay probes were constructed by synthesizing the three sequences with a FITCH fluorophore in the 5'-end and an Eclipse quencher (Epoch Biosciences) in the 3' end. The probes were named according to their position within the ORF YER103W (SSA4) where position 1201 was set to be position 1. Three sets of primer pairs were designed to produce three non-overlapping amplicons, which each contained one of the three probe sequences. Amplicons were named according to the probe sequence they encompassed.

Two Molecular Beacons were also designed to detect the SSA4 469- and the SSA4 570 sequence and named Beacon-469 and Beacon-570, respectively. The sequence of the SSA4 469 beacon was CAAGGAGAAGTTG (SED ID NO: 7, 10-mer recognition site) which should enable this oligonucleotide to form the intramolecular beacon structure with a stem formed by the LNA-LNA interactions between the 5'-CAA and the TTG-3'. The sequence of the SSA4 570 beacon was CAAGGAAAGttG (9-mer recognition site) where the intramolecular beacon structure may form between the 5'-CAA and the ttG-3'. Both the sequences were synthesized with a fluorescein fluorophore in the 5'-end and a Dabcyl quencher in the 3' end.

One SYBR Green labeled probe was also designed to detect the SSA4 570 sequence and named SYBR-Probe-570. The sequence of this probe was CAAGGAAaG. This probe was synthesized with a amino-CS linker on the 5'-end on which the fluorophore SYBR Green 101 (Molecular Probes) was attached according to the manufactures instructions. Upon hybridization to the target sequence, the linker

TABLE 3

Designed 5' nuclease assay probes and primers

| Sequence | Name of probe | Forward primer sequence | Reverse primer sequence | Amplicon length |
|---|---|---|---|---|
| aaGGAGAAG | Dual-labelled-469 | cgcgtttactttgaaaaattctg (SEQ ID NO: 1) | gcttccaatttcctggcatc (SEQ ID NO: 2) | 81 bp |
| cAAGGAAAg | Dual-labelled-570 | gcccaagatgctataaatt-ggttag (SEQ ID NO: 3) | gggtttgcaacaccttctagttc (SEQ ID NO: 4) | 95 bp |
| ctGGAGCaG | Dual-labelled-671 | tacggagctgcaggtggt (SEQ ID NO: 5) | gttgggccgttgtctggt (SEQ ID NO: 6) | 86 bp | bp-base pairs attached fluorophore should intercalate in the generated LNA-DNA duplex region causing increased fluorescence from the SYBR Green 101.

TABLE 4

SEQUENCES

| EQ Number | Name | Type | Sequence | Position in gene |
|---|---|---|---|---|
| 13992 | Dual-labelled-469 | 5' nuclease assay probe | 5'-Fluor-aaGGAGAAG-Eclipse-3' | 469-477 |
| 13994 | Dual-labelled-570 | 5' nuclease assay probe | 5'-Fluor-cAAGGAAAg-Eclipse-3' | 570-578 |
| 13996 | Dual-labelled-671 | 5' nuclease assay probe | 5'-Fluor-ctGGAGCaG-Eclipse-3' | 671-679 |
| 13997 | Beacon-469 | Molecular Beacon | 5'-Fluor-CAAGGAGAAGTTG-Dabcyl-3' (5'-Fluor-SEQ ID NO: 8-Dabcyl-3') | |
| 14148 | Beacon-570 | Molecular Beacon | 5'-Fluor-CAAGGAAAGttG-Dabcyl-3' (5'-Fluor-SEQ ID NO: 9-Dabcyl-3') | |
| 14165 | SYBR-Probe-570 | SYBR-Probe | 5'-SYBR101-NH2C6-cAAGGAAAg-3' | |
| 14012 | SSA4-469-F | Primer | cgcgtttactttgaaaaattctg (SEQ ID NO: 10) | |

TABLE 4-continued

SEQUENCES

| EQ Number | Name | Type | Sequence | Position in gene |
|---|---|---|---|---|
| 14013 | SSA4-469-R | Primer | gcttccaatttcctggcatc (SEQ ID NO: 11) | |
| 14014 | SSA4-570-F | Primer | gcccaagatgctataaattggttag (SEQ ID NO: 12) | |
| 14015 | SSA4-570-R | Primer | gggtttgcaacaccttctagttc (SEQ ID NO: 13) | |
| 14016 | SSA4-671-F | Primer | tacggagctgcaggtggt (SEQ ID NO: 14) | |
| 14017 | SSA4-671-R | Primer | gttgggccgttgtctggt (SEQ ID NO: 15) | |
| 14115 | POL5-469-F | Primer | gcgagagaaaacaagcaagg (SEQ ID NO: 16) | |
| 14116 | POL5-469-R | Primer | attcgtcttcactggcatca (SEQ ID NO: 17) | |
| 14117 | APG9-570-F | Primer | cagctaaaaatgatgacaataatgg (SEQ ID NO: 18) | |
| 14118 | APG9-570-R | Primer | attacatcatgattagggaatgc (SEQ ID NO: 19) | |
| 14119 | HSP82-671-F | Primer | gggtttgaacattgatgagga (SEQ ID NO: 20) | |
| 14120 | HSP82-671-R | Primer | ggtgtcagctggaacctctt (SEQ ID NO: 21) | |

Example 6

Synthesis, Deprotection and Purification of Dual Labelled Oligonucleotides

The dual labelled oligonucleotides EQ13992 to EQ14148 (Table 4) were prepared on an automated DNA synthesizer (Expedite 8909 DNA synthesizer, PerSeptive Biosystems, 0.2 μmol scale) using the phosphoramidite approach (Beaucage and Caruthers, Tetrahedron Lett 22: 1859-1862, 1981) with 2-cyanoethyl protected LNA and DNA phosphorarnidites, (Sinha, et al., Tetrahedron Lett.24: 5843-5846, 1983). CPG solid supports derivatized with either eclipse quencher (EQ13992-EQ13996) or dabcyl (EQ13997-EQ14148) and 5'-fluorescein phosphoramidite (GLEN Research, Sterling, Va., USA). The synthesis cycle was modified for LNA phosphoramidites (250s coupling time) compared to DNA phosphoramidites. 1H-tetrazole or 4,5-dicyanoimidazole (Proligo, Hamburg, Germany) was used as activator in the coupling step.

Figure 5:
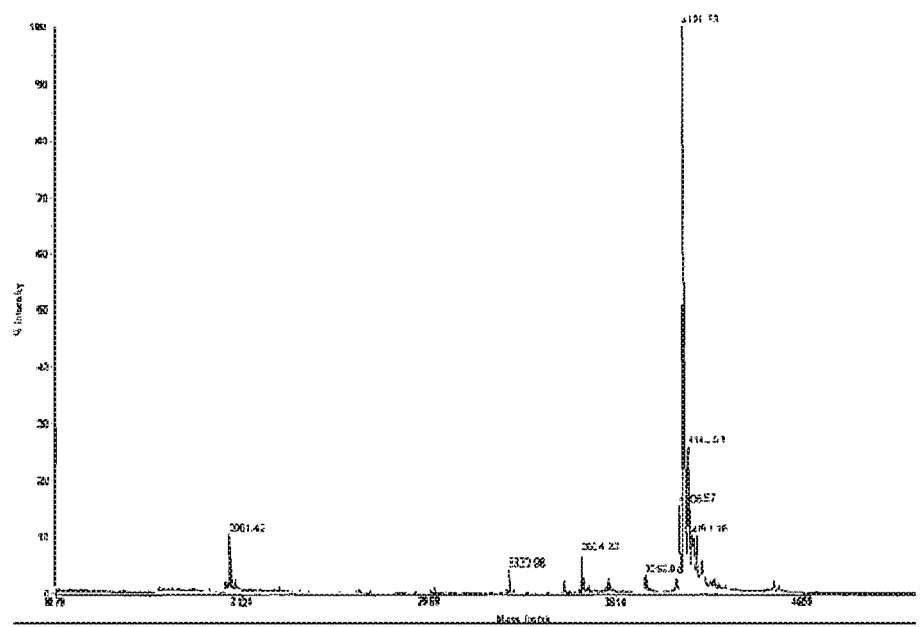
FIG. 5 shows the MALDI-MS spectrum of the oligonuclotide probe EQ13992, showing [M-H]$^-$=4121,3 Da.

The oligonucleotides were deprotected using 32% aqueous ammonia (1 h at room temperature, then 2 hours at 60° C.) and purified by HPLC (Shimadzu-SpectraChrom series; Xterra™ RP18 column, 10? m 7.8×150 mm (Waters). Buffers: A: 0.05M Triethylarnmonium acetate pH 7.4. B. 50% acetonitrile in water. Eluent: 0-25 min: 10-80% B; 25-30 min: 80% B). The composition and purity of the oligonucleotides were verified by MALDI-MS (PerSeptive Bio-system, Voyager DE-PRO) analysis, see Table 5. FIG. 5 is the MALDI-MS spectrum of EQ13992 showing [M-H]—=4121,3 Da. This is a typical MALDI-MS spectrum for the 9-mer probes of the invention.

TABLE 5

| EQ# | Sequences | MW (Calc.) | MW (Found) |
|---|---|---|---|
| 13992 | 5'-Fitc-aaGGAGAAG-EQL-3' | 4091.8 Da. | 4091.6 Da |
| 13994 | 5'-Fitc-cAAGGAAAg-EQL-3' | 4051.9 Da. | 4049.3 Da. |
| 13996 | 5'-Fitc-ctGGAGmCaG-EQL-3' | 4020.8 Da. | 4021.6 Da. |
| | 5'-Fitc-mCAAGGAGAAGTTG-dabcyl-3' | | |
| 13997 | (5'-Fitc-SEQ ID NO: 22-dabcyl-3') | 5426.3 Da. | 5421.2 Da. |

Capitals designate LNA monomers (A, G, mC, T), where mC is LNA methyl cytosine.
Small letters designate DNA monomers (a, g, c, t).
Fitc = Fluorescein; EQL = Eclipse quencher; Dabcyl = Dabcyl quencher.
MW = Molecular weight.

Example 7

Production of cDNA Standards of SSA4 for Detection with 9-mer Probes

The functionality of the constructed 9mer probes were analysed in PCR assays where the probes ability to detect different SSA4 PCR amplicons were questioned. Template for the PCR reaction was cDNA obtained from reverse transcription of cRNA produced from in vitro transcription of a downstream region of the SSA4 gene in the expression vector pTRIamp18 (Ambion). The downstream region of the SSA4 gene was cloned as follows:

PCR Amplificatiqn

Amplification of the partial yeast gene was done by standard PCR using yeast genomic DNA as template. Genomic DNA was prepared from a wild type standard laboratory strain of *Saccharomyces cerevisiae* using the Nucleon MiY DNA extraction kit (Amersham Biosciences) according to supplier's instructions. In the first step of PCR amplification, a forward primer containing a restriction enzyme site and a reverse primer containing a universal linker sequence were used. In this step 20 bp was added to the 3'-end of the amplicon, next to the stop codon. In the second step of amplification, the reverse primer was exchanged with a nested primer containing a poly-$T_{20}$ tail and a restriction enzyme site. The SSA4 amplicon contains 729 bp of the SSA4 ORF plus a 20 bp universal linker sequence and a poly-$A_{20}$ tail.

The FCR primers used were:

YER103W-For-SacI:
(SEQ ID NO: 23)
acgtgagctcattgaaactgcaggtggtattatga

YER103W-Rev-Uni:
(SEQ ID NO: 24)
gatccccgggaattgccatgctaatcaacctcttcaaccgttgg

Uni-polyT-BamHI:
(SEQ ID NO: 25)
acgtggatcctttttttttttttttttttgatccccgggaattgccatg.

plasmid DNA Constructs

The PCR amplicon was cut with the restriction enzymes, EcoRI+BamHI. The DNA fragment was ligated into the pTRIanip18 vector (Ambion) using the Quick Ligation Kit (New England Biolabs) according to the supplier's instructions and transformed into *E. coil* DH-5 by standard methods.

DNA Sequencing

To verify the cloning of the PCR amplicon, plasmid DNA was sequenced using M13 forward and M13 reverse primers and analysed on an ABI 377.

In vitro Transcription SSA4 cRNA was obtained by performing in vitro transcription with the Megascript 77 kit (Ambion) according to the supplier's instructions.

Reverse Transcription

Reverse transcription was performed with 1 µg or cRNA and 0.2 U of the reverse transcriptase Superscript II RT (Invitrogen) according to the suppliers instructions except that 20 U Superase-In (RNAse inhibitor-Ambion) was added. The produced cDNA was purified on a QiaQuick PCR purification column (Qiagen) according to the supplier's instructions using the supplied EB-buffer for elution. The DNA concentration of the eluted cDNA was measured and diluted to a concentration of SSA4 cDNA copies corresponding to $2 \times 10^7$ copies pr µL.

Example 8

Protocol for of Dual Label Probe Assays

Reagents for the dual label probe PCRs were mixed according to the following scheme (Table 6):

TABLE 6

| Reagents | Final Concentration |
| --- | --- |
| H$_2$O | |
| GeneAmp 10x PCR buffer II | 1x |
| Mg$^{2+}$ | 5.5 mM |
| DNTP | 0.2 mM |
| Dual Label Probe | 0.1 or 0.3 µM* |
| Template | 1 µL |

TABLE 6-continued

| Reagents | Final Concentration |
| --- | --- |
| Forward primer | 0.2 µM |
| Reverse primer | 0.2 µM |
| AmliTaq Gold | 2.5 U |
| Total | 50 µL |

*Final concentration of 5' nuclease assay probe 0.1 µM and Beacon/SYBR-probe 0.3 µM.

In the present experiments $2 \times 10^7$ copies of the SSA4 cDNA was added as template. Assays were performed in a DNA Engine Opticon® (MJ Research) using the following PCR cycle protocols:

TABLE 7

| 5' nuclease assays | Beacon & SYBR-probe Assays |
| --- | --- |
| 95° C. for 7 minutes | 95° C. for 7 minutes |
| & | & |
| 40 cycles of: | 40 cycles of: |
| 94° C. for 20 seconds | 94° C. for 30 seconds |
| 60° C. for 1 minute | 52° C. for 1 minute* |
| Fluorescence detection | Fluorescence detection |
| | 72° C. for 30 seconds |

*For the Beacon-570 with 9-mer recognition site the annealing temperature was reduced to 44° C.

The composition of the PCR reactions shown in Table 6 together with PCR cycle protocols listed in Table 7 will be referred to as standard 5' nuclease assay or standard Beacon assay conditions.

Example 9

Specificity of 9-mer 5' Nuclease Assay Probes

Figure 6A:
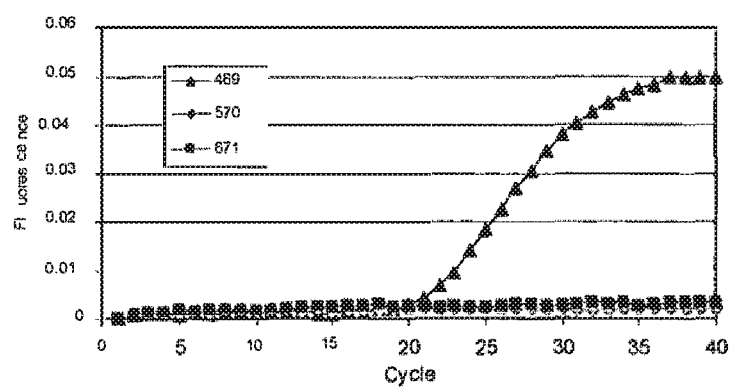
FIG. 6A, FIG. 6B, and FIG. 6C show representative real time PCR curves for 9-mer multi-probes detecting target sequences in a dual labelled probe assay. Results are from real time PCR reactions with 9 nt long LNA enhanced dual labelled probes targeting different 9-mer sequences within the same gene. Each of the three different dual labelled probes were analysed in PCRS generating either the 469, the 570 or the 671 SSA4 amplicons (each between 81 to 95 nt long). Dual labelled probe 469, 570, and 671 is shown in FIGS. 6A, 6B, and 6C, respectively. Each probe only detects the amplicon it was designed to detect. The $C_t$ values were 23.7, 23.2, and 23.4 for the dual labelled probes 469, 570, and 671, respectively. $2 \times 10^7$ copies of the SSA4 cDNA were added as template. The high similarity between results despite differences in both probe sequences and their individual primer pairs indicate that the assays are very robust.
Figure 6B:
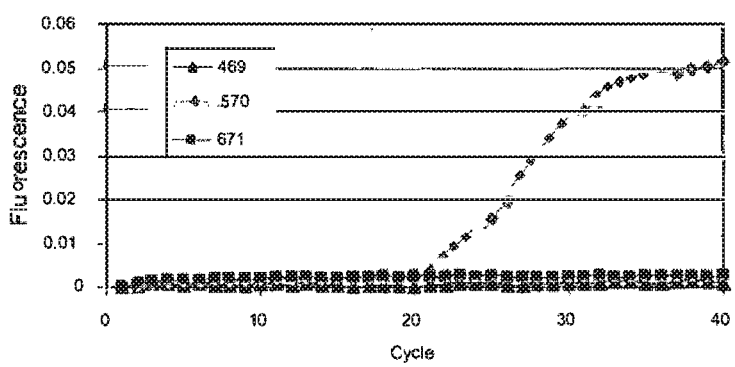
Figure 6C:
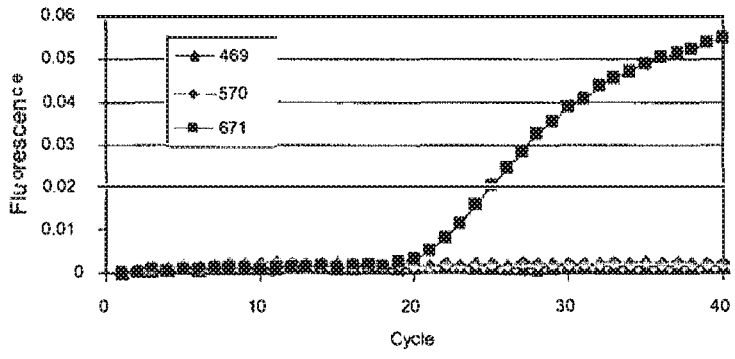

The specificity of the 5' nuclease assay probes were demonstrated in assays where each of the probes was added to 3 different PCR reactions each generating a different SSA4 PCR amplicon. As shown in FIGS. 6A-6C, each probe only produces a fluorescent signal together with the amplicon it was designed to detect (see also FIGS. 10, 11A-11C and 12). Importantly the different probes had very similar cycle threshold $C_t$ values (from 23.2 to 23.7), showing that the assays and probes have a very equal efficiency. Furthermore it indicates that the assays should detect similar expression levels when used in used in real expression assays. This is an important finding, because variability in performance of different probes is undesirable.

Example 10

Specificity of 9 and 10-mer Molecular Beacon Probes

Figure 7A:
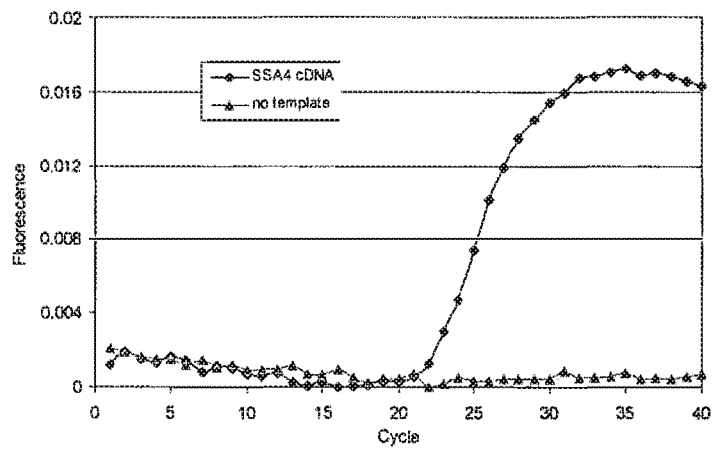
FIG. 7A and FIG. 7B show examples of real time PCR curves for Molecular Beacons with a 9-mer and a 10-mer recognition site.
Figure 7B:
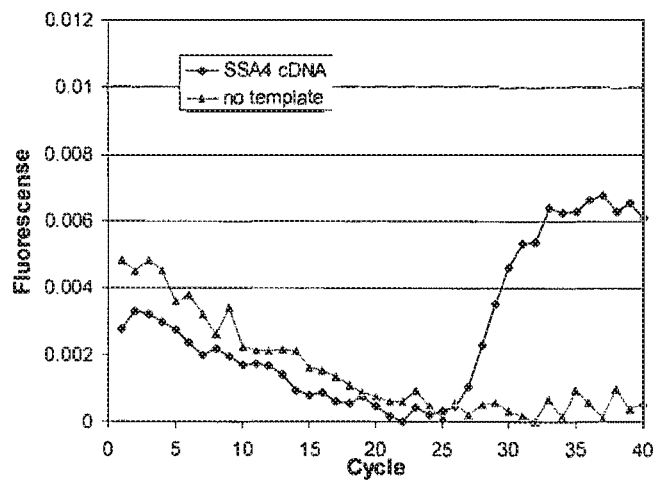

The ability to detect in real time, newly generated PCR amplicons was also demonstrated for the molecular beacon design concept. The Molecular Beacon designed against the 469 amplicon with a 10-mer recognition sequence produced a clear signal when the SSA4 cDNA template and primers for generating the 469 amplicon were present in the PCR, FIG. 7A. The observed $C_t$ value was 24.0 and very similar to the ones obtained with the 5° nuclease assay probes again indicating a very similar sensitivity of the different probes. No signal was produced when the SSA4 template was not added. A similar result was produced by the Molecular Beacon designed against the 570 amplicon with a 9-mer recognition sequence, FIG. 7B.

Example 11

Specificity of 9-mer SYBR-Probes

Figure 8:
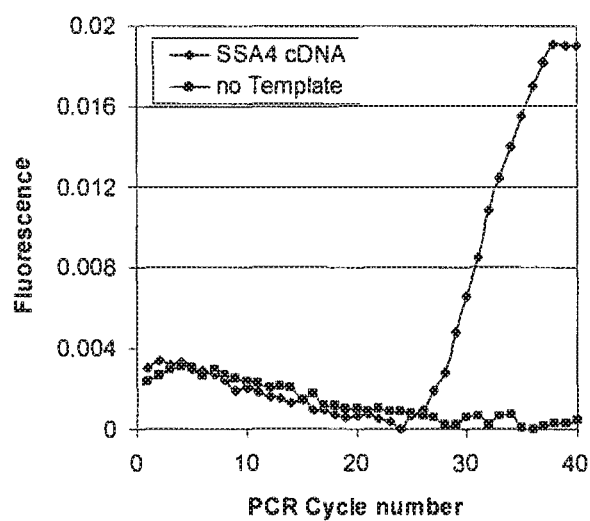
FIG. 8 shows an example of a real time PCR curve for a SYBR-probe with a 9-mer recognition site targeting the 570 SSA4 amplicon. Signal was only obtained in the sample where SSA4 cDNA was added ($2 \times 10^7$ copies), whereas no signal was detected without addition of template.

The ability to detect newly generated PCR amplicons was also demonstrated for the SYBR-probe design concept. The 9-mer SYBR-probe designed against the 570 amplicon of the SSA4 cDNA produced a clear signal when the SSA4 cDNA template and primers for generating the 570 amplicon were present in the PCR, FIG. 8. No signal was produced when the SSA4 template was not added.

Example 12

Quantification of Transcript Copy Number

The ability to detect different levels of gene transcripts is an essential requirement for a probe to perform in a true expression assay. The fulfilment of the requirement was shown by the three 5' nuclease assay probes in an assay where different levels of the expression vector derived SSA4 cDNA was added to different PCR reactions together with one of the 5' nuclease assay probes (FIG. 9). Composition and cycle conditions were according to standard 5' nuclease assay conditions.

The cDNA copy number in the PCR before start of cycling is reflected in the cycle threshold value $C_t$, i.e., the cycle number at which signal is first detected. Signal is here only defined as signal if fluorescence is five times above the standard deviation of the fluorescence detected in PCR cycles 3 to 10. The results show an overall good correlation between the logarithm to the initial cDNA copy number and the $C_t$ value (FIG. 9). The correlation appears as a straight line with slope between $-3.456$ and $-3.499$ depending on the probe and correlation coefficients between 0.9981 and 0.9999. The slope of the curves reflect the efficiency of the PCRs with a 100% efficiency corresponding to a slope of $-3.322$ assuming a doubling of amplicon in each PCR cycle. The slopes of the present PCRs indicate PCR efficiencies between 94% and 100%. The correlation coefficients and the PCR efficiencies are as high as or higher than the values obtained with DNA 5' nuclease assay probes 17 to 26 nucleotides long in detection assays of the same SSA4 cDNA levels (results not shown). Therefore these result show that the three 9-mer 5' nuclease assay probes meet the requirements for true expression probes indicating that the probes should perform in expression profiling assays

Example 13

Detection of SSA4 Transcription Levels in Yeast

Expression levels of the SSA4 transcript were detected in different yeast strains grown at different culture conditions (± heat shock). A standard laboratory strain of *Saccharomyces cerevisiae* was used as wild type yeast in the experiments described here. A SSA4 knockout mutant was obtained from EUROSCARF (accession number Y06101). This strain is here referred to as the SSA4 mutant. Both yeast strains were grown in YPD medium at 30° C. till an $OD_{600}$ of 0.8 A. Yeast cultures that were to be heat shocked were transferred to 40° C. for 30 minutes after which the cells were harvested by centrifugation and the pellet frozen at −80° C. Non-heat shocked cells were in the meantime left growing at 30° C. for 30 minutes and then harvested as above.

RNA was isolated from the harvested yeast using the FastRNA Kit (Bio 101) and the FastPrep machine according to the supplier's instructions.

Reverse transcription was performed with 5 µg of anchored oligo(dT) primer to prime the reaction on 1 µg of total RNA, and 0.2 U of the reverse transcriptase Superscript II RT (Invitrogen) according to the suppliers instructions except that 20 U Superase-In (RNAse inhibitor-Ambion) was added. After a two-hour incubation, enzyme inactivation was performed at 70° for 5 minutes. The cDNA reactions were diluted 5 times in 10 mM Tris buffer pH 8.5 and oligonucleotides and enzymes were removed by purification on a MicroSpin™ S-400 HR column (Amersham Pharmacia Biotech). Prior to performing the expression assay the cDNA was diluted 20 times. The expression assay was performed with the Dual-labelled-570 probe using standard 5' nuclease assay conditions except 2 µL of template was added. The template was a 100 times dilution of the original reverse transcription reactions. The four different cDNA templates used were derived from wild type or mutant with or without heat shock. The assay produced the expected results (FIG. 10) showing increased levels of the SSA4 transcript in heat shocked wild type yeast ($C_t$=26.1) compared to the wild type yeast that was not submitted to elevated temperature ($C_t$=30.3). No transcripts were detected in the mutant yeast irrespective of culture conditions. The difference in values of 3.5 corresponds to a 17 fold induction in the expression level of the heat shocked versus the non-heat shocked wild type yeast and this value is close to the values around 19 reported in the literature (Causton, et al. 2001). These values were obtained by using the standard curve obtained for the Dual-labelled-570 probe in the quantification experiments with known amounts of the SSA4 transcript (see FIG. 9). The experiments demonstrate that the 9-mer probes are capable of detecting expression levels that are in good accordance with published results.

Example 14

Multiple Transcript Detection with Individual 9-mer Probes

To demonstrate the ability of the three 5' nuclease assay probes to detect expression levels of other genes as well, three different yeast genes were selected in which one of the probe sequences was present. Primers were designed to amplify a 60-100 base pair region around the probe sequence. The three selected yeast genes and the corresponding primers are shown in Table.

TABLE 8

Design of alternative expression assays

| Sequence/Name | Matching Probe | Forward primer sequence | Reverse primer sequence | Amplicon length |
|---|---|---|---|---|
| YEL055C/POL5 | Dual-labelled-469 | gcgagagaaaacaagcaagg (SEQ ID NO: 26) | attcgtcttcactggcatca (SEQ ID NO: 27) | 94 bp |

TABLE 8-continued

Design of alternative expression assays

| Sequence/Name | Matching Probe | Forward primer sequence | Reverse primer sequence | Amplicon length |
|---|---|---|---|---|
| YDL149W_APG9 | Dual-labelled-570 | cagctaaaaatgatgacaataatgg (SEQ ID NO: 28) | attacatcatgattagggaatgc (SEQ ID NO: 29) | 97 bp |
| YPL240C_HSP82 | Dual-labelled-671 | gggtttgaacattgatgagga (SEQ ID NO: 30) | ggtgtcagctggaacctctt (SEQ ID NO: 31) | 88 bp |

Total cDNA derived from non-heat shocked wild type yeast was used as template for the expression assay, which was performed using standard 5' nuclease assay conditions except 2 µL of template was added. As shown in FIGS. 11A-11C, all three probes could detect expression of the genes according to the assay design outlined in Table 8. Expression was not detected with any other combination of probe and primers than the ones outlined in Table 8. Expression data are available in the literature for the SSA4, POL5, HSP82, and the APG9 (Holstege, et al. 1998). For non-heat shocked yeast, these data describe similar expression levels for SSA4 (0.8 transcript copies per cell), POL5 (0.8 transcript copies per cell) and HSP82 (1.3 transcript copies per cell) whereas APG9 transcript levels are somewhat lower (0.1 transcript 10 copies per cell).

This data is in good correspondence with the results obtained here since all these genes showed similar $C_t$ values except HSP82, which had a G value of 25.6. This suggests that the HSP82 transcript was more abundant in the strain used in these experiments than what is indicated by the literature. Agarose gel electrophoresis was performed with the PCRs shown in FIG. 11a for the Dual-labelled-469 probe. The agarose gel (FIG. 12) shows that PCR product was indeed generated in reactions where no signal was obtained and therefore the lack fluoescent signal from these reactions was not caused by failure of the PCR. Furthermore, the different length of amplicons produced in expression assays for different genes indicate that the signal produced in expression assays for different genes are indeed specific for the gene in question.

Example 15

Selection of Targets

Using the EnsMart software release 16.1 from http://www.ensembl.org/EnsMart, the 50 bases from each end off all exons from the Homo Sapiens NCBI 33 dbSNP115 Ensembl Genes were extracted to form a Human Exon50 target set. Using the GetCover program (cf. FIGS. 17A-17T), occurrence of all probe target sequences was calculated and probe target sequences not passing selection criteria according to excess self-complirnentarity, excessive GC content etc. were eliminated. Among the remaining sequences, the most abundant probe target sequences was selected (No. 1, covering 3200 targets), and subsequently all the probe targets having a prevalence above 0.8 times the prevalence of the most abundant (3200×0.8) or above 2560 targets. From the remaining sample the number of new hits for each probe was computed and the product of number of new hits per probe target compared to the existing selection and the total prevalence of the same probe target was computed and used to select the next most abundant probe target sequence by selecting the highest product number. The probe target length (n), and sequence (nmer) and occurrence in the total target (cover), as well as the number of new hits per probe target selection (Newhit), the product of Newhit and cover (newhit×cover) and the number of accumulated hits in the target population from all accumulated probes (sum) is exemplified in the table below.

| No | n | nmer | Newhit | Cover | newhit × cover | sum |
|---|---|---|---|---|---|---|
| 1 | 8 | ctcctcct | 3200 | 3200 | 10240000 | 3200 |
| 2 | 8 | ctggagga | 2587 | 3056 | 7905872 | 5787 |
| 3 | 8 | aggagctg | 2132 | 3074 | 6553768 | 7919 |
| 4 | 8 | cagcctgg | 2062 | 2812 | 5798344 | 9981 |
| 5 | 8 | cagcagcc | 1774 | 2809 | 4983166 | 11755 |
| 6 | 8 | tgctggag | 1473 | 2864 | 4218672 | 13228 |
| 7 | 8 | agctggag | 1293 | 2863 | 3701859 | 14521 |
| 8 | 8 | ctgctgcc | 1277 | 2608 | 3330416 | 15798 |
| 9 | 8 | aggagcag | 1179 | 2636 | 3107844 | 16977 |
| 10 | 8 | ccaggagg | 1044 | 2567 | 2679948 | 18021 |
| 11 | 8 | tcctgctg | 945 | 2538 | 2398410 | 18966 |
| 12 | 8 | cttcctcc | 894 | 2477 | 2214438 | 19860 |
| 13 | 8 | ccgccgcc | 1017 | 2003 | 2037051 | 20877 |
| 14 | 8 | cctggagc | 781 | 2439 | 1904859 | 21658 |
| 15 | 8 | cagcctcc | 794 | 2325 | 1846050 | 22452 |
| 16 | 8 | tggctgtg | 805 | 2122 | 1708210 | 23257 |
| 17 | 8 | cctggaga | 692 | 2306 | 1595752 | 23949 |
| 18 | 8 | ccagccag | 661 | 2205 | 1457505 | 24610 |
| 19 | 8 | ccagggcc | 578 | 2318 | 1339804 | 25188 |
| 20 | 8 | cccagcag | 544 | 2373 | 1290912 | 25732 |
| 21 | 8 | ccaccacc | 641 | 1916 | 1228156 | 26373 |
| 22 | 8 | ctcctcca | 459 | 3010 | 1381590 | 26832 |
| 23 | 8 | ttctcctg | 534 | 1894 | 1011396 | 27366 |
| 24 | 8 | cagcccag | 471 | 2033 | 957543 | 27837 |
| 25 | 8 | ctggctgc | 419 | 2173 | 910487 | 28256 |
| 26 | 8 | ctccacca | 426 | 2097 | 893322 | 28682 |
| 27 | 8 | cttcctgc | 437 | 1972 | 861764 | 29119 |
| 28 | 8 | cttccagc | 415 | 1883 | 781445 | 29534 |
| 29 | 8 | ccacctcc | 366 | 2018 | 738588 | 29900 |
| 30 | 8 | ttcctctg | 435 | 1666 | 724710 | 30335 |

| No | n | nmer | Newhit | Cover | newhit x cover | sum |
|---|---|---|---|---|---|---|
| 31 | 8 | cccagccc | 354 | 1948 | 689592 | 30689 |
| 32 | 8 | tggtgatg | 398 | 1675 | 666650 | 31087 |
| 33 | 8 | tggctctg | 358 | 1767 | 632586 | 31445 |
| 34 | 8 | ctgccttc | 396 | 1557 | 616572 | 31841 |
| 35 | 8 | ctccagcc | 294 | 2378 | 699132 | 32135 |
| 36 | 8 | tgtggctg | 304 | 1930 | 586720 | 32439 |
| 37 | 8 | cagaggag | 302 | 1845 | 557190 | 32741 |
| 38 | 8 | cagctccc | 275 | 1914 | 526350 | 33016 |
| 39 | 8 | ctgcctcc | 262 | 1977 | 517974 | 33278 |
| 40 | 8 | tctgctgc | 267 | 1912 | 510504 | 33545 |
| 41 | 8 | ctgcttcc | 280 | 1777 | 497560 | 33825 |
| 42 | 8 | cttctccc | 291 | 1663 | 483933 | 34116 |
| 43 | 8 | cctcagcc | 232 | 1863 | 432216 | 34348 |
| 44 | 8 | ctccttcc | 236 | 1762 | 415832 | 34584 |
| 45 | 8 | cagcaggc | 217 | 1868 | 405356 | 34801 |
| 46 | 8 | ctgcctct | 251 | 1575 | 395325 | 35052 |
| 47 | 8 | ctccacct | 215 | 1706 | 366790 | 35267 |
| 48 | 8 | ctcctccc | 205 | 1701 | 348705 | 35472 |
| 49 | 8 | cttcccca | 224 | 1537 | 344288 | 35696 |
| 50 | 8 | cttcagcc | 203 | 1650 | 334950 | 35899 |
| 51 | 8 | ctctgcca | 201 | 1628 | 327228 | 36100 |
| 52 | 8 | ctgggaga | 192 | 1606 | 308352 | 36292 |
| 53 | 8 | cttctgcc | 195 | 1533 | 298935 | 36487 |
| 54 | 8 | cagcaggt | 170 | 1711 | 290870 | 36657 |
| 55 | 8 | tctggagc | 206 | 1328 | 273568 | 36863 |
| 56 | 8 | tcctgctc | 159 | 1864 | 296376 | 37022 |
| 57 | 8 | ctggggcc | 159 | 1659 | 263781 | 37181 |
| 58 | 8 | ctcctgcc | 155 | 1733 | 268615 | 37336 |
| 59 | 8 | ctgggcaa | 185 | 1374 | 254190 | 37521 |
| 60 | 8 | ctggggct | 149 | 1819 | 271031 | 37670 |
| 61 | 8 | tggtggcc | 145 | 1731 | 250995 | 37815 |
| 62 | 8 | ccagggca | 147 | 1613 | 237111 | 37962 |
| 63 | 8 | ctgctccc | 146 | 1582 | 230972 | 38108 |
| 64 | 8 | tgggcagc | 135 | 1821 | 245835 | 38243 |
| 65 | 8 | ctccatcc | 161 | 1389 | 223629 | 38404 |
| 66 | 8 | ctgccca | 143 | 1498 | 214214 | 38547 |
| 67 | 8 | ttcctggc | 155 | 1351 | 209405 | 38702 |
| 68 | 8 | atggctgc | 157 | 1285 | 201745 | 38859 |
| 69 | 8 | tggtggaa | 155 | 1263 | 195765 | 39014 |
| 70 | 8 | tgctgtcc | 135 | 1424 | 192240 | 39149 |
| 71 | 8 | ccagccgc | 159 | 1203 | 191277 | 39308 |
| 72 | 8 | catccagc | 122 | 1590 | 193980 | 39430 |
| 73 | 8 | tcctctcc | 118 | 1545 | 182310 | 39548 |
| 74 | 8 | agctggga | 121 | 1398 | 169158 | 39669 |
| 75 | 8 | ctggtctc | 128 | 1151 | 147328 | 39797 |
| 76 | 8 | ttcccagt | 142 | 1023 | 145266 | 39939 |
| 77 | 8 | caggcagc | 108 | 1819 | 196452 | 40047 |
| 78 | 8 | tcctcagc | 105 | 1654 | 173670 | 40152 |
| 79 | 8 | ctggctcc | 103 | 1607 | 165521 | 40255 |
| 80 | 9 | tcctcttct | 127 | 1006 | 127762 | 40382 |
| 81 | 8 | tccagtgt | 123 | 968 | 119064 | 40505 |

Example 16 qPCR for Human Genes

Use of the Probe library is coupled to the use of a real-time PCR design software which can:
- recognise an input sequence via a unique identifier or by registering a submitted nucleic acid sequence
- identify all probes which can target the nucleic acid
- sort probes according to target sequence selection criteria such as proximity to the 3' end or proximity to intron-exon boundaries
- if possible, design PCR primers that flank probes targeting the nucleic acid sequence according to PCR design rules
- suggest available real-time PCR assays based on above procedures.

The design of an efficient and reliable qPCR assay for a human gene is carried out via the software found on www.probelibrary.com The ProbeFinder software designs optimal qPCR probes and primers fast and reliably for a given human gene.

The design comprises the following steps:
1) Determination of the intron positions
   Noise from chromosomal DNA is eliminated by selecting intron spanning qPCR's. Introns are determined by a blast search against the human genome. Regions found on the DNA, but not in the transcript are considered to be introns.
2) Match of the Probe Library to the gene
   Virtually all human transcripts are covered by at least one of the 90 probes, the high coverage is made possible by LNA modifications of the recognition sequence tags.
3) Design of primers and selection of optimal qPCR assay
   Primers are designed with 'Primer3' (Whitehead Inst. For Biomedical Research, S. Rozen and H. J. Skaletsky). Finally the probes are ranked according to selected rules ensuring the best possible qPCR. The rules favor intron spanning amplicons to remove false signals from DNA contamination, small amplicon size for reproducible and comparable assays and a GC content optimized for PCR.

Example 17

Preparation of Ena-Monomers and Oligomers

ENA-T monomers are prepared and used for the preparation of dual labelled probes of the invention.

In the following sequences the X denotes a 2'-O,4'-C-ethylene-5-methyluridine (ENA-T). The synthesis of this monomer is described in WO 00/47599. The reaction conditions for incorporation of a 5-O-Dimethoxytrityl-2'—O, 4'—C-ethylene-5-methyluridine-3'—O—(2-cyanoethyl-N, N-diisopropyl)phosphoramidite corresponds to the reaction conditions for the preparation of LNA oligomers as described in EXAMPLE 6.

The following three dual labelled probes are preparted:

| EQ# | Sequences | MW (Calc.) | MW (Found) |
|---|---|---|---|
| 16533 | 5'-Fitc-ctGmCXmCmCAg-EQL-3' | 4002 Da. | 4001 Da. |
| 16534 | 5'-Fitc-cXGmCXmCmCA-EQL-3' | 3715 Da. | 3716 Da. |
| 16535 | 5'-Fitc-tGGmCGAXXX-EQL-3' | 4128 Da. | 4130 Da. |

X designate ENA-T monomer.
Small letters designate DNA monomers (a, g, c, t).
Fitc = Fluorescein; EQL = Eclipse quencher; Dabcyl = Dabcyl quencher.
MW = Molecular weight.
Capital letters other than 'X' designate methyloxy LNA nucleotides.

REFERENCES AND NOTES

1. Helen C. Causton, Bing Ren, Sang Seok Koh, Christopher T. Harbison, Benita Kanin, Ezra G. Jennings, Tong Ihn Lee, Heather L. True, Eric S. Lander, and Richard A. Young (2001). Remodelling of Yeast Genome Expression in Response to Environmental Changes. Mol. Biol. Cell 12: 323-337 (2001).

2. Frank C. P. Holstege, Ezra G. Jennings, John J. Wyrick, Tong Ihn Lee, Christoph J. Hengartner, Michael R. Green, Todd R. Golub, Eric S. Lander, and Richard A. Young (1998). Dissecting the Regulatory Circuitry of a Eukaryotic Genome. Cell 1998 95: 717-728, 3. Simeonov, Anton and Theo T. Nikiforov, Single nucleotide polymorphism genotyping using short, fluorescently labelled locked nucleic acid (LNA) probes and fluorescence polarization detection, Nucleic Acid Research, 2002, Vol. 30 No 17 e 91.

Variations, modifications, and other implementations of what is described herein will occur to those skilled in the art without departing from the spirit and scope of the invention as described and claimed herein and such variations, modifications, and implementations are encompassed within the scope of the invention.

The references, patents, patent applications, and international applications disclosed above are incorporated by reference herein in their entireties.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11111535B2). An electronic copy of the "Sequence Listing" will also be available from the USPTO upon request and payment of the fee set forth in 37 CFR 1.19(b)(3).

The invention claimed is:

1. A library of oligonucleotide probes, wherein each probe in the library comprises a recognition sequence tag and a detection moiety, wherein the recognition sequence tag has at least one modified monomer analogue that increases the binding affinity for the complementary target sequence relative to the corresponding unmodified oligodeoxyribonucleotide,
   wherein each probe has sufficient stability for sequence-specific binding and detection of its target sequence under stringent conditions,
   wherein each probe has independently a total of 8 or 9 nucleotides,
   wherein the library comprises a total of from 50 to 500 probes,
   wherein the probes in the library hybridize to more than 90% of the mRNAs set forth in SEQ ID NOS: 47-35734, and
   wherein at least one modified monomer analogue is a non-naturally occurring nucleotide analogue, a deoxyribose or ribose analogue, or an internucleotide linkage other than a phosphodiester linkage.

2. The library of claim 1, wherein the detection moiety is a covalently or non-covalently bound minor groove binder or an intercalator selected from the group consisting of asymmetric cyanine dyes, DAPI, SYBR Green I, SYBR Green II, SYBR Gold, PicoGreen, thiazole orange, Hoechst 33342, Ethidium Bromide, 1-O-(1-pyrenylmethyl)glycerol, and Hoechst 33258.

3. The library of claim 1, wherein the at least one modified monomer analogue in the recognition sequence tag comprises an LNA nucleotide.

4. The library of claim 1, wherein at least one probe in the library comprises an SBC nucleobase, 2'-O-methyl, diamine purine, 2-thio uracil, 5-nitroindole, a universal base, intercalating nucleic acid, or minor-groove-binder.

5. The library of claim 1, wherein at least one modified monomer analogue is the internucleotide linkage other than a phosphodiester linkage, and wherein the internucleotide linkage other than phosphodiester linkage is selected from the group consisting of alkyl phosphonate, phosphoramidite, alkyl-phosphotriester, phosphorothioate, and phosphorodithioate linkages.

6. The library of claim 4, wherein at least one of the probes in the library comprises 5-nitroindole.

7. The library of claim 1, wherein the detection moiety comprises a dual label that is detected by the 5' nuclease assay principle.

8. The library of claim 1, wherein at least one probe in the library has a DNA nucleotide at the 5'-end.

9. The library of claim 1, wherein the detection moiety comprises an intercalating fluorophore or minor groove binder, the fluorescence of which is altered upon binding to a double-stranded DNA or DNA-RNA hetero-duplex.

10. The library of claim 1, wherein each probe in the library targets more than 2,200 target sequences among SEQ ID NOS: 47-35734.

11. The library of claim 1, wherein the detection moiety comprises a detectable label at:
    (i) the 5' or the 3' terminus of the recognition sequence tag; or
    (ii) the 5' or the 3' terminus of the probe.

12. The library of claim 11, wherein the detection moiety comprises a detectable label at the 5' or the 3' terminus of the recognition sequence tag.

13. The library of claim 11, wherein the detection moiety comprises detectable labels at the 5' and 3' termini of the recognition sequence tag, and the detectable labels are a fluorophore-quencher pair.

14. The library of claim 11, wherein the detectable label at the 5' or the 3' terminus of the recognition sequence tag is a fluorescein.

15. The library of claim 7, wherein at least one probe in the library further comprise a 5-nitroindole.

16. The library of claim 1, wherein the recognition sequence tag in at least one probe in the library has a $T_m$ of at least 50° C., as measured in an aqueous solution of 10 mM $Na_2HPO_4$, 100 mM NaCl, and 0.1 mM EDTA, at pH 7.0.

17. The library of claim 1, wherein the recognition sequence tag in at least one probe in the library has a $T_m$ of at least 60° C., as measured in an aqueous solution of 10 mM $Na_2HPO_4$, 100 mM NaCl, and 0.1 mM EDTA, at pH 7.0.

* * * * *